United States Patent
Ozaki et al.

(10) Patent No.: US 8,393,242 B2
(45) Date of Patent: Mar. 12, 2013

(54) REMOTE-CONTROLLED ACTUATOR

(75) Inventors: Takayoshi Ozaki, Shizuoka (JP); Hiroshi Isobe, Shizuoka (JP)

(73) Assignee: NTN Corporation, Osaka (JP)

( * ) Notice: Subject to any disclaimer, the term of this patent is extended or adjusted under 35 U.S.C. 154(b) by 0 days.

(21) Appl. No.: 13/024,696

(22) Filed: Feb. 10, 2011

(65) Prior Publication Data

US 2011/0138962 A1    Jun. 16, 2011

Related U.S. Application Data

(63) Continuation of application No. PCT/JP2009/003745, filed on Aug. 5, 2009.

(30) Foreign Application Priority Data

| | | |
|---|---|---|
| Aug. 12, 2008 | (JP) | 2008-207754 |
| Aug. 20, 2008 | (JP) | 2008-211686 |
| Aug. 20, 2008 | (JP) | 2008-211687 |
| Aug. 22, 2008 | (JP) | 2008-213648 |
| Aug. 27, 2008 | (JP) | 2008-217808 |
| Jul. 15, 2009 | (JP) | 2009-166709 |
| Jul. 15, 2009 | (JP) | 2009-166710 |
| Jul. 15, 2009 | (JP) | 2009-166711 |

(51) Int. Cl.
*G05G 11/00* (2006.01)
*B25J 17/00* (2006.01)
*A61B 1/00* (2006.01)

(52) U.S. Cl. ............... 74/479.01; 74/490.05; 74/490.07; 901/41; 600/104; 600/106

(58) Field of Classification Search ................ 74/6, 7 A, 74/7 R, 469, 479.01, 490.07, 490.05, 490.06; 901/41; 73/760, 856; 600/104, 105, 106, 600/107, 108; 606/79, 80, 81, 82; 623/17.11, 623/17.12, 17.13, 17.14
See application file for complete search history.

(56) References Cited

U.S. PATENT DOCUMENTS

| | | | | |
|---|---|---|---|---|
| 2,711,724 | A | * | 6/1955 | Jenny ........................ 123/179.31 |
| 4,141,255 | A | | 2/1979 | Varner |
| 4,265,231 | A | | 5/1981 | Scheller, Jr. et al. |
| 4,299,529 | A | * | 11/1981 | Inaba et al. .................. 414/590 |
| 4,466,429 | A | | 8/1984 | Loscher et al. |
| 4,517,853 | A | * | 5/1985 | Tani et al. .................... 74/89.32 |

(Continued)

FOREIGN PATENT DOCUMENTS

| | | |
|---|---|---|
| JP | 80213/1983 | 5/1983 |
| JP | 11936/1994 | 2/1994 |
| JP | 07-163574 A | 6/1995 |

(Continued)

*Primary Examiner* — Justin Krause
*Assistant Examiner* — Adam D Rogers
(74) *Attorney, Agent, or Firm* — Pierce Atwood LLP; Kevin M. Farrell; David J. Wilson

(57) ABSTRACT

A remote controlled actuator includes a spindle guide section (3) of an elongated configuration, a distal end member (2) fitted to a distal end of the spindle guide section (3) through a distal end member connecting unit (15) for alteration in attitude, a tool (1) rotatably provided to the distal end member (2), a tool rotating drive source (41) for rotating the tool, and an attitude altering drive source (42) for manipulating the attitude of the distal end member. The distal end member rotatably supports a spindle (13) then holding the tool (1). The spindle guide section (3) includes a rotary shaft (22) for transmitting rotation of the tool rotating drive source to the spindle and a guide hole (30a). A flexible attitude altering member (31) capable of altering the attitude of the distal end member is reciprocally movably inserted within the guide hole (30a).

19 Claims, 41 Drawing Sheets

U.S. PATENT DOCUMENTS

| | | | |
|---|---|---|---|
| 4,787,262 A * | 11/1988 | Kozawa et al. | 74/490.06 |
| 5,405,344 A | 4/1995 | Williamson et al. | |
| 5,738,481 A * | 4/1998 | Rogers | 414/744.6 |
| 7,104,072 B2 * | 9/2006 | Thompson | 60/786 |
| 7,717,653 B2 * | 5/2010 | Miyata et al. | 408/127 |
| 2007/0258782 A1 | 11/2007 | Miyata et al. | |
| 2007/0265653 A1 | 11/2007 | Suzuki | |

FOREIGN PATENT DOCUMENTS

| | | |
|---|---|---|
| JP | 2001-17446 A | 1/2001 |
| JP | 2005-528159 A | 9/2005 |
| JP | 2007-301149 A | 11/2007 |
| JP | 2007-301641 A | 11/2007 |
| WO | 03/101308 A1 | 12/2003 |

* cited by examiner

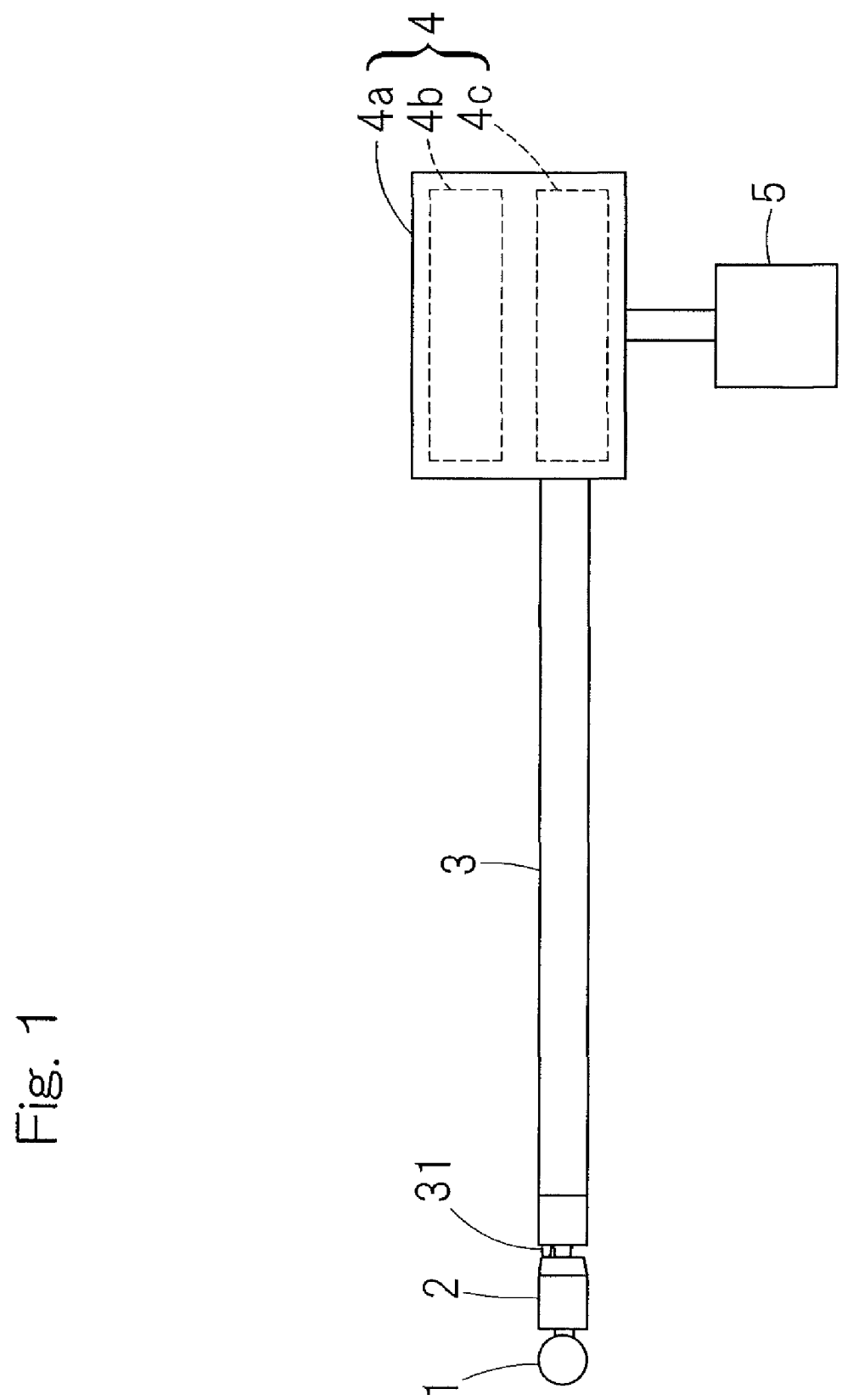

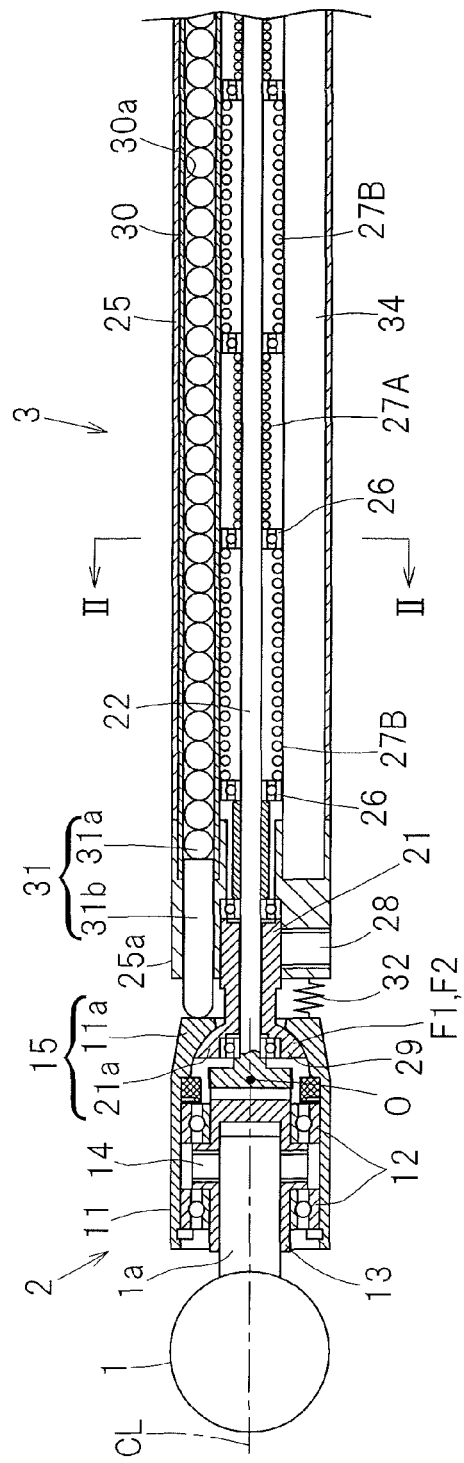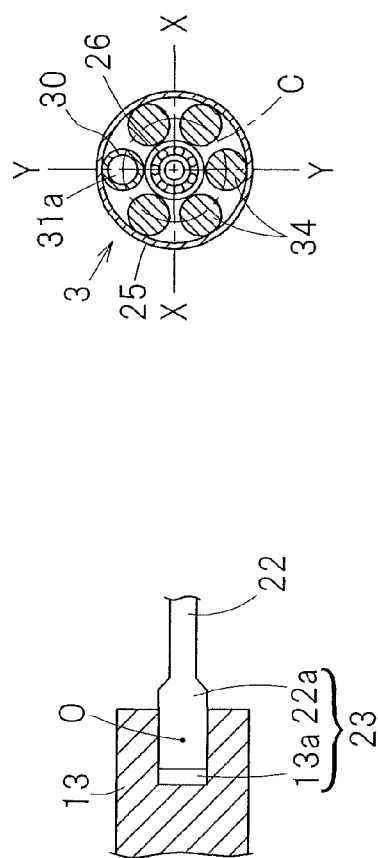
Fig. 2A
Fig. 2B
Fig. 2C

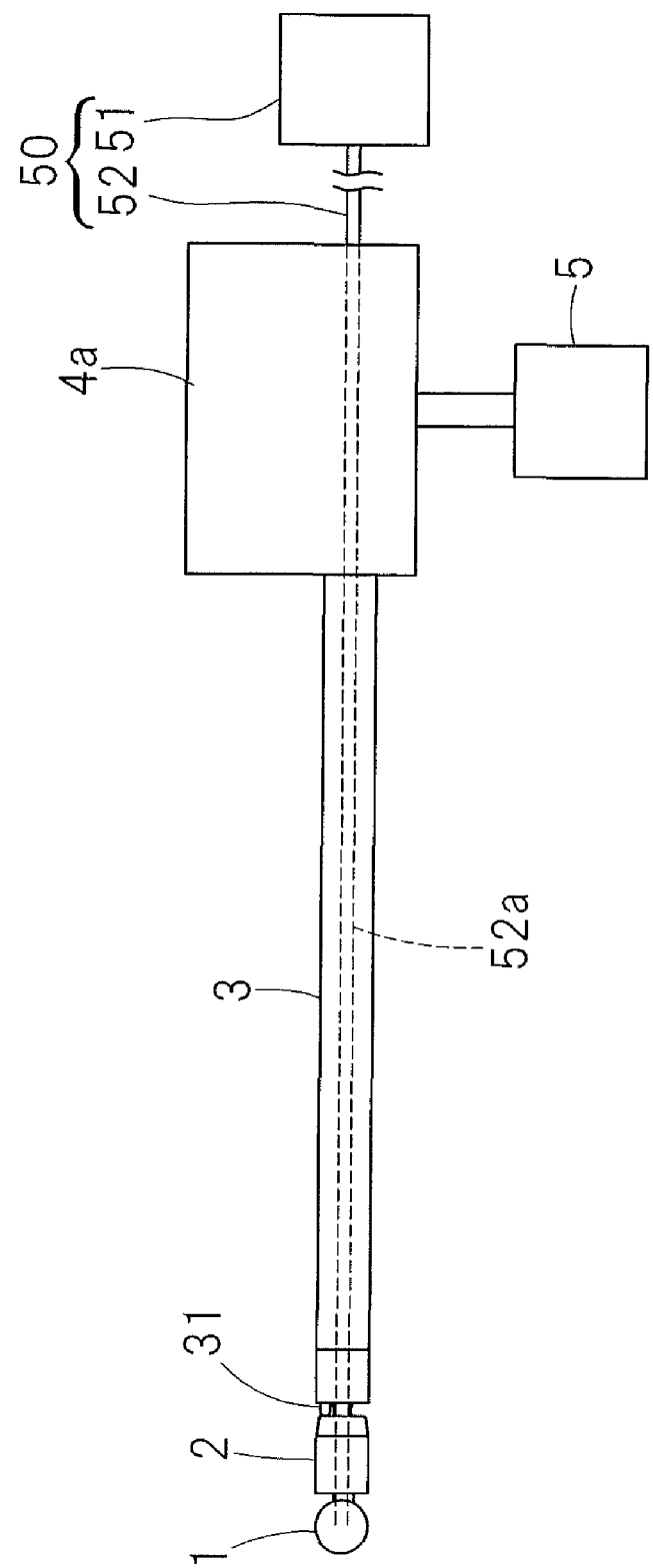

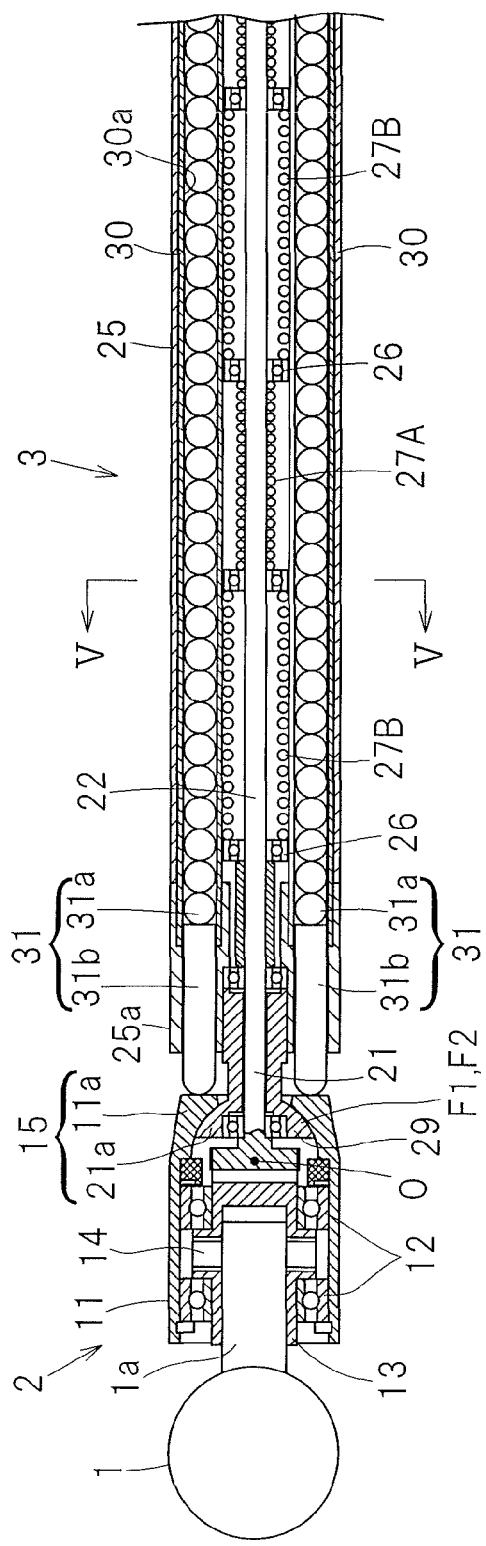
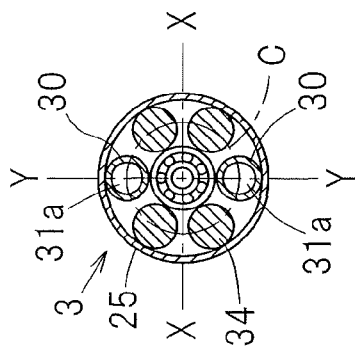
Fig. 5A
Fig. 5B

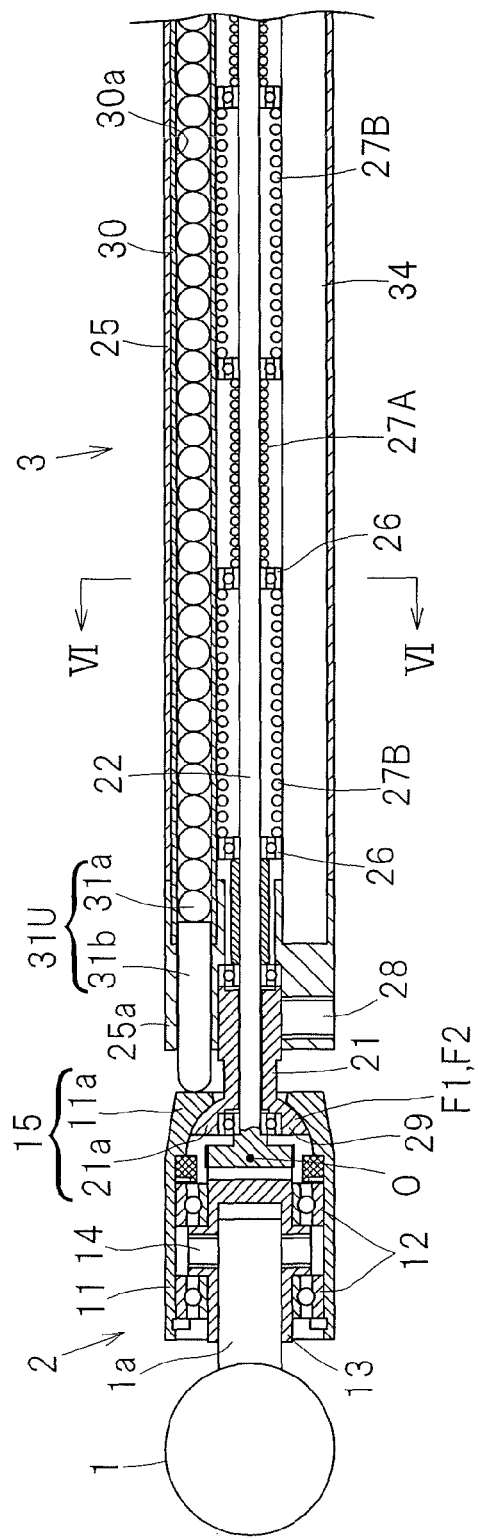
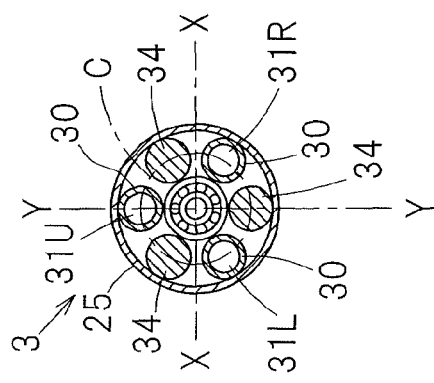
Fig. 6A
Fig. 6B

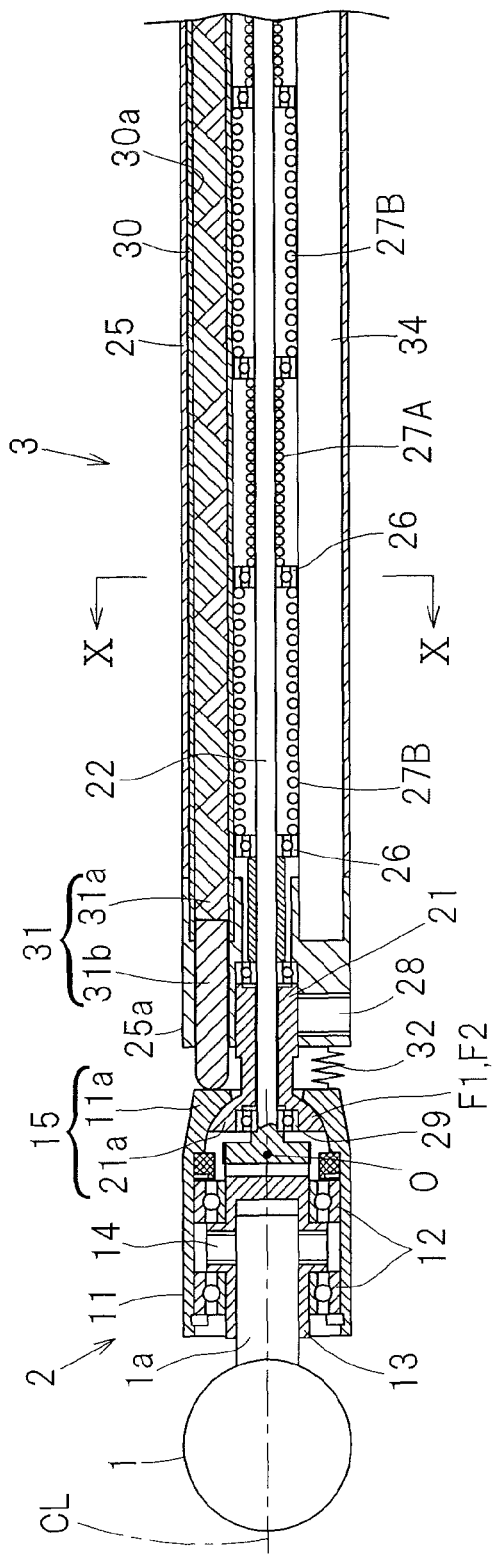
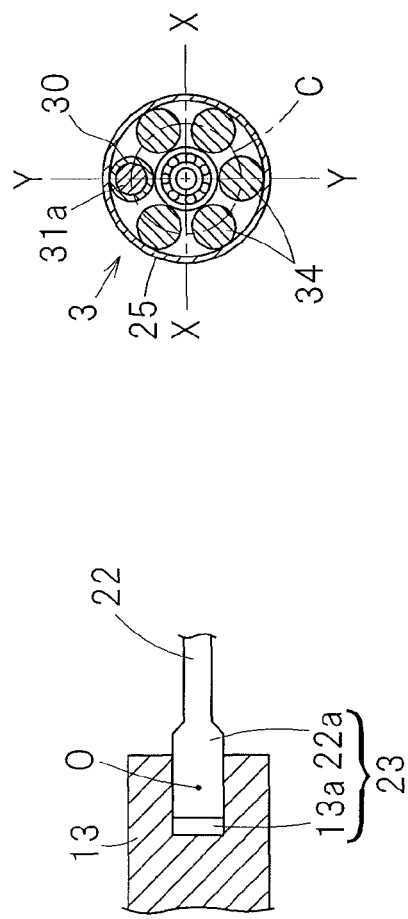
Fig. 10A
Fig. 10B
Fig. 10C

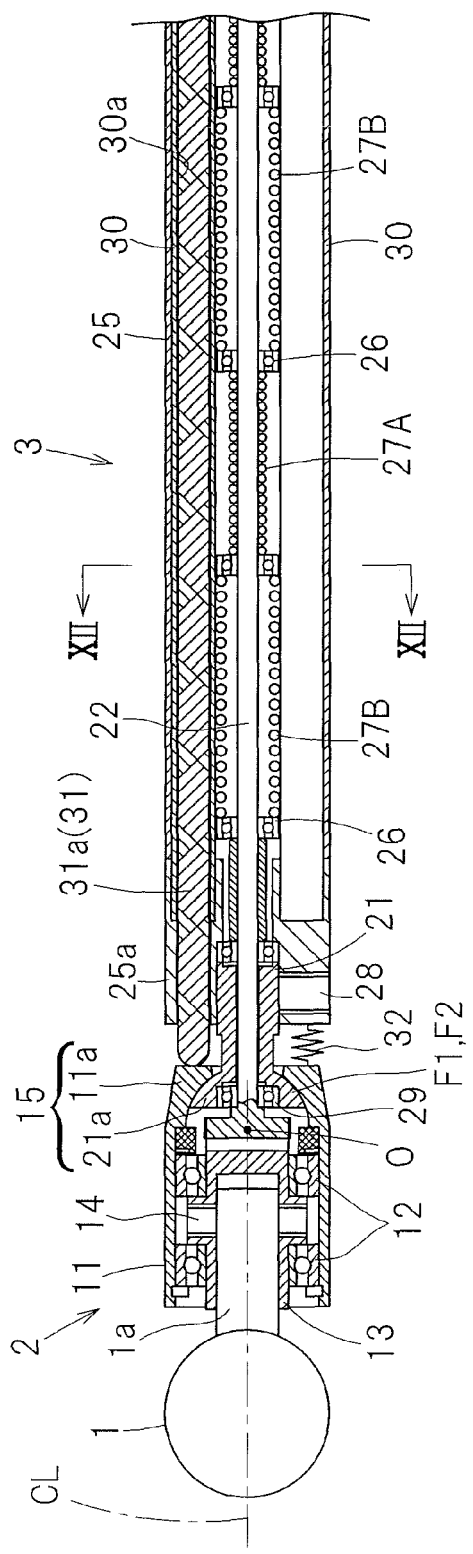
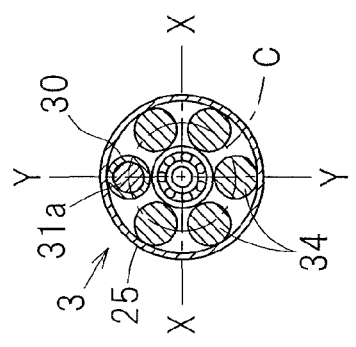
Fig. 12A
Fig. 12B

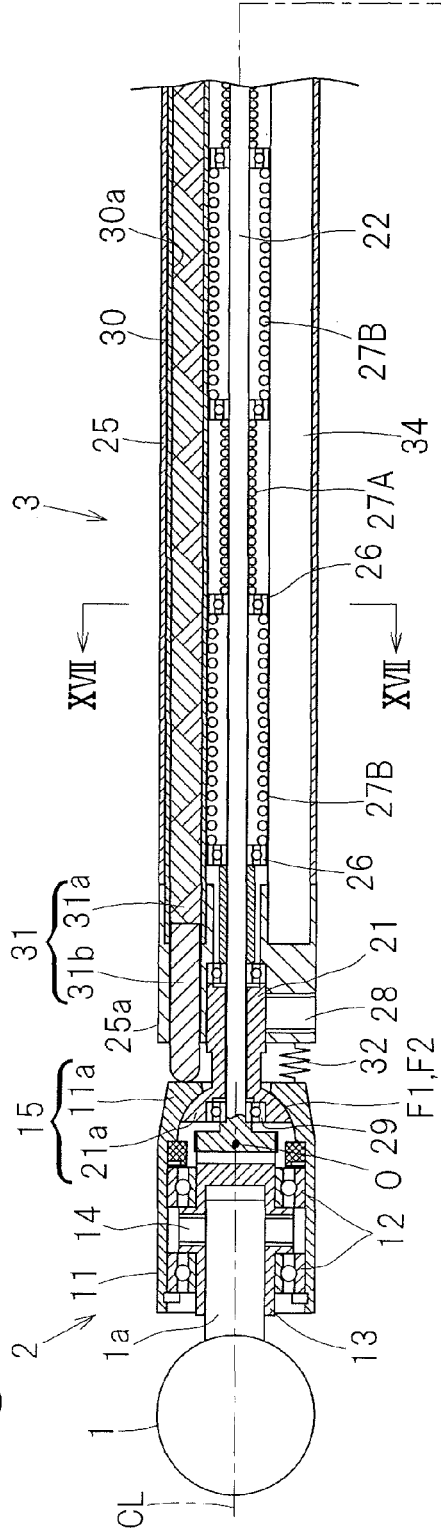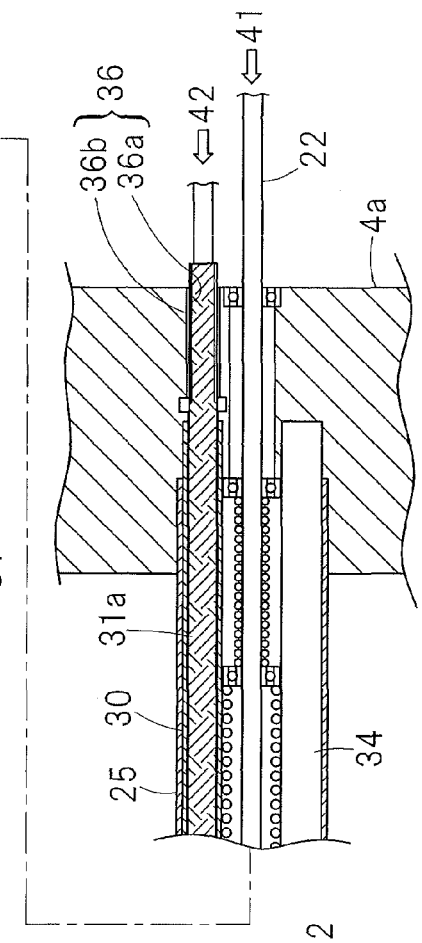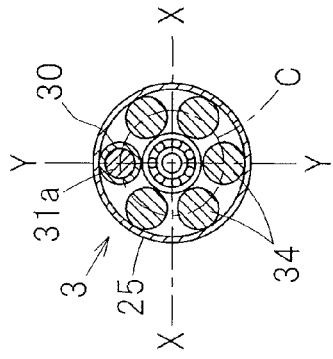

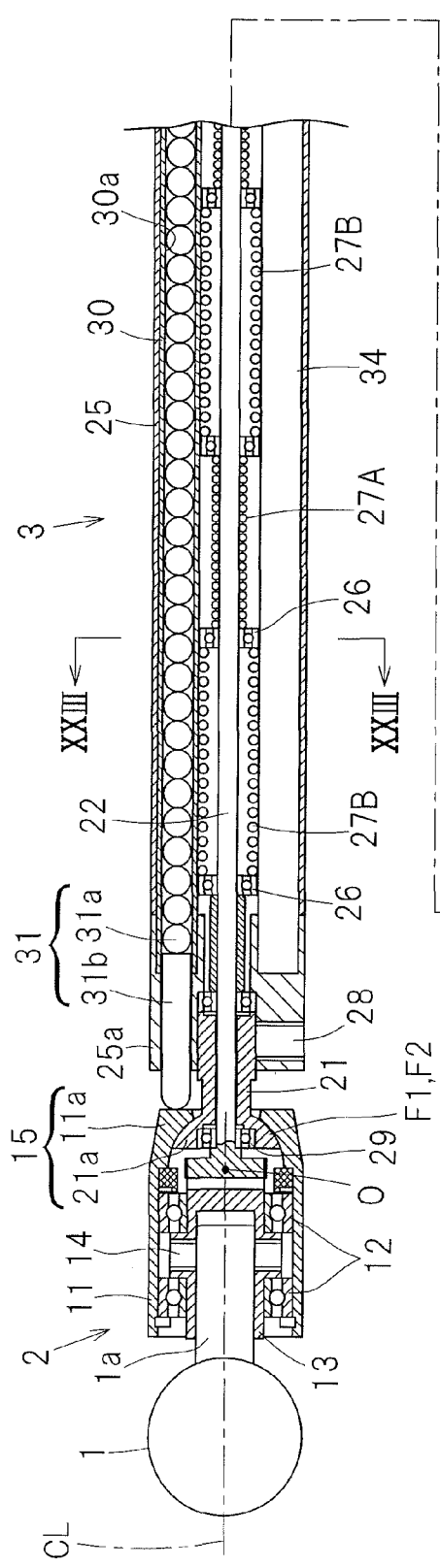
Fig. 23A
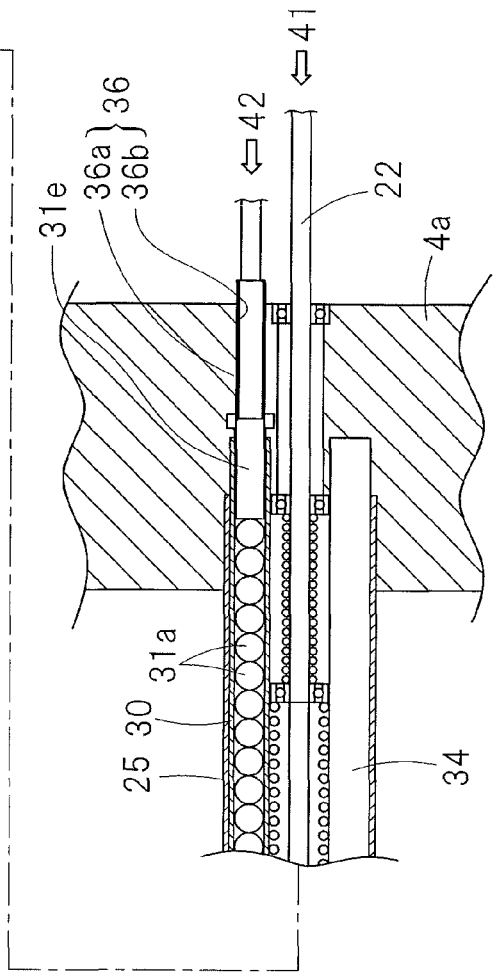
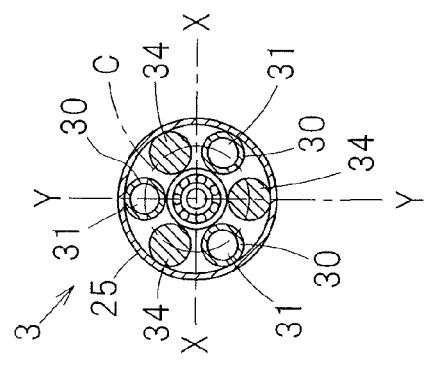
Fig. 23B

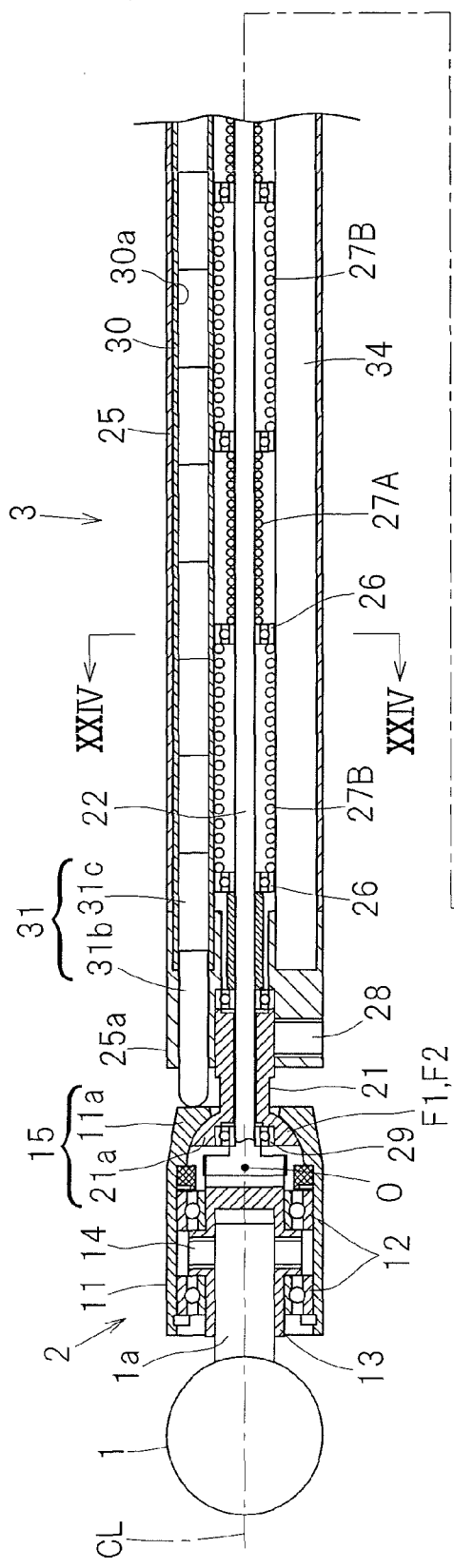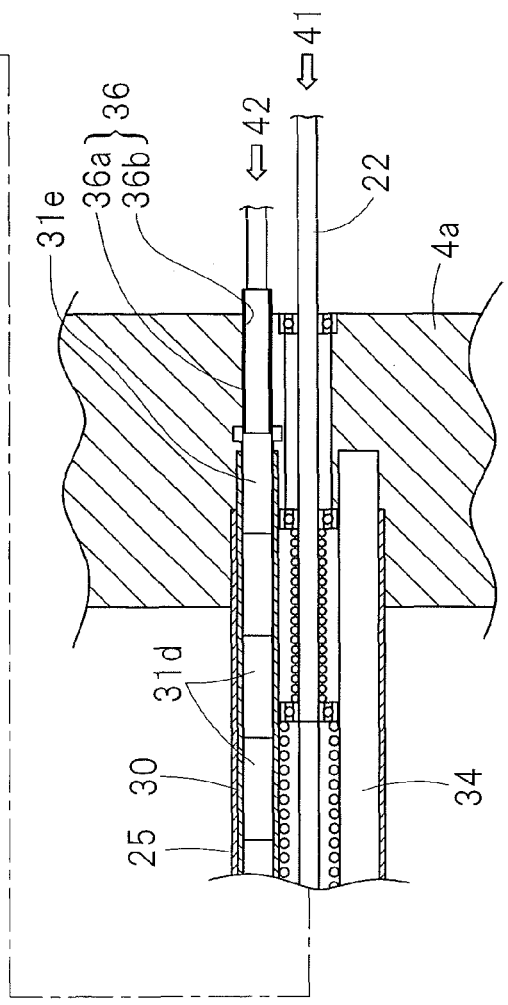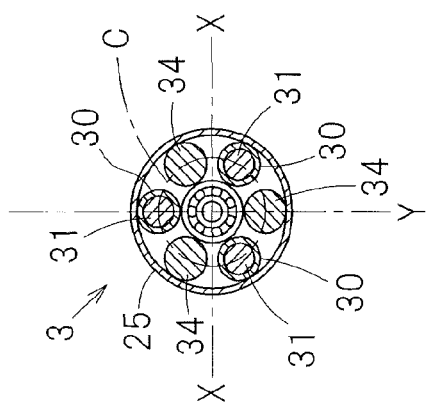
Fig. 24A
Fig. 24B

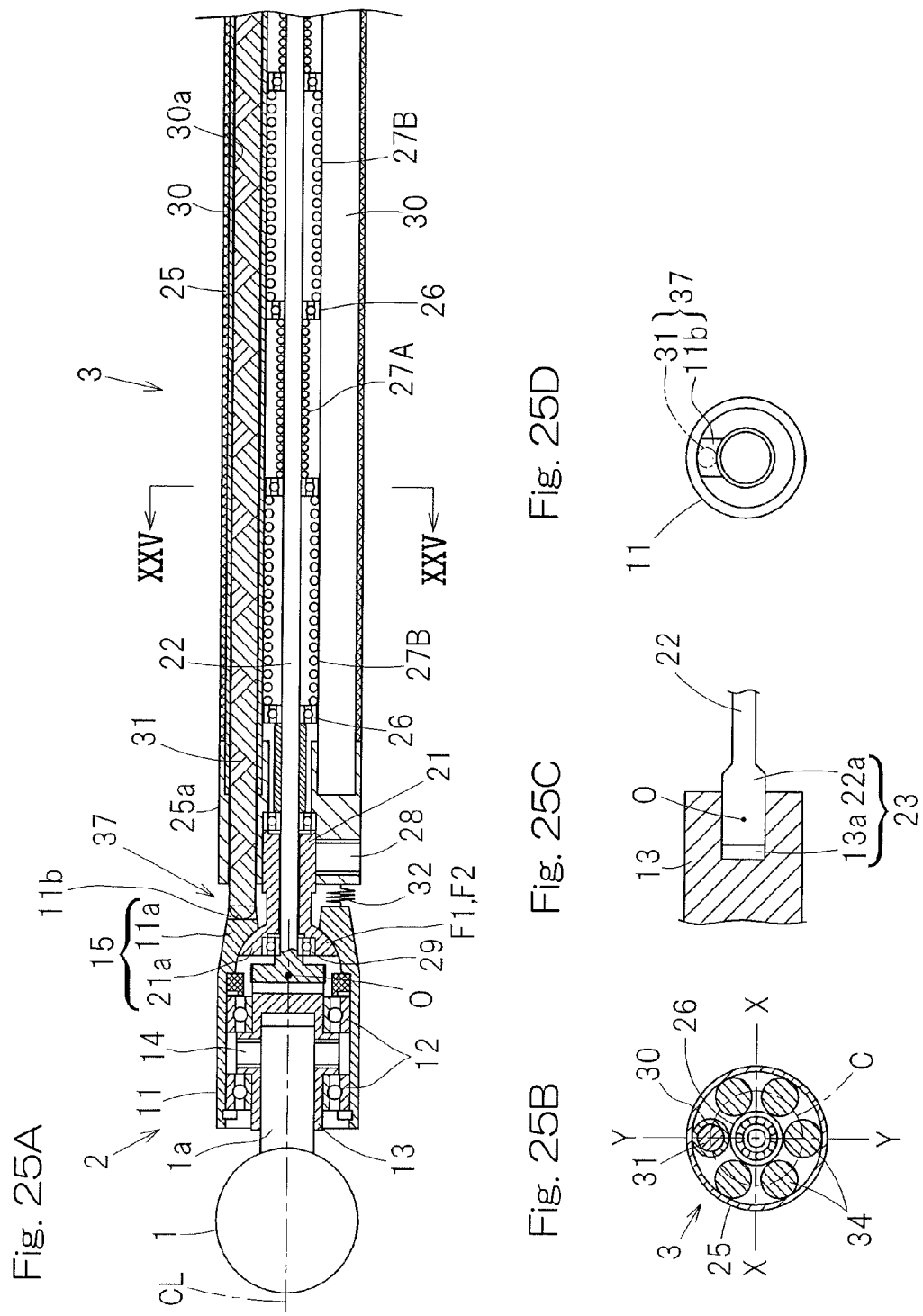

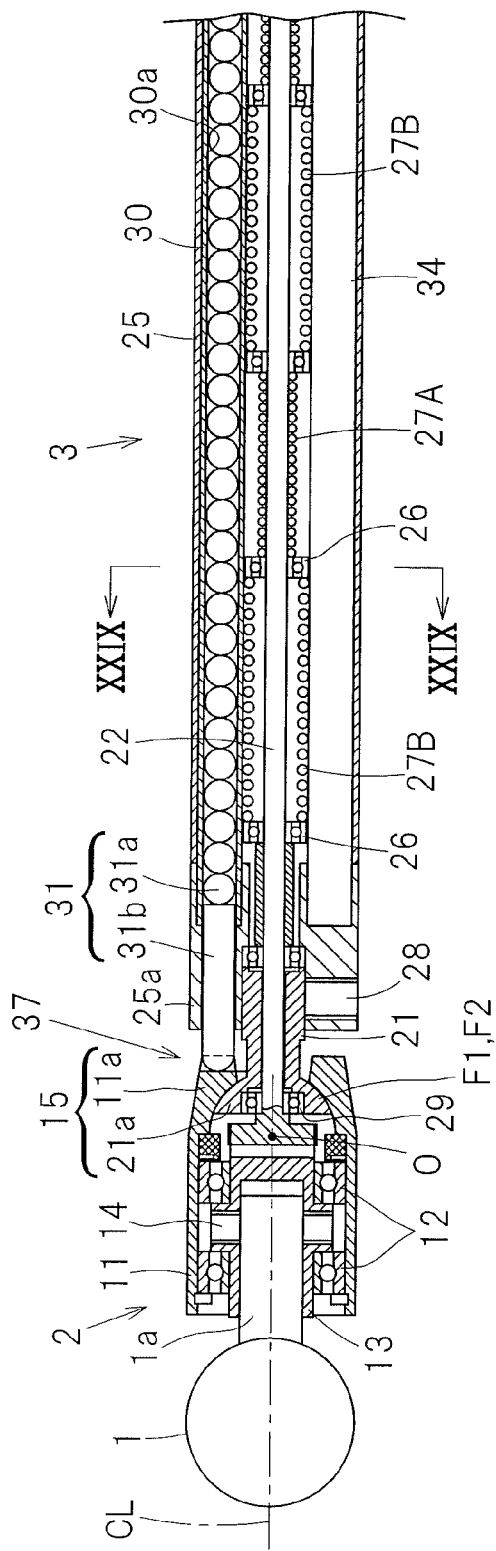
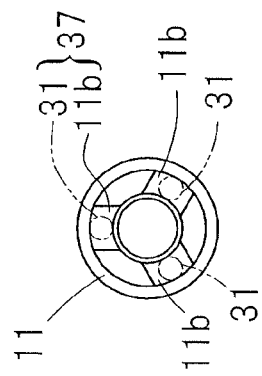
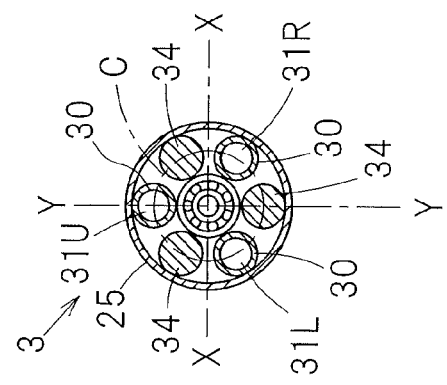
Fig. 29A
Fig. 29C
Fig. 29B

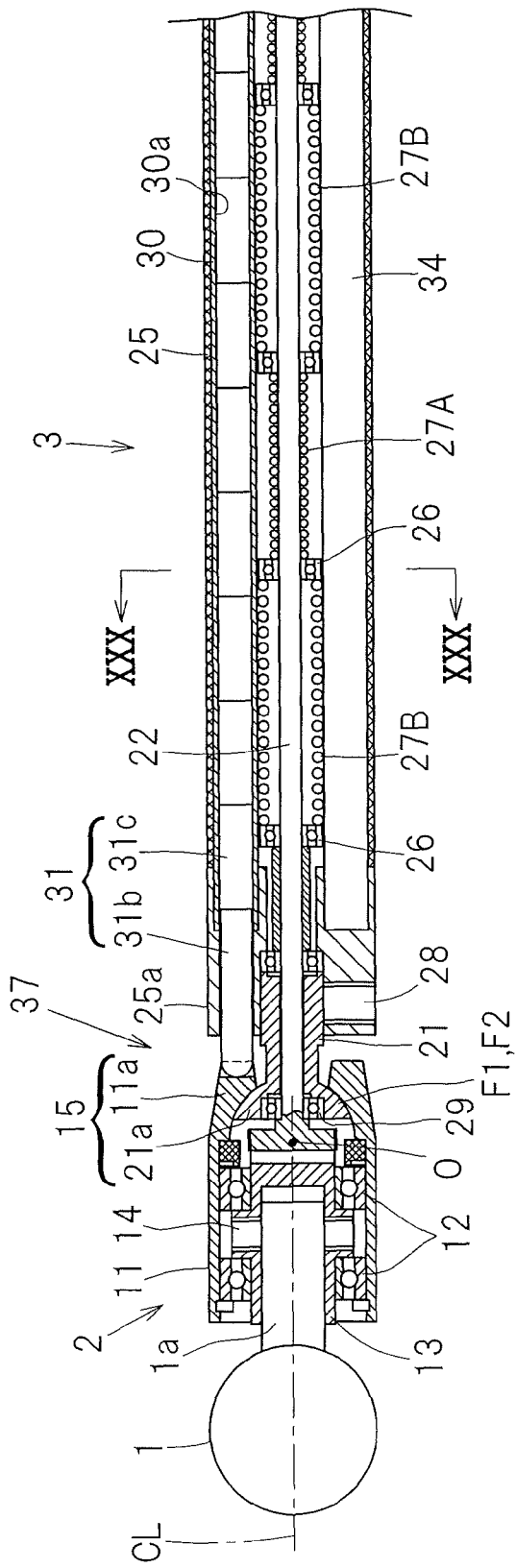
Fig. 30A
Fig. 30B
Fig. 30C

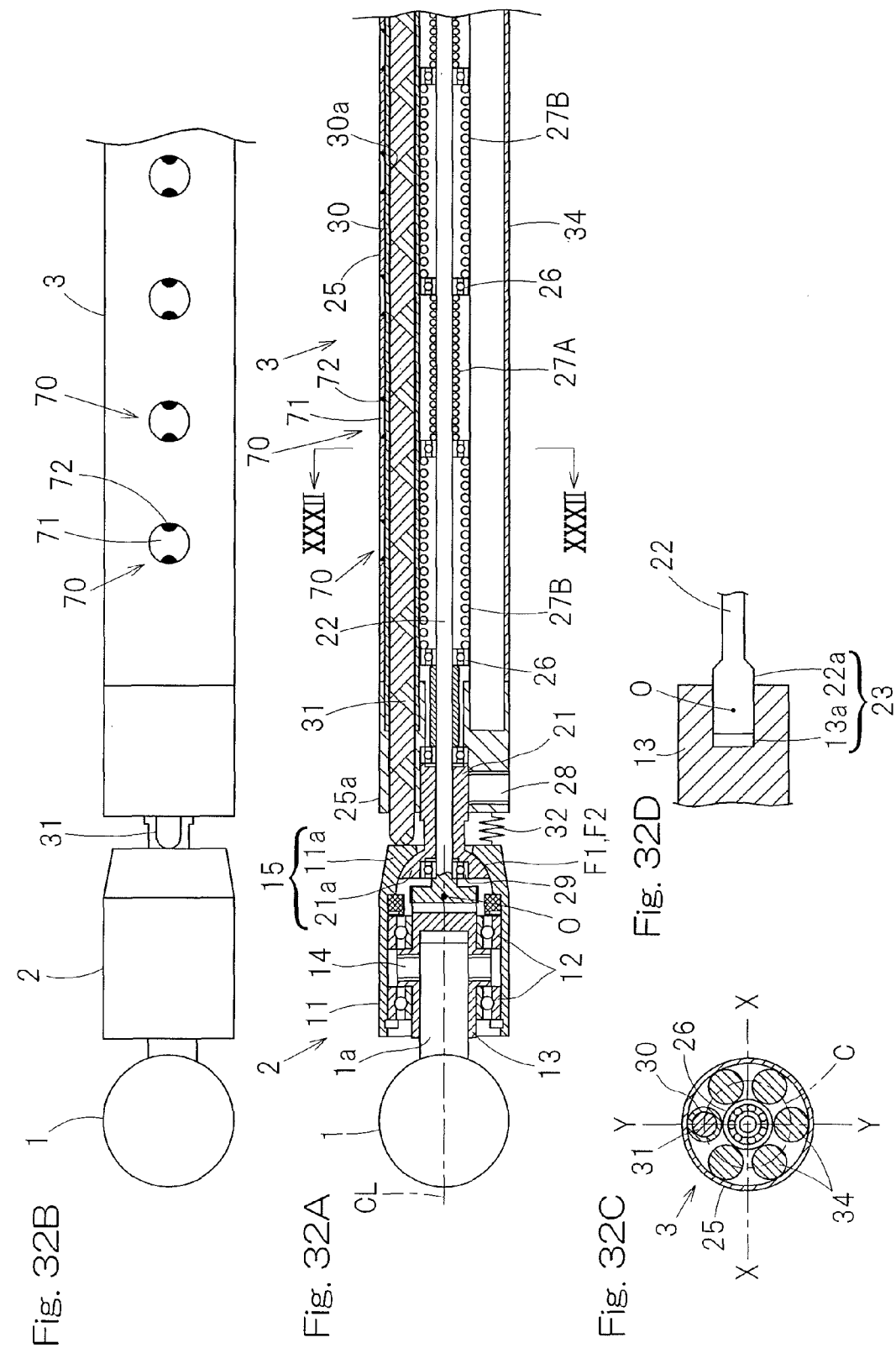

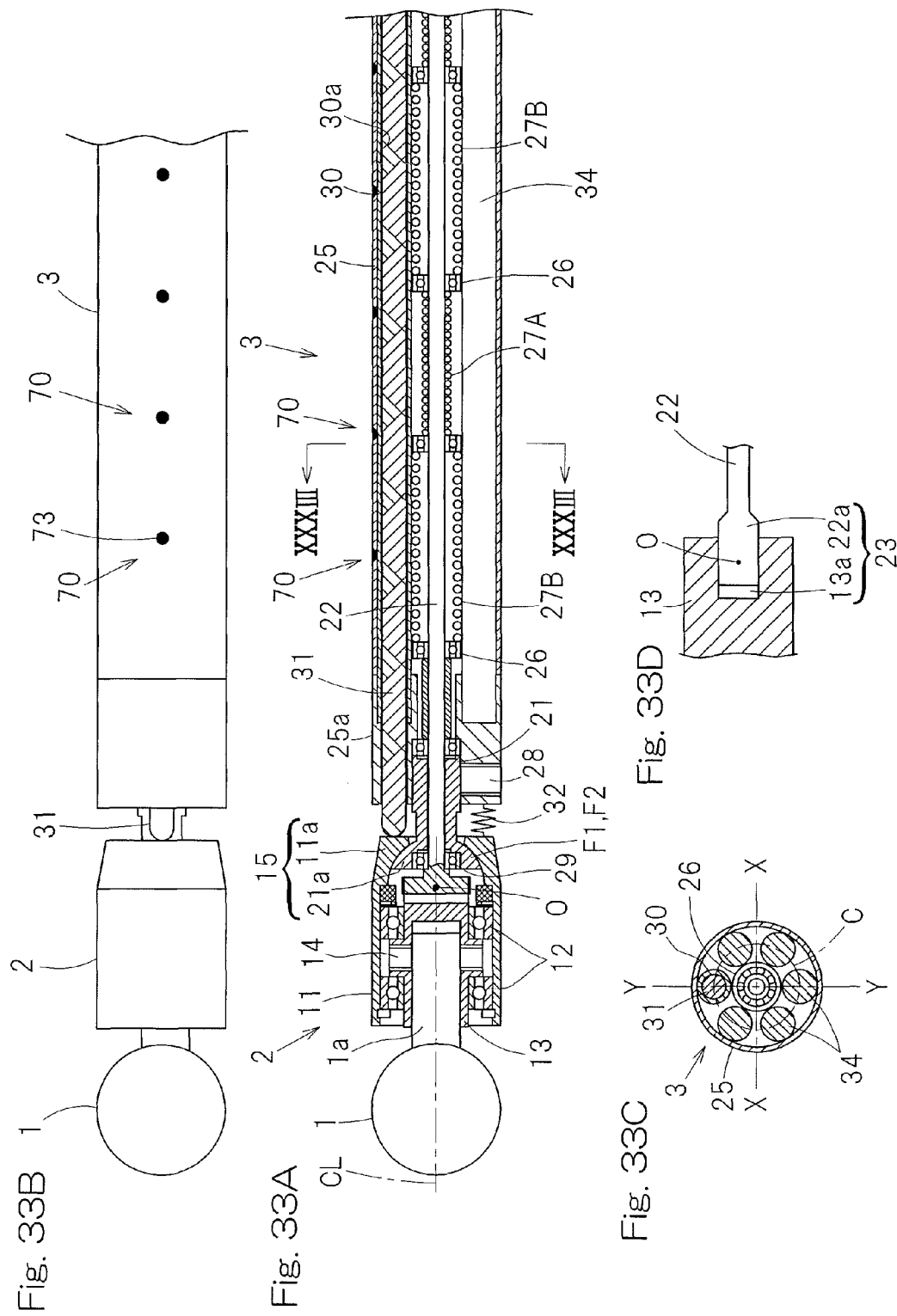

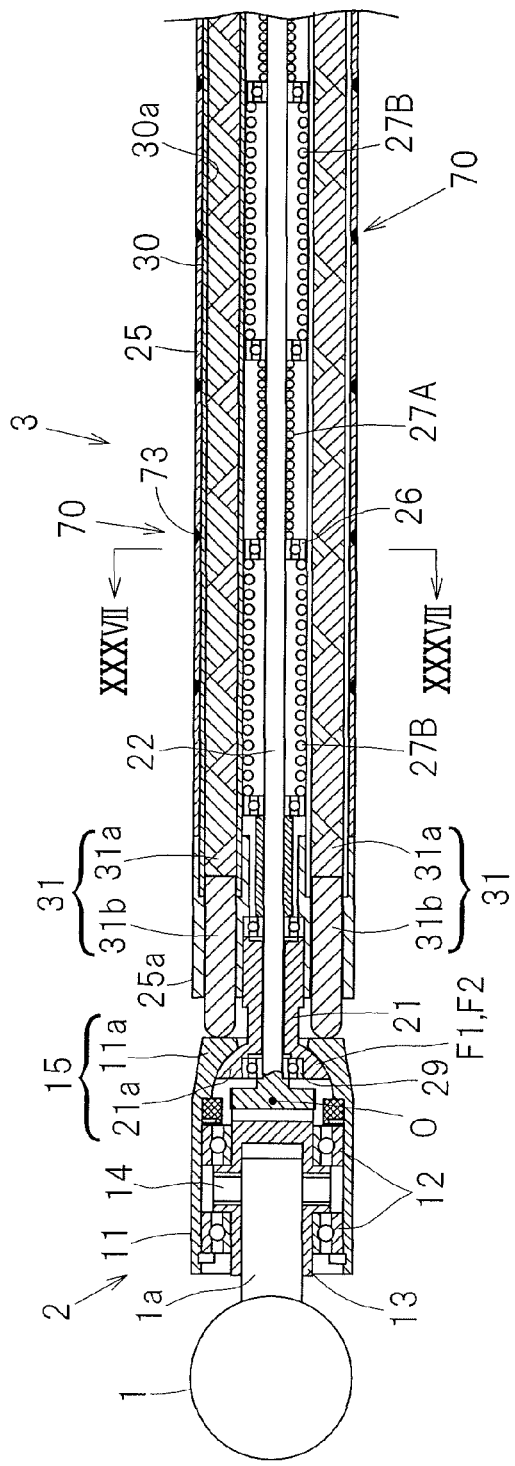
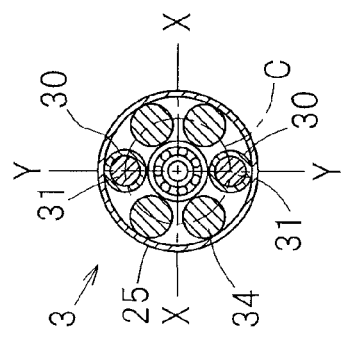
Fig. 37A
Fig. 37B

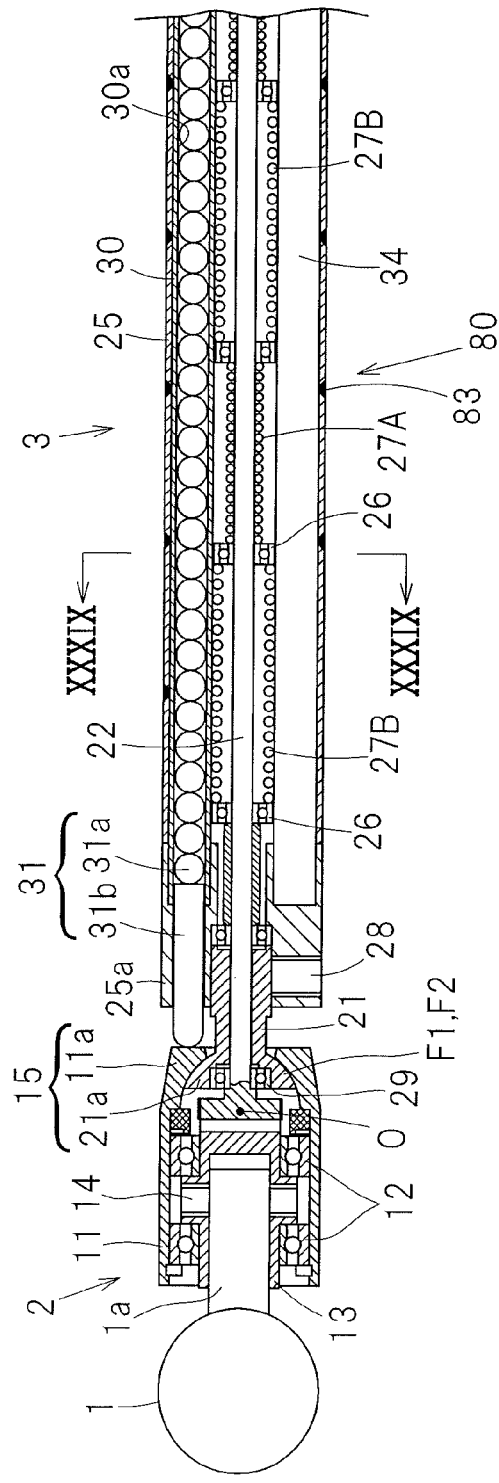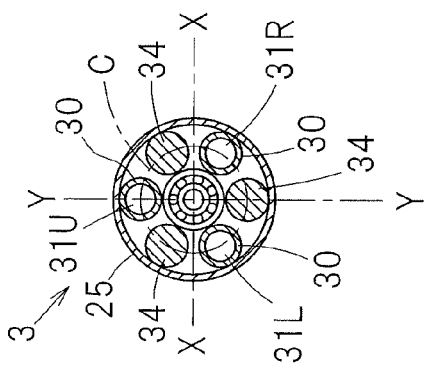
Fig. 39A
Fig. 39B

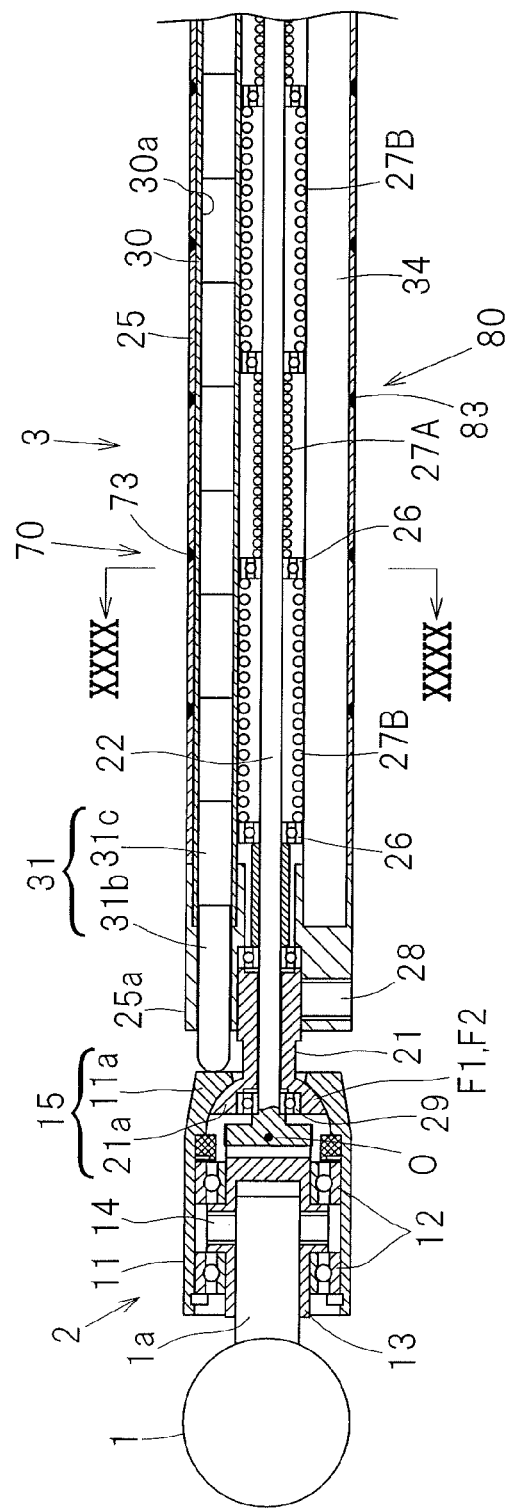
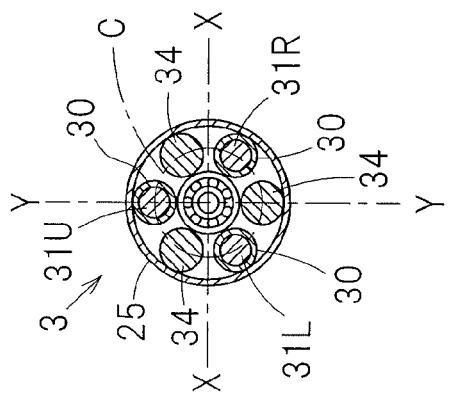
Fig. 40A
Fig. 40B

REMOTE-CONTROLLED ACTUATOR

CROSS REFERENCE TO THE RELATED APPLICATION

This application is a continuation application, under 35 U.S.C. §111(a), of international application No. PCT/JP2009/003745, filed Aug. 5, 2009, which claims priority to Japanese patent application No. 2008-207754, filed Aug. 12, 2008; Japanese patent applications No. 2008-211686 and No. 2008-211687, both filed Aug. 20, 2008; Japanese patent application No. 2008-213648, filed Aug. 22, 2008; Japanese patent application No. 2008-217808, filed Aug. 27, 2008; and Japanese patent applications No. 2009-166709, No. 2009-166710 and No. 2009-166711, all three filed Jul. 15, 2009, the entire disclosures of which are herein incorporated by reference as a part of this application.

BACKGROUND OF THE INVENTION

The present invention relates to a remote controlled actuator for use in medical and machine processing fields and capable of changing the attitude of a machine tool.

DESCRIPTION OF THE PRIOR ART

Remote controlled actuators are currently available; some are used in the medical field for osteal treatment and some are used in the mechanical processing field for drilling and cutting a bone. Any of those remote controlled actuators controls by remote control a machine tool fitted to a distal end of an elongated pipe of a linear or curved configuration. It is, however, that since the conventional remote controlled actuator is designed solely to control only the rotation of the machine tool by remote control, difficulties have been encountered in processing of a complicated shape and processing at a site difficult to view with eyes from the outside in the medical field. Also, in the drilling process, the capability of processing not only the linear line, but also the curved configuration is often required. In addition, in the cutting process, the capability is required to perform the process at a site deep in grooves. In the following description, conventional art and problems inherent in the remote controlled actuator will be discussed with reference to the medical field.

In the orthopedic field, the artificial joint replacement is well known, in which a joint, of which bone has been abraded by due to bone deterioration, is replaced with an artificial joint. The joint replacement surgery requires a living bone of a patient to be processed to enable an artificial joint to be implanted. In order to enhance the strength of postoperative adhesion between the living bone and the artificial joint, such processing is required to be performed precisely and accurately in conformity to the shape of the artificial joint.

By way of example, during the hip join replacement surgery, a thigh bone is opened to secure access of an artificial joint into the femoral marrow cavity. In order to secure a strength of contact between the artificial joint and the bone, surfaces of contact of the artificial joint and the bore must be large and so the opening for insertion of the artificial joint is processed to represent an elongated shape extending deep into the bone. As a medical actuator used in cutting the bone in a manner described above, the actuator is known, in which a tool is rotatably provided in a distal end of an elongated pipe and, on the other hand, a drive source such as, for example, a motor is mounted on a proximal end of the pipe so that the tool can be driven through a rotary shaft disposed inside the elongated pipe. (See, for example, the Patent Document 1 listed below.) Since in this type of medical actuator a rotatable element that is exposed bare to the outside is only the tool at the distal end of the elongated pipe, the tool can be inserted deep into the bone.

The surgical operation for artificial joint replacement generally accompanies skin incision and muscular scission. In other words, the human body must be invaded. In order to minimize the postoperative trace, it is quite often desirable that the elongated pipe referred to above is not necessarily straight, but is moderately curved. To meet with this desire, the following technique has hitherto been suggested. For example, the Patent Document 2 listed below discloses the elongated pipe having its intermediate portion curved double to displace an axial position of the distal end of the pipe relative to the longitudinal axis of the proximal end of the same pipe. To make the axial position of the distal end of the pipe relative to the longitudinal axis of the proximal end of the same pipe is also known from other publications. Also, the Patent Document 3 listed below discloses the elongated pipe rotated 180°.

PRIOR ART LITERATURE

[Patent Document 1] JP Laid-open Patent Publication No. 2007-301149
[Patent Document 2] U.S. Pat. No. 4,466,429
[Patent Document 3] U.S. Pat. No. 4,265,231
[Patent Document 4] JP Laid-open Patent Publication No. 2001-17446

If in a condition, in which the artificial joint is inserted into an artificial joint insertion hole formed in the living bone, a large gap exist between the living bone and the artificial joint, a large length of time is required to accomplish the postoperative adhesion between the living bone and the artificial joint and, therefore, it is considered desirable that the gap should be as small as possible. Also, it is important that respective surfaces of contact between the living bone and the artificial joint be smooth, and accordingly, a high precision is required in processing the artificial joint insertion hole. Whatever the pipe take any shape, the working range of the tool is limited by the shape of the pipe and, therefore, it is difficult to widen the working range of the tool to process the artificial joint insertion hole so that the living bone and the artificial joint may can have smooth contact surfaces and, yet, the gap between the living bone and the artificial joint may be small while skin incision and muscular scission are minimized at the same time.

In general, it is quite often that the patient's bone, where an artificial joint is to be implanted, exhibits a strength lowered as a result of aging and, in a certain case, the bone itself is deformed. Accordingly, the processing of the artificial joint insertion hole is more difficult to achieve than generally considered.

In view of the foregoing, the applicant or assignee of the present invention has attempted to provide a remote controlled actuator of a type, in which the attitude of the tool coupled to the distal end can be changed by remote control so that the processing of the artificial joint insertion hole can be relatively easily and accurately performed. This is because if the attitude of the tool can be changed, the tool can be maintained at a proper attitude regardless of the shape of the pipe. It has, however, been found that since the tool is connected to the distal end of the elongated pipe, disposition of a mechanism for changing the attitude of the tool is considerably limited and, therefore, artifices are required to overcome those limitations. Also, since the pipe may have a curved shape, it is desired that the tool may assume a stabilized attitude or posture at all times so that even when the pipe has a curved shape, the attitude can be assuredly changed even in that case and the processing can be performed accurately. In addition, in order to prevent the elongated pipe from being flexed, the pipe must have a sufficient rigidity.

It is to be noted that in the case of the medical actuator having no elongated pipe used therein, a portion where the tool is mounted can change its attitude relative to a portion to be gripped by hand (See, for example, the Patent Document 4 listed above.), but nothing has yet been suggested in the art that the attitude of the tool can be changed by remote control.

SUMMARY OF THE INVENTION

The present invention is intended to provide a remote controlled actuator of a type, in which the attitude of the tool coupled to the distal end of the elongated pipe can be changed by remote control, in which the attitude can be assuredly changed even in a condition in which a spindle guide portion as the pipe is curved, in which the attitude of the tool is stabilized at all times, and in which the spindle guide portion as the pipe has a high rigidity.

The remote controlled actuator according to the present invention includes a spindle guide section of an elongated configuration, a distal end member fitted to a tip end of the spindle guide section through a distal end member connecting unit for alteration in attitude, a tool rotatably fitted to the distal end member, a tool rotating drive source for rotating the tool, and an attitude altering drive source for manipulating the attitude of the distal end member. The distal end member rotatably supports a spindle for holding the tool. The spindle guide section includes a rotary shaft for transmitting rotation of the tool rotating drive source to the spindle and having a guide hole defined therein so as to extend to both ends, and a flexible attitude altering member reciprocally movably inserted within the guide hole for altering the attitude of the distal end member. When the flexible attitude altering member is, while a tip end thereof is held in contact with the distal end member, selectively advanced and retracted one at a time by the attitude altering drive source.

According to the above construction, as a result of rotation of the tool fitted to the distal end member, cutting of a bone or the like take place. In such case, when the attitude altering member is selectively advanced and retracted one at a time by the attitude altering drive source, the tip end of the attitude altering member works on the distal end member to allow the attitude of the distal end member, fitted to the tip end of the spindle guide section through the distal end member connecting unit for alteration in attitude, to alter. The attitude altering drive source is provided at a position spaced from the distal end member and the alteration of the attitude of the distal end member is carried out by remote control. Since the attitude altering member is passed through the guide hole, the attitude altering member can work on the distal end member properly at all times without being displaced in a direction transverse to the longitudinal direction thereof, and the operation to alter the attitude of the distal end member takes place accurately. Also, since the attitude altering member is flexible, the alteration of the attitude of the distal end member can be accomplished assuredly even when the spindle guide section is curved.

In the present invention, the attitude altering member may be an attitude altering wire.

According to the above described construction, when the attitude altering wire is selectively advanced and retracted one at a time by the attitude altering drive source, the tip end of the attitude altering wire works on the distal end member directly or indirectly to allow the attitude of the distal end member to alter. Since the attitude altering member is passed through the guide hole, the attitude altering member can work on the distal end member properly at all times without being displaced in a direction transverse to the longitudinal direction thereof, and the operation to alter the attitude of the distal end member takes place accurately. Also, since the attitude altering member is flexible, the alteration of the attitude of the distal end member can be accomplished assuredly even when the spindle guide section is curved.

In the present invention, there may be provided a drive mechanism unit for transmitting the operation of the attitude altering drive source to the attitude altering member. The drive mechanism unit includes a screw mechanism made up of a male screw portion, formed in a base end of the attitude altering member, and a female screw portion fixed to a drive unit housing for accommodating the drive mechanism unit and engaged with the male screw portion. The drive unit housing is coupled with the base end of the spindle guide section. The attitude altering drive source is a rotary actuator and the attitude altering member is selectively advanced and retracted one at a time by the action of the screw mechanism when the base end of the attitude altering member is rotated by the rotary actuator.

According to the above described construction, when an external force acts on the tool and/or the distal end member, an axially acting force acts from the distal end member on the attitude altering member. However, the attitude altering drive source is a rotary actuator and, hence, since when the base end of the attitude altering member is rotated by the rotary actuator, the attitude altering member is selectively advanced and retracted one at a time, it does not move in the axial direction unless the attitude altering member rotates in the direction it should be. For this reason, the attitude stability of the distal end member relative to the external force is feasible.

The attitude altering drive source is provided at a position spaced from the distal end member and, therefore, the alteration of the attitude of the distal end member can be accomplished by remote control. Also, since the rotary actuator is employed for the attitude altering drive source, it is sufficient to transmit the rotary output of the rotary actuator to the base end of the attitude altering member and, hence, the drive mechanism unit for alteration of the attitude can be assembled simple.

In the present invention, a rotation-reducing and transmitting mechanism or a reduction gear system may be employed for decelerating the rotation of the rotary actuator and transmitting to the base end of the attitude altering member.

The use of the rotation-reducing and transmitting mechanism is effective to allow the base end of the attitude altering member to be rotated at a low speed even with the rotary actuator of a compact size and capable of rotating at a high speed and, therefore, the compact rotary actuator can be employed.

In the present invention, one or both of the tool rotating drive source and the attitude altering drive source may be provided within a drive unit housing to which the base end of the spindle guide section is connected.

If one or both of the tool rotating drive source and the attitude altering drive source is provided within the drive unit housing, the number of component parts provided outside the drive unit housing can be reduced, allowing the remote controlled actuator as a whole to be simplified in structure.

In the present invention, the tool rotating drive source and the attitude altering drive source may be provided outside a drive unit housing to which the base end of the spindle guide section is connected. If the tool rotating drive source and the attitude altering drive source are provided outside a drive unit housing, the drive unit housing can be downsized. For this reason, the handleability of the remote controlled actuator of a type that is manipulated with the drive unit housing hand-held can be increased.

In the present invention, where one or both of the tool rotating drive source and the attitude altering drive source is provided outside a drive unit housing, it is recommended that a drive force of one of the tool rotating drive source and the attitude altering drive source, which is provided outside the drive unit housing, is transmitted to the rotary shaft or the attitude altering member through a flexible cable. With this construction, positioning of the drive source(s) outside the drive unit housing relative to the drive unit housing can be flexible thereby enhancing handleability of the remote controlled actuator.

In the present invention, the attitude of the distal end member may be altered when the attitude altering member operates either to press the distal end member or to pull the distal end member. In either case, the distal end member can be favorably altered in attitude by means of the attitude altering wire.

In the present invention, the spindle guide section may include an outer shell pipe forming an outer shell for the spindle guide section, a rotary shaft disposed within the outer shell pipe for transmitting rotation of the tool rotating drive source within the drive unit housing to the spindle, and a hollow guide pipe provided within the outer shell pipe and extending to both end, in which case a pipe fixing segment is employed for fixedly connecting the outer shell pipe and the guide pipe with each other.

According to this construction, considering that the outer shell pipe and the guide pipe are connected with each other through the pipe fixing segment, the spindle guide section can have an increased section modulus, resulting in increase of the rigidity and, therefore, the spindle guide section will become hard to flex or bend even when a force acts on the distal end member and, also, the positioning accuracy of the distal end member relative to the drive unit housing can also be increased.

In the present invention, the flexible attitude altering member may be comprised of a plurality of force transmitting members arranged in a row. The force transmitting member may be employed in the form of balls or pillar shaped elements. If the attitude altering member is constituted by the plural force transmitting members arranged in a row within the guide hole, the flexibility as a whole can be obtained even though the individual force transmitting members are rigid elements.

In the present invention, the guide hole and the attitude altering member inserted within this guide hole may be provided at one location, in which case a restoring elastic member for urging the distal end member towards a predetermined attitude side is provided to enable the attitude altering member to alter the attitude of the distal end member against a biasing force of the restoring elastic member. Also, the guide hole and the attitude altering member inserted within this guide hole may be provided at two locations, in which case the attitude altering drive source is provided for each of those attitude altering members so that the attitude of the distal end member can be altered and maintained in dependence on the balance of respective working forces of the attitude altering members at the two locations acting on the distal end member. In either case, the attitude of the distal end member can be altered about a single attitude altering axis. Since in the latter case the distal end member is pressed by the two attitude altering members, the attitude stability of the distal end member can be increased as compared with that accomplished by the use of the only one attitude altering member.

In addition, the distal end member connecting unit may be of a type supporting the distal end member for tilting motion in any desired direction, in which case the guide hole and the attitude altering member inserted within this guide hole are provided at three or more locations about the center of tilt of the distal end member and the attitude altering drive source is provided for each of those attitude altering members so that the attitude of the distal end member can be altered and maintained in dependence on the balance of respective working forces of the attitude altering members at the three or more locations acting on the distal end member. In such case, the attitude of the distal end member can be altered about two attitude altering axes. In this construction, since the distal end member is pressed by the three or more attitude altering members, the attitude stability of the distal end member can be increased further.

In the present invention, the distal end member connecting unit is of a structure, in which where a guide member on the side of the spindle guide section and a guided member on the side of the distal end member contact each other on a spherical or cylindrical guide surface having a center of curvature lying on a center line of the spindle, a center of connection between the spindle and the rotary shaft lies at the same position as the center of curvature of the guide surface.

If the center of connection between the spindle and the rotary shaft lies at the same position as the center of curvature of the guide face, neither a pushing force nor a pulling force act on the rotary shaft upon alteration of the attitude of the distal end member and, therefore, the attitude of the distal end member can be smoothly altered.

In the present invention, the use may be made of an operating amount detector for detecting the amount of operation of the attitude altering drive source and an attitude detector for detecting the attitude of the distal end member from a detection value of the operating amount detector.

According to the above described construction, based on the result of detection performed by the attitude detector, a proper attitude control of the distal end member can be accomplished.

Where the attitude altering drive source is employed in the form of an electrically operated actuator, the use may be made of a load detector for detecting a load, acting on the distal end member, by measuring a supply power supplied to the electrically operated actuator.

According to the above described construction, when the amount of feed of the remote controlled actuator as a whole and the alteration of the attitude of the distal end member are controlled based on the result of detection performed by the load detector, cutting of the bone can be accomplished while the load acting on the distal end member is properly maintained.

In the present invention, the attitude altering drive source may be a linear actuator. In such case, a force increasing and transmitting mechanism comprised of a lever mechanism for force increasing an output of the linear actuator and transmitting it to the attitude altering member may be employed.

The use of the force increasing and transmitting mechanism is effective to apply a large force to the attitude altering member even with the linear actuator having a low output and, therefore, the linear actuator can be downsized to a compact structure.

In the present invention, the use may be made of a rotation preventing mechanism for preventing the distal end member from rotating about a center line of the distal end member relative to the spindle guide section.

According to the above described construction, since the use is made of the rotation preventing mechanism for preventing the distal end member from rotating about the center line thereof relative to the spindle guide section, even when the distal end member then holding the tool becomes uncontrollable as a result of any trouble occurring in the attitude altering drive mechanism for controlling the selective advance and retraction of the attitude altering member and/or the control device therefor, it is possible to avoid the possibility that the site to be processed may be impaired as a result of unexpected rotation of the distal end member about the center line or the distal end member 2 itself is broken.

In the present invention, the spindle guide section may include an outer shell pipe forming an outer shell for the spindle guide section, in which case the guide hole may be an inner diametric hole of a guide pipe provided within the outer shell pipe. According to this construction, while the interior of the spindle guide section is protected by the outer shell pipe, the spindle guide section can be made hollow and, therefore, the weight thereof can be reduced.

Where the above described construction is employed, the rotary shaft may be arranged at the center of the outer shell pipe and a plurality of reinforcement shafts so that the guide pipe can be arranged in a row in a circumferential direction between the rotary shaft and an inner diametric surface of the outer shell pipe. If the reinforcement shafts and the guide pipe are employed as described above, they can be arranged within the spindle guide section in a balanced fashion and the rigidity of the spindle guide section can therefore be increased.

If in the above described construction, a plurality of rolling bearings are provided for rotatably supporting the rotary shaft within the spindle guide section, the plural rolling bearings may have respective outer diametric surfaces supported by the plural reinforcement shafts and the guide pipe.

Also, where the use is made of a plurality of bearings for rotatably supporting the rotary shaft within the spindle guide section, a spring element may be employed for applying a preload to those rolling bearings, the spring element being provided between the neighboring rolling bearings.

In order to improve the processing finish, the spindle has to be rotated at a high speed. If the spindle is rotated at a high speed, an effect can also be appreciated that the cutting resistance to the tool can be reduced. Since the rotating force is transmitted to the spindle through the rotary shaft, made of a wire or the like, that is thin, the preload needs to be applied to the rolling bearings supporting the rotary shaft in order to realize a high speed rotation of the spindle. If the spring elements for applying the preload is provided between the neighboring rolling bearings, the spring element can be provided with no need to increase the diameter of the spindle guide section.

Where the use is made of the bearings for rotatably supporting the rotary shaft within the spindle guide section, a cooling unit for cooling the bearings with a liquid coolant flowing inside the outer shell pipe may be employed.

Rotatable members such as the spindle for rotating the tool and the rotary shaft evolve heat as a result of a rotation friction. This in turn results in heating of the bearings. If the cooling unit is provided, the bearings and the above described heat evolving site can be cooled with the liquid coolant. If the liquid coolant is allowed to flow through the interior of the outer shell pipe, there is no necessity to use any extra tube for the supply of the liquid coolant and, therefore, the spindle guide section can be simplified in structure and can have a reduced diameter.

In addition, an effect to lubricate the bearings with the liquid coolant can also be obtained. If the liquid coolant is concurrently used for lubricating the bearings, there is no need to use any grease or the like of a kind that is generally used in bearings and, yet, no lubricating device need not be employed.

Also, the cooling unit may be provided for cooling the tool with a liquid coolant flowing inside the outer shell pipe.

During the processing, the tool and/or an article to be processed emit heat. Accordingly, the use of the cooling unit is effective to cool the tool and the article to be processed with the liquid coolant.

The remote controlled actuator is designed for medical use, in which case it can be suitably used where the distal end member is inserted partly or in its entirety into a body of a patient.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

FIG. 1 is a diagram showing a schematic structure of a remote controlled actuator according to a first preferred embodiment of the present invention;

FIG. 2A is a longitudinal sectional view showing a distal end member of the remote controlled actuator and a spindle guide section thereof;

FIG. 2B is a cross sectional view taken along the line II-II in FIG. 2A;

FIG. 2C is a diagram showing a connecting structure between the distal end member and a rotary shaft;

FIG. 4 is a diagram showing a schematic structure when a cooling unit is provided in the remote controlled actuator;

FIG. 5A is a longitudinal sectional view showing the distal end member of the remote controlled actuator according to a second preferred embodiment of the present invention and the spindle guide section thereof;

FIG. 5B is a cross sectional view taken along the line V-V in FIG. 5A;

FIG. 6A is a longitudinal sectional view showing the distal end member of the remote controlled actuator according to a third preferred embodiment of the present invention and the spindle guide section thereof;

FIG. 6B is a cross sectional view taken along the line VI-VI in FIG. 6A;

FIG. 10A is a longitudinal sectional view showing the distal end member of the remote controlled actuator according to a fifth preferred embodiment of the present invention and the spindle guide section thereof;

FIG. 10B is a cross sectional view taken along the line X-X in FIG. 10A;

FIG. 10C is a diagram showing the connecting structure between the distal end member and the rotary shaft;

FIG. 12A is a longitudinal sectional view showing the distal end member of the remote controlled actuator and the spindle guide section thereof both employed in the remote controlled actuator according to a first modified form 1 of the fifth embodiment shown in FIGS. 10A to 10C and FIGS. 11A and 11B;

FIG. 12B is a cross sectional view taken along the line XII-XII in FIG. 12A;

FIG. 17A is a longitudinal sectional view showing the distal end member, the spindle guide section and a drive unit housing, all employed in the remote controlled actuator according to an eighth preferred embodiment of the present invention;

FIG. 17B is a cross sectional view taken along the line XVII-XVII in FIG. 17A;

FIG. 17C is a diagram showing the connecting structure between the distal end member and the rotary shaft;

FIG. 23A is a longitudinal sectional view showing the distal end member, the spindle guide section and the drive unit housing, all employed in the remote controlled actuator of a type employing a different attitude altering member;

FIG. 23B is a cross sectional view taken along the line XXIII-XXIII in FIG. 23A;

FIG. 24A is a longitudinal sectional view showing the distal end member, the spindle guide section and the drive unit housing, all employed in the remote controlled actuator of a type employing a further different attitude altering member;

FIG. 24B is a cross sectional view taken along the line XXIV-XXIV in FIG. 24A;

FIG. 25A is a longitudinal sectional view showing the distal end member and the spindle guide section both employed in the remote controlled actuator according to a ninth preferred embodiment of the present invention;

FIG. 25B is a cross sectional view taken along the line XXV-XXV in FIG. 25A;

FIG. 25C is a diagram showing the connecting structure between the distal end member and the rotary shaft;

FIG. 25D is a view showing a housing for the distal end member as viewed from the proximal end;

FIG. 29A is a longitudinal sectional view showing the distal end member and the spindle guide section both employed in the remote controlled actuator according to a thirteenth preferred embodiment of the present invention;

FIG. 29B is a cross sectional view taken along the line XXIX-XXIX in FIG. 29A;

FIG. 29C is a view showing the housing for the distal end member as viewed from the proximal end;

FIG. 30A is a longitudinal sectional view showing the distal end member and the spindle guide section both employed in the remote controlled actuator according to a fourteenth preferred embodiment of the present invention;

FIG. 30B is a cross sectional view taken along the line XXX-XXX in FIG. 30A;

FIG. 30C is a view showing the housing for the distal end member as viewed from the proximal end;

FIG. 32A is a longitudinal sectional view showing the distal end member and the spindle guide section both employed in the remote controlled actuator according to a fifteenth preferred embodiment of the present invention;

FIG. 32B is a top plan view of the distal end member and the spindle guide section shown in FIG. 33A;

FIG. 32C is a cross sectional view taken along the line XXXII-XXXII in FIG. 32A;

FIG. 32D is a view showing the housing for the distal end member as viewed from the proximal end;

FIG. 33A is a longitudinal sectional view showing the distal end member and the spindle guide section both employed in the remote controlled actuator according to a sixteenth preferred embodiment of the present invention;

FIG. 33B is a top plan view of the distal end member and the spindle guide section shown in FIG. 33A;

FIG. 33C is a cross sectional view taken along the line XXXIII-XXXIII in FIG. 33A;

FIG. 33D is a view showing the housing for the distal end member;

FIG. 37A is a longitudinal sectional view showing the distal end member and the spindle guide section both employed in the remote controlled actuator according to a twentieth preferred embodiment of the present invention;

FIG. 37B is a cross sectional view taken along the line XXXVII-XXXVII in FIG. 37;

FIG. 39A is a longitudinal sectional view showing the distal end member and the spindle guide section both employed in the remote controlled actuator according to a twenty second preferred embodiment of the present invention;

FIG. 39B is a cross sectional view taken along the line XXXIX-XXXIX in FIG. 39A;

FIG. 40A is a longitudinal sectional view showing the distal end member and the spindle guide section both employed in the remote controlled actuator according to a twenty third preferred embodiment of the present invention;

FIG. 40B is a cross sectional view taken along the line XXXX-XXXX in FIG. 40A;

DESCRIPTION OF THE PREFERRED EMBODIMENTS

Figure 3A:
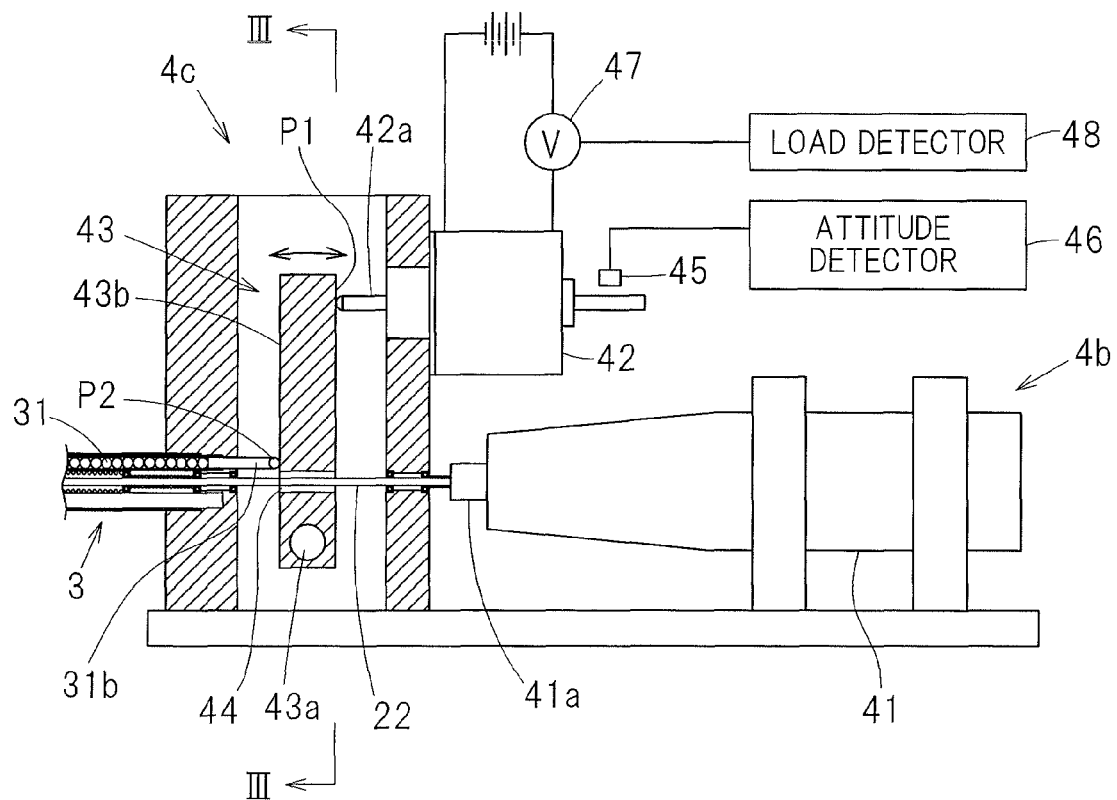
FIG. 3A is a diagram showing a side view, illustrative of a tool rotating drive mechanism of the remote controlled actuator and an attitude altering drive mechanism, together with a control system.

A first preferred embodiment of the present invention will now be described with particular reference to FIG. 1 to FIGS. 3A and 3B. Referring to FIG. 1, a remote controlled actuator according to the first embodiment of the present invention includes a distal end member 2 for holding a rotary tool 1, an elongated spindle guide section 3 having a distal end to which the distal end member 2 is coupled for displacement in attitude, a drive unit housing 4a to which a proximal end of the spindle guide section 3 is coupled, and a controller 5 for controlling a tool rotating drive mechanism 4b and an attitude altering drive mechanism 4c, both accommodated within the drive unit housing 4a. The drive unit housing 4a cooperates with the built-in tool rotating drive mechanism 4b and attitude altering drive mechanism 4c to form a drive unit 4.

As best shown in FIGS. 2A to 2C, the distal end member 2 includes a generally or substantially cylindrical housing 11 and a spindle 13 rotatably accommodated within such cylindrical housing 11 through a pair of bearings 12. The spindle 13 is of a tubular shape having a distal side opening and having a hollow defined therein, and a tool 1 is drivingly coupled with the spindle 13. Specifically, a shank portion 1a of the tool 1 is inserted into the hollow of the spindle 13 and is then coupled with such spindle 13 by means of a stop pin 14 for rotation together with the spindle 13. The distal end member 2 of the structure described above is coupled with a distal end of the spindle guide section 3 through a distal end member coupling unit 15. The distal end member coupling unit 15 is means for supporting the distal end member 2 for displacement in attitude and is comprised of a spherical bearing. More specifically, the distal end member coupling unit 15 includes a guided member 11a in the form of an inner diameter reduced portion at a base end of the housing 11, and a guide member 21a in the form of a collar integral with a constraint member 21 fixed to the tip of the spindle guide section 3. The guided member 11a and the guide member 21a have respective guide faces F1 and F2 that are held in sliding contact with each other, and those guide faces F1 and F2 have respective centers of curvature lying at a point O on the center line or longitudinal axis CL of the spindle 13, having their diameters being reduced towards the base end of the spindle 13. Accordingly, not only can the distal end member 2 be immovably constrained relative to the spindle guide section 3, but it can also be supported for displacement in attitude so that the attitude of the distal end member 2 can be altered. It is to be noted that since in this example, the distal end member 2 can have its attitude altered about a lateral X-axis passing through the center of curvature O, the guide faces F1 and F2 may be a cylindrical surface having a longitudinal axis represented by the X-axis passing through the point O.

Figure 3B:
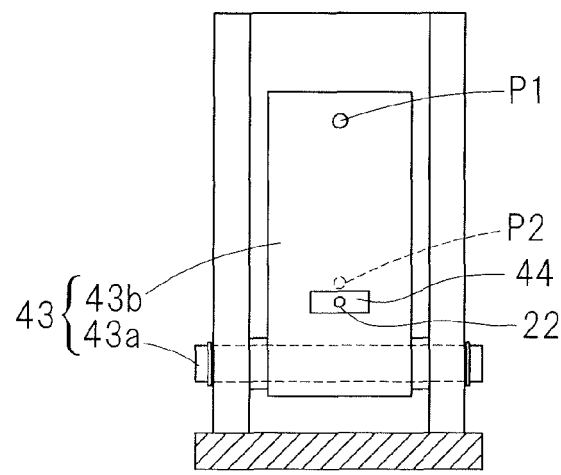
FIG. 3B is a cross sectional view taken along the line in FIG. 3A.

The spindle guide section 3 includes a rotary shaft 22 for transmitting a rotational force exerted by a tool rotating drive source 41 accommodated within the drive unit housing 4a (FIGS. 3A and 3B). In the illustrated example, the rotary shaft 22 is employed in the form of a wire capable of undergoing deformation to a certain extent. Material for the wire includes, for example, metal, resin or glass fiber. The wire may be either a single wire or a stranded wire. As best shown in FIG. 2C, the spindle 13 and the rotary shaft 22 are connected together by means of an universal joint 23 for transmitting rotation from the rotary shaft 22 to the spindle 13. The universal joint 23 is made up of a groove 13a, defined in a closed base end of the spindle 13, a projection 22a defined in a distal end of the rotary shaft 22 and engageable in the groove 13a. The center of joint between the groove 13a and the projection 22a is located at the same position as the centers of curvature O of the guide faces F1 and F2. It is, however, to be noted that the rotary shaft 22 and the projection 22a may be formed of members separate from each other.

The spindle guide section 3 includes an outer shell pipe 25 forming an outer shell of the spindle guide section 3 and the rotary shaft 22 referred to above is positioned at the center of this outer shell pipe 25. The rotary shaft 22 so positioned is rotatably supported by a plurality of rolling bearings 26 positioned spaced a distant apart from each other in a direction axially of the spindle guide section 3. Spring elements 27A and 27B for generating a preload on the corresponding rolling bearing 26 are disposed between the neighboring rolling bearings 26. Each of those spring elements 27A and 27B is employed in the form of, for example, a compression spring. There are the spring element 27A for inner ring for generating the preload on the inner ring of the rolling bearing 26 and the spring element 27B for outer ring for generating the preload on the outer ring of the rolling bearing 26, and the both are arranged alternately relative to each other. The constraint member 21 referred to previously is fixed to a pipe end portion 25a of the outer shell pipe 25 by means of a fixing pin 28 and has its distal end inner peripheral portion supporting the distal end of the rotary shaft 22 through a rolling bearing 29. It is, however, to be noted that the pipe end portion 25a may be a member separate from the outer shell pipe 25 and may then be connected with the outer shell pipe 25 by means of, for example, welding.

A single guide pipe 30 open at opposite ends thereof is provided between an inner diametric surface of the outer shell pipe 25 and the rotary shaft 22, and an attitude altering member 31, made up of a plurality of balls 31a and pillar shaped pins 31b at opposite ends, both of which serve as a force transmitting member, is axially movably inserted within a guide hole 30a, which is an inner diametric hole of the guide pipe 30. The balls 31a and the pillar shaped pins 31b are arranged in a row in line with each other in a direction lengthwise of the guide hole 30a with no gap formed between those elements. One of the pillar shaped pins 31b, which is on the side of the distal end member 2, has its tip representing a spherical shape and is held in contact with a base end face of the distal end member housing 11. Similarly, the other of the pillar shaped pins 31b, that is, the pillar shaped pin 31b on the side of the drive unit housing 4a has its tip representing a spherical shape and held in contact with a side face of a lever 43 (FIGS. 3A and 3B) as will be described in detail later.

At a position spaced 180° in phase from a peripheral position where the attitude altering member 31 referred to above is positioned, a restoring elastic member 32, which is in the form of, for example, a compression spring, is provided between the base end face of the housing 11 for the distal end member 2 and a tip end face of the outer shell pipe 25 of the spindle guide section 3. This restoring elastic member 32 has a function of biasing the distal end member 2 towards the side of a predetermined attitude.

Also, between the inner diametric surface of the outer shell pipe 25 and the rotary shaft 2, a plurality of reinforcement shafts 34 are arranged separate from the guide pipe 30 and on the pitch circle C of the same diameter as the guide pipe 30. Those reinforcement shafts 34 are used to secure the rigidity of the spindle guide section 3. The guide pipe 30 and the reinforcement shafts 34 are arranged equidistantly relative to each other around the rotary shaft 22. The guide pipe 30 and the reinforcement shafts 34 are held in contact with the inner diametric surface of the outer shell pipe 25 and respective outer peripheral surfaces of the rolling bearings 26. In this manner, the outer diametric surfaces of those rolling bearings 26 are supported.

The tool rotating drive mechanism 4b and the attitude altering drive mechanism 4c, both housed within the drive unit housing 4a, are best shown in FIGS. 3A and 3B. The tool rotating drive mechanism 4b makes use of a tool rotating drive source 41 that is controlled by the controller 5. This tool rotating drive source 41 is in the form of, for example, an electric motor, having its output shaft 41a coupled with a base end or proximal end of the rotary shaft 22. The attitude altering drive mechanism 4c makes use of an attitude altering drive source 42 that is controlled by the controller 5. This attitude altering drive source 42 is in the form of, for example, an electrically operated linear actuator having an output rod 42a, the movement of the output rod 42a in one of leftward and rightward directions one at a time being transmitted to the attitude altering member 31 through a force increasing and transmitting mechanism 43. The force increasing and transmitting mechanism 43 includes a pivot lever 43b pivotable about a support pin 43a and is so designed and so configured as to allow a force of the output rod 42a to work on a working point P1 of the lever 43b, which is spaced a long distance from the support pin 43a, and as to apply a force to the attitude altering member 31 at a force point P2, which is spaced a short distance from the support axis 43a, wherefore an output of the attitude altering drive source 42 can be increased and then transmitted to the attitude altering member 31. Since the use of the force increasing and transmitting mechanism 43 is effective to enable a large force to be applied to the attitude altering member 31 even in the linear actuator of a low output capability, the linear actuator can be downsized. The rotary shaft 22 extends through an opening 44 defined in the pivot lever 43b. It is to be noted that instead of the use of the attitude altering drive source 42 or the like, the attitude of the distal end member 2 may be manually operated from a remote site (by remote control).

The attitude altering drive mechanism 4c is provided with an operating amount detector 45 for detecting the operating amount of the attitude altering drive source 42. A detection value outputted from this operating amount detector 45 is outputted to an attitude detector 46. The attitude detector 46 is operable to detect the attitude inclined about the X-axis (FIGS. 2A and 2B) of the distal end member 2, that is, to detect the attitude of the distal end member 2 that has been inclined about the X-axis. The attitude detector 46 includes a relation setting means (not shown), in which the relation between the output signal of the operating amount detector 45 and the attitude of the distal end member 2 inclined is set in terms of an arithmetic equation or table, and makes use of the relation setting means to detect the inclination in attitude in reference to the output signal inputted. This attitude detector 46 may be provided either in the controller 5 or in an external control device.

Also, the attitude altering drive mechanism 4c is provided with a supply power meter 47 for detecting the electric energy supplied to the attitude altering drive source 42, which is an electrically operated actuator. A detection value of this supply power meter 47 is outputted to a load detector 48. This load detector 48 in turn detects a load acting on the distal end member 2 in reference to an output of the supply power meter 47. This load detector 48 includes a relation setting means (not shown), in which the relation between the load and the output signal of the supply power meter 47 is set in terms of an arithmetic equation or table, and makes use of the relation setting means to detect the load in reference to the output signal so inputted. This load detector 48 may be provided either in the controller 5 or in an external control device.

The controller 5 referred to above is operable to control the tool rotation drive source 41 and the attitude altering drive source 42, based on the respective detection values outputted by the attitude detector 46 and the load detector 48.

The operation of the remote controlled actuator of the construction hereinabove described will now be described in detail.

When the tool rotating drive source 41 is driven, the rotational force thereof is transmitted to the spindle 13 through the rotary shaft 22 to thereby rotate the tool 1 together with the spindle 13. The load acting on the distal end member 2 when the tool 1 then being rotated cuts a bone or the like is detected from the detection value of the supply power meter 47 by the load detector 48. Accordingly, when the amount of feed of the remote controlled actuator in its entirety and the alteration of attitude of the distal end member 2, as will be described later, are controlled in dependence on the value of the load detected in the manner described above, cutting of the bone with the load acting on the distal end member 2 can be properly carried out while the load acting on the distal end member 2 is maintained properly.

During the use, the attitude altering drive source 42 is driven to alter the attitude of the distal end member 2 by remote control. By way of example, if the attitude altering member 31 is advanced by the attitude altering drive source 42 in a direction towards the tip or distal side, the housing 11 for the distal end member 2 is pressed by the attitude altering member 31 with the distal end member 2 consequently altered in attitude along the guide faces F1 and F2 so that the tip or distal side can be oriented downwardly as viewed in FIG. 2A. If the attitude altering member 31 is conversely retracted by the attitude altering drive source 42, the housing 11 for the distal end member 2 is pressed backwardly by the effect of the elastic repulsive force exerted by the restoring elastic member 32 and, consequently, the distal end member 2 is altered in attitude along the guide faces F1 and F2 so that the tip or distal side can be oriented upwardly as viewed in FIG. 2A. At this time, a pressure from the attitude altering member 31, the elastic repulsive force from the restoring elastic member 32 and a reactive force from the constraint member 21 are applied to the distal end member coupling unit 15 and, depending on the balance of those applied forces, the attitude of the distal end member 2 is determined. The attitude of the distal end member 2 is detected by the attitude detector 46 from the detection value of the operating amount detector 45. For this reason, the attitude of the distal end member 2 can be properly controlled by remote control.

Since the attitude altering member 31 is inserted through the guide hole 30a, the attitude altering member 31 can properly act on the distal end member 2 at all times without being accompanied by displacement in position in a direction perpendicular to the lengthwise direction thereof and the attitude altering operation of the distal end member 2 can therefore be performed accurately. Also, since the attitude altering member 31 is made up of the plural balls 31a and the pillar shaped pins 31b and has a flexible property in its entirety, the attitude altering operation of the distal end member 2 is carried out accurately even though the spindle guide section 3 is curved. In addition, since the center of the junction between the spindle 13 and the rotary shaft 22 lies at the same position as the respective centers of curvature O of the guide faces F1 and F2, no force tending to press and pull will not act on the rotary shaft 22 as a result of the alteration of the attitude of the distal end member 2 and the distal end member 2 can be smoothly altered in attitude.

The remote controlled actuator of the foregoing construction is utilized in grinding the femoral marrow cavity during, for example, the artificial joint replacement surgery and during the surgery, it is used with the distal end member 2 in its entirety or a part thereof inserted into the body of a patient. Because of this, if the distal end member 2 can be altered in attitude by remote control, the bone can be processed in a condition with the tool 1 maintained in a proper attitude at all times and the opening for insertion of the artificial joint can be finished accurately and precisely.

There is the necessity that the rotary shaft 22 and the attitude altering member 31 are provided in a protected fashion. In this respect the spindle guide section 3, which is elongated in shape, is provided with the rotary shaft 22 at the center of the outer shell pipe 25 and the guide pipe 30, accommodating therein the attitude altering member 31, and the reinforcement shafts 34, all of these are arranged in the circumferential direction and between the outer shell pipe 25 and the rotary shaft 22. Accordingly, the rotary shaft 22 and the attitude altering member 31 can be protected and the interior can be made hollow to thereby reduce the weight without sacrificing the rigidity. Also, the arrangement balance as a whole is rendered good.

Since the outer diametric surfaces of the rolling bearings 26 supporting the rotary shaft 22 are supported by the guide pipe 30 and the reinforcement shafts 34, the outer diametric surfaces of the rolling bearings 26 can be supported with no need to use any extra member. Also, since the preload is applied to the rolling bearings 26 by means of the spring elements 27A and 27B, the rotary shaft 22 comprised of the wire can be rotated at a high speed. Because of that, the processing can be accomplished with the spindle 13 rotated at a high speed and a good finish of the processing can also be obtained and the cutting resistance acting on the tool 1 can be reduced. Since the spring elements 27A and 27B are disposed between the neighboring rolling bearings 26, the spring elements 27A and 27B can be provided with no need to increase the diameter of the spindle guide section 3.

According to the foregoing embodiment, the tool rotating drive source 41 and the attitude altering drive source 42 are accommodated within the common drive unit housing 4a. Because of that, the entire structure of the remote controlled actuator can be simplified. It is, however, to be noted that only one of the tool rotating drive source 41 and the attitude altering drive source 42 may be accommodated within the drive unit housing 4a. Also, as will be described later, both of the tool rotating drive source 41 and the attitude altering drive source 42 may be provided outside the drive unit housing 4a.

In view of the spindle guide section 3 being of a hollow shape, the remote controlled actuator of the present invention can be provided with a cooling unit 50 for cooling the tool 1 as shown in FIG. 4. In other words, the cooling unit 50 includes a liquid coolant supply device 51, provided outside the drive unit housing 4a, and a liquid coolant supply tube 52 for guiding a liquid coolant from the liquid coolant supply device 51 towards the tool 1 through the drive unit housing 4a, the spindle guide section 3 and the interior of the distal end member 2. A portion 52a of the liquid coolant supply tube 52, which extends within the spindle guide section 3, is constituted by the outer shell pipe 25 itself serving as the liquid coolant supply tube 52 and the liquid coolant flows through an interior of the outer shell pipe 25 accordingly. The liquid coolant guided to the tool 1 is discharged to an outer periphery of the tool 1. If the cooling unit 50 is provided in this way, heat emitting areas such as, for example, the tool 1, a to-be-processed article, the spindle 13, the rotary shaft 22 and the bearings 26 and 29 can be cooled. Since the liquid coolant is passed through the outer shell pipe 25, there is no need to use any extra tube for the purpose of supplying the liquid coolant and the spindle guide section 3 can therefore be simplified and made small in diameter. Also, the liquid coolant may be concurrently used for lubrication of the rolling bearings 26 and 29. By so doing, the use of a grease or the like, which is generally used, can be dispensed with and, also, there is no need to use any extra lubricating device. It is to be noted that a liquid coolant recirculating system may be designed, in which the liquid coolant once guided to the tool 1 is returned to the liquid coolant supply device 51 without being discharged to the outer periphery of the tool 1. It is, however, noted that where the flow of the liquid coolant passing through the outer shell pipe 25 is small, an extra liquid coolant has to be supplied from the outside to cool the tool 1 and the to-be-processed article.

The liquid coolant referred to above is preferably in the form of water or physiological saline. If the liquid coolant is employed in the form of water or physiological saline, the liquid coolant will bring no adverse influence on the living body when the processing is performed with the distal end member 2 inserted into the living body. Where water or physiological saline is employed for the liquid coolant, component parts, with which the liquid coolant contacts, are preferably made of stainless steel that is excellent in resistance to corrosion. Any other component parts forming the remote controlled actuator may be made of stainless steel.

FIGS. 5A and 5B illustrate a second preferred embodiment of the present invention. The remote controlled actuator according to this second embodiment is of a design, in which the two guide pipes 30 are provided at the peripheral positions spaced 180° in phase from each other within the outer shell pipe 25 and the attitude altering member 31 is reciprocally movably inserted within guide holes 30a, which are inner diametric holes of the guide pipes 30. Between those two guide pipes 30, a plurality of reinforcement shafts 34 are arranged on the same pitch circle as that of the guide pipes 30. No restoring elastic member 32 is provided. The guide faces F1 and F2 are spherical surfaces each having the center of curvature lying at the point O or cylindrical surfaces each having a lateral X-axis as a longitudinal axis passing through the point O.

The drive unit 4 (not shown in FIG. 5A or 5B) is provided with two attitude altering drive sources 42 (not shown in FIG. 5A or 5B) for selectively advancing and retracting respective attitude altering members 31 so that when those two attitude altering drive sources 42 are driven in respective directions opposite to each other, the distal end member 2 can be altered in attitude. By way of example, when the upper attitude altering member 31 shown in FIGS. 5A and 5B is advanced towards the tip end side and the lower attitude altering member 31 is retracted, the housing 11 for the distal end member 2 is pressed by the upper attitude altering member 31 and, therefore, the distal end member 2 is altered in attitude along the guide surfaces F1 and F2 with the tip end side oriented downwards as viewed in FIG. 5A.

Conversely, when both of the attitude altering members 31 are driven in the directions opposite thereto, the lower attitude altering member 31 urges the housing 11 for the distal end member 2 to allow the distal end member 2 to alter in attitude along the guide surfaces F1 and F2 with the distal end side oriented upwardly as viewed in FIG. 5A. At this time, the pressures from the upper and lower attitude altering members 31 and a reactive force from the constraint member 21 act on the distal end member connecting unit 15 and, accordingly, the attitude of the distal end member 2 is determined in dependence on the balance of those working forces. According to this construction, since the housing 11 for the distal end member 2 is pressed by the two attitude altering members 31, as compared with the previously described embodiment in which it is pressed by the only attitude altering member 31, the attitude stability of the distal end member 2 can be increased.

FIGS. 6A and 6B illustrates a third preferred embodiment of the present invention. The remote controlled actuator according to this third embodiment makes use of three guide pipes 30 disposed within the outer shell pipe 25 and positioned at respective circumferential position spaced 120° in phase from each other within the outer shell pipe 25 and, correspondingly, three attitude altering members 31 accommodated within respective guide holes 30a, which are inner diametric holes of those guide pipes 30, for reciprocal movement relative to the associated guide pipes 30. Between the three guide pipes 30, a plurality of reinforcement shafts 34 are arranged on the same pitch circle as that of the guide pipes 30. No restoring elastic member 32 is provided. The guide surfaces F1 and F2 represents spherical surface having respective centers of curvature lying at the point O and the distal end member 2 can be tilted in any desired direction.

The drive unit 4 is provided with three attitude altering drive sources 42 (42U, 42L and 42R) (FIG. 8) for reciprocally operating respective attitude altering members 31 (31U, 31L and 31R), and those attitude altering drive sources 42 cooperate with each other to drive the distal end member 2 to alter the attitude thereof.

By way of example, when one of the attitude altering members 31U, which is shown in an upper side of FIGS. 6A and 6B, is advanced towards the tip end side while the other two attitude altering members 31L and 31R are retracted, the housing 11 for the distal end member 2 is pressed by the attitude altering member 31U shown in the upper side of FIGS. 6A and 6B to allow the distal end member 2 to be altered in attitude along the guide surfaces F1 and F2 with the tip end side consequently oriented downwardly as viewed in FIG. 6A. At this time, those attitude altering drive sources 42 are controlled so that the amount of advance or retraction of each of the attitude altering members 31 may become proper. On the other hand, when each of those attitude altering members 31 is conversely retracted or advanced, the housing 11 for the distal end member 2 is pressed by the attitude altering members 31L and 31R, which are shown on lower left and lower right sides, and, consequently, the distal end member 2 is altered in attitude along the guide surfaces F1 and F2 with the tip end side oriented upwardly as viewed in FIG. 6A.

Also, when while the attitude altering member 31U on the upper side is held still, the attitude altering member 31L on the left side is advanced towards the tip end side and the attitude altering member 31R on the right side is retracted, the housing 11 for the distal end member 2 is pressed by the attitude altering member 31L on the left side to allow the distal end member 2 to be oriented rightwards, that is, to be altered in attitude along the guide surfaces F1 and F2 with the distal end member 2 oriented towards a rear side of the sheet of the drawing of FIG. 6A. Conversely, when the attitude altering members 31L and 31R on the left and right sides are advanced and retracted, the housing 11 for the distal end member 2 is pressed by the attitude altering member 31R on the right side, allowing the distal end member 2 to be altered in attitude so that the distal end member 2 can be guided along the guide surfaces F1 and F2 so as to be oriented leftwards.

The use of the attitude altering members 31 at the three circumferential locations as hereinabove described is effective to allow the distal end member 2 to be altered in attitude in two axis directions (X-axis and Y-axis directions) upwardly or downwardly and leftwards or rightwards. At this time, respective pressures from the three attitude altering members 31 and the reactive force from the constraint member 21 act on the distal end member connecting unit 15 and, therefore, the attitude of the distal end member 2 is determined in dependence on the balance of those working forces. According to the above described construction, since the housing 11 for the distal end member 2 is pressed by the three attitude altering members 31, the attitude stability of the distal end member 2 can be further increased. It is, however, to be noted that if the number of the attitude altering members 31 used is increased, the attitude stability of the distal end member 2 can be still further increased.

Figure 7A:
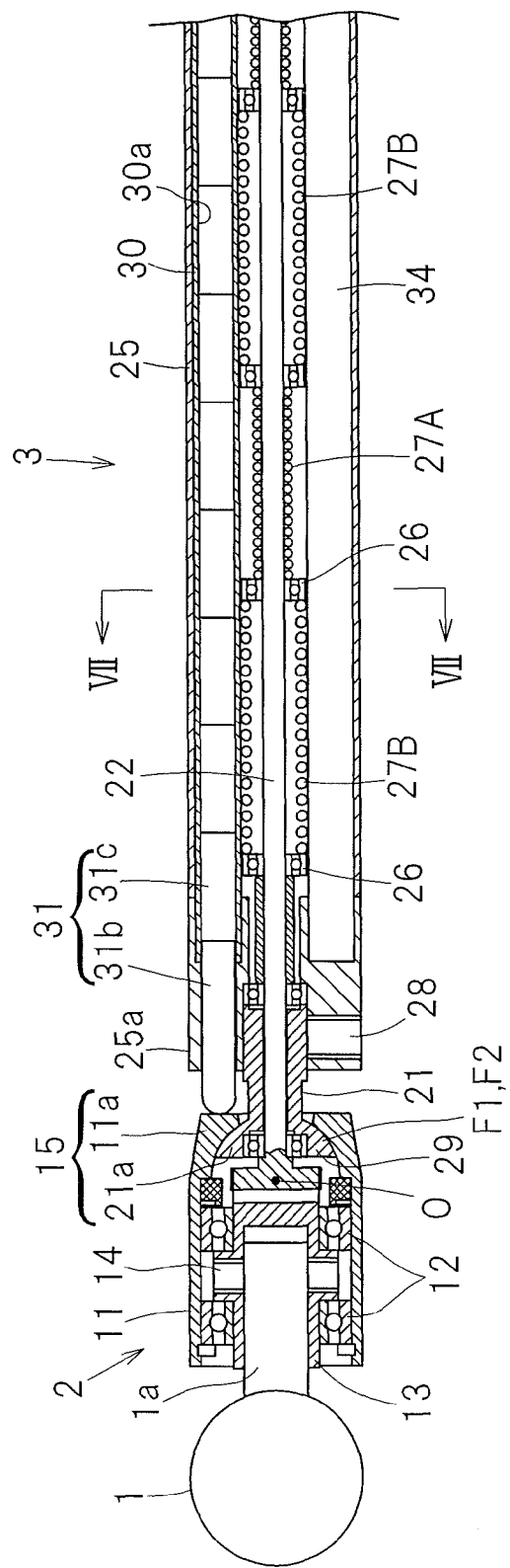
FIG. 7A is a longitudinal sectional view showing the distal end member of the remote controlled actuator according to a fourth preferred embodiment of the present invention and the spindle guide section thereof.
Figure 7B:
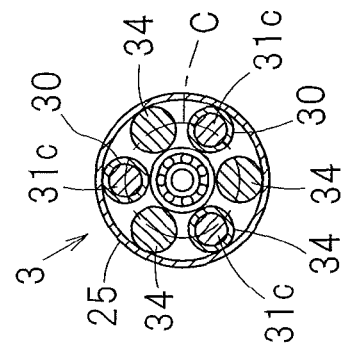
FIG. 7B is a cross sectional view taken along the line VII-VII in FIG. 7A.

A fourth preferred embodiment of the present invention is shown in FIGS. 7A and 7B. The remote controlled actuator according to this fourth embodiment is of a structure, in which the force transmitting member of the attitude altering member 31 is employed in the form of pillar shaped elements 31c such as, for example, cylinders. The pillar shaped elements 31c and the pillar shaped pins 31b at both ends thereof are arranged in a lengthwise direction of the guide hole 30a with no gap formed between the neighboring members. The fourth embodiment is directed to the example, in which the attitude altering members 31 are arranged at three locations spaced 120° in phase from each other in the circumferential direction, but the present invention is equally applicable to the arrangement, in which the attitude altering members 31 are arranged at two locations spaced 180° in phase from each other in the circumferential direction, and the example in which the use is made of one attitude altering member 31, arranged at one circumferential location, in combination with the corresponding restoring elastic member 32.

Figure 8:
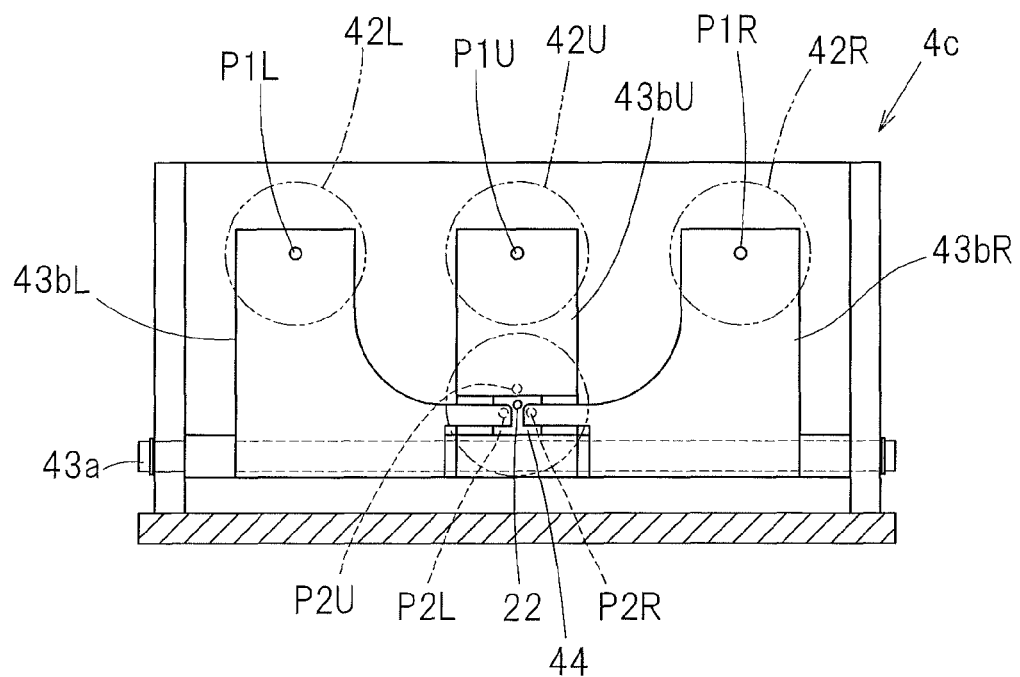
FIG. 8 is a partially cutout front elevational view showing the tool rotating drive mechanism and the attitude altering drive mechanism both employed in the remote controlled actuator shown in FIGS. 6A and 6B and FIGS. 7A and 7B.

Even in the case where the force transmitting member is constituted by the pillar shaped elements 31c, as is the case with the force transmitting member constituted by the balls 31a, when the attitude altering drive source 42 is driven, the attitude altering members 31 can be advanced or retracted to work on the distal end member 2. Even when the force transmitting member is constituted by the pillar shaped elements 31c, the distal end member 2 can be properly operated at all times with no displacement in position taking place in a direction transverse to the longitudinal direction of the attitude altering member 31. Also, it has a flexibility and, therefore, even when it is provided in the spindle guide section of a curved configuration, the attitude altering operation of the distal end member 2 can be properly performed. Where the force transmitting member is constituted by the pillar shaped elements 31c, as compared with the balls 31a, there is an advantage that the rigidity of the spindle guide section 3 can be increased. It is, however, to be noted that the attitude altering member 31 may be constituted by both the pillar shaped elements 31c and the balls 31a.

Where the attitude altering members 31 are provided at the three circumferential locations such as in any one of the embodiments shown and described with reference to FIGS. 6A and 6B and FIGS. 7A and 7B, the attitude altering drive mechanism 4c may be constructed, for example, such as shown in FIG. 8. In other words, the attitude altering drive mechanism 4c is so constructed that the three attitude altering drive sources 42 (42U, 42L and 42R) for selectively advancing and retracting the attitude altering members 31 (31U, 31L and 31R) may be arranged along a leftward and rightward direction and parallel to each other. Levers 43b (43bU, 43bL and 43bR) corresponding to the attitude altering drive sources 42 may be provided for pivotal movement about a common support pin 43a to enable the force of the output rod 42a (FIG. 3) of each of the attitude altering drive sources 42 to work on the point P1 (P1U, P1L and P1R) of the respective lever 43b, which is spaced a long distance from the support pin 43a, and to enable the force to work on the attitude altering member 31 at the point P2 (P2U, P2L and P2R), which is spaced a short distance from the support pin 43a. Accordingly, the output of each of the attitude altering drive sources 42 can be increased and then transmitted to the corresponding attitude altering member 31. It is to be noted that the rotary shaft 22 is passed through an opening 44 defined in the lever 43bU for the attitude altering member 31U on the upper side.

Figure 9:
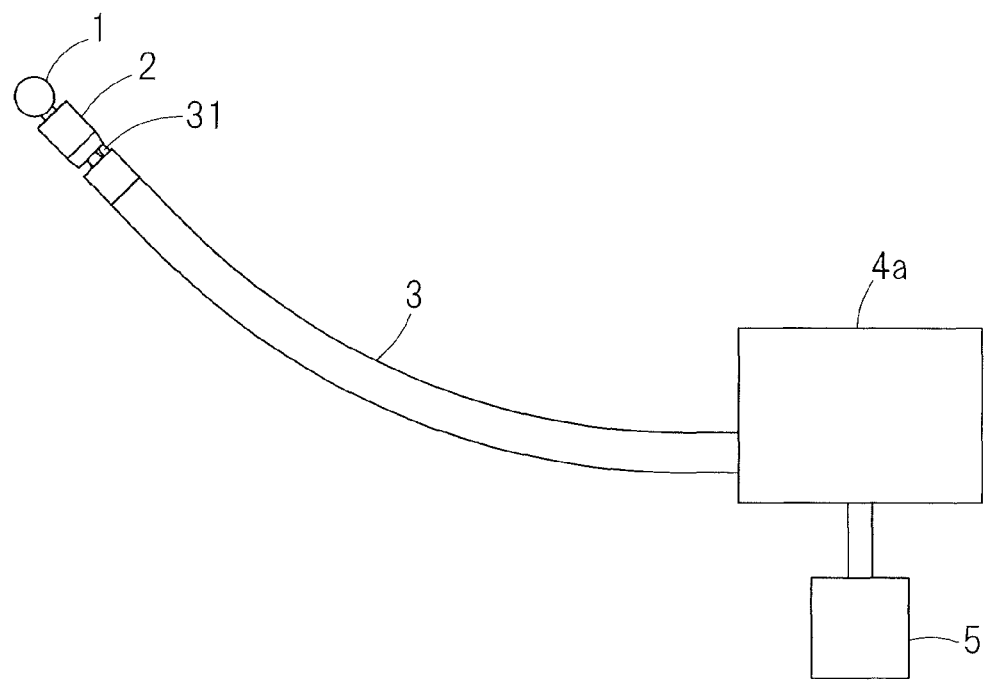
FIG. 9 is a diagram showing a schematic structure of the remote controlled actuator employing the spindle guide section of a different configuration.

While in any one of the foregoing embodiments the spindle guide section 3 has been shown and described as extending straight, since the remote controlled actuator of the present invention is such that the attitude altering member 31 has a flexibility and, even when the spindle guide section 3 is curved, the attitude alteration of the distal end member 2 takes place assuredly, the spindle guide section may have a curved shape in an initial condition as shown in FIG. 9. Alternatively, only a portion of the spindle guide section 3 may have a curved shape. If the spindle guide section 3 has a curved shape, it may happen that insertion of the distal end member 2 deep into the bore, where the spindle guide section of the straight shape fails to reach, can be accomplished, and, therefore, the processing of the opening for insertion of the artificial joint prior to a surgery being performed to replace with the artificial joint can be formed precisely and accurately.

Where the spindle guide section 3 is designed to represent the curved shape, the outer shell pipe 25, the guide pipes 30 and the reinforcement shafts 34 need be curved in shape. Also, an easily deformable material is preferably used for the rotary shaft 22 and a shape memory alloy, for example, can be suitably employed therefor. Other than the plural balls, the attitude altering member 31 may be comprised of a plurality of pillar shaped elements so curved as to follow the curvature of the guide pipes 30. In such case, the pillar shaped element so curved is preferably of a shape short in length and having corners chamfered.

A fifth preferred embodiment of the present invention will now be described in detail with particular reference to FIGS. 10A to 10C and FIGS. 11A and 11B. FIGS. 10A to 10C and FIGS. 11A and 11B correspond to FIGS. 2A to 2C and 3A and 3B showing the first embodiment of the present invention and component parts shown therein and similar to those employed in the first embodiments are designated by like reference numerals and, therefore, the details thereof are not reiterated for the sake of brevity.

According to the fifth embodiment, whereas in the previously described first embodiment the plural balls 31a and the pillar shaped pins 31b at both ends thereof, which altogether form the force transmitting member, are reciprocally movably inserted within the guide hole 30a, which is an inner diametric hole in the guide pipe 30, the attitude altering wire 31a is reciprocally movably inserted within the guide hole 30a. In this embodiment, the attitude altering wire 31a and the pillar shaped pins 31b cooperate with each to define the attitude altering member 31. Other structural features than those described above are similar to those shown and described in connection with the previously described first embodiment.

Figure 11A:
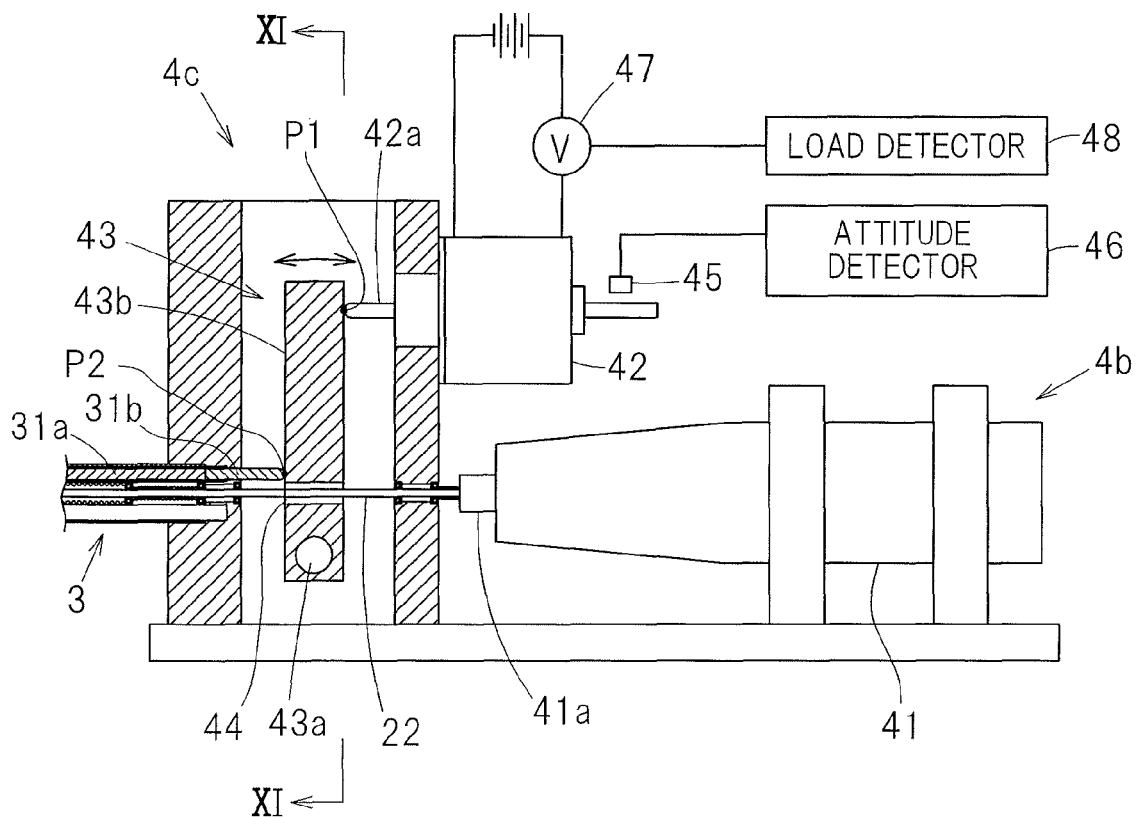
FIG. 11A is a diagram showing a side view, illustrative of a tool rotating drive mechanism of the remote controlled actuator and an attitude altering drive mechanism, together with a control system, in the fifth preferred embodiment of the present invention.
Figure 11B:
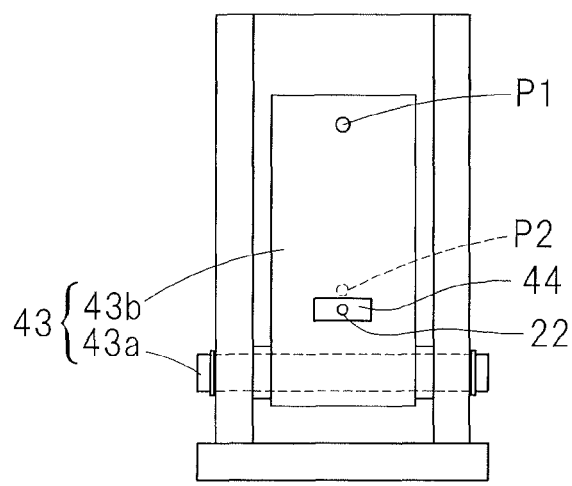
FIG. 11B is a cross sectional view taken along the line XI-XI in FIG. 11A.

FIGS. 11A and 11B illustrate the tool rotating drive mechanism 4b and the attitude altering drive mechanism 4c both accommodated within the drive unit housing 4a. The tool rotating drive source 4b includes a tool rotating drive source 41 that is controlled by the controller 5. This tool rotating drive source 41 is employed in the form of, for example, an electric motor having an output shaft 41a coupled with the base end or proximal end of the rotary shaft 22. On the other hand, the attitude altering drive mechanism 4c includes an attitude altering drive source 42 that is controlled by the controller 5. This attitude altering drive source 42 is employed in the form of, for example, an electrically operated linear actuator having an output rod 42a movable in one of leftward and rightward directions one at a time as viewed in FIG. 11A, the movement of such output rod 42a being transmitted to the attitude altering member 31 through a force increasing and transmitting mechanism 43. The force increasing and transmitting mechanism 43 includes a pivot lever 43b pivotable about a support pin 43a and is so designed and so configured as to allow a force of the output rod 42a work on a force point P1 of the lever 43b, which is spaced a long distance from the pivot pin 43a, and as to apply a force to the attitude altering member 31 at a force point P2 which is spaced a short distance from the support pin 43a, wherefore the output from the attitude altering drive source 42 can be increased and then transmitted to the attitude altering member 31. Since the use of the force increasing and transmitting mechanism 43 is effective to enable the linear actuator, capable of providing a low output, to apply a large force to the attitude altering wire 31a, the linear actuator can be downsized. It is to be noted that the rotary shaft 22 extends through an opening 44 defined in the pivot lever 43b. It is also to be noted that instead of the use of the attitude altering drive source 42 or the like, the attitude of the distal end member 2 may be manually operated from a remote site (by remote control).

Since the operation of the remote controlled actuator according to the fifth embodiment is similar to that according to the previously described first embodiment, the details thereof are not reiterated for the sake of brevity.

Even in the case of this fifth embodiment described above, since the attitude altering wire 31a forming a part of the attitude altering member 31 is flexible, the attitude alteration of the distal end member 2 can be accomplished assuredly even when the spindle guide section 3 has a curved portion.

In this fifth embodiment described above, the tool rotating drive source 41 and the attitude altering drive source 42 are provided within the common drive unit housing 4a. Because of this, the structure of the remote controlled actuator as a whole can be simplified. It is, however, to be noted that only one of the tool rotating drive source 41 and the attitude altering drive source 42 may be provided within the drive unit housing 4a. It is also to be noted that as will be described later, both of the tool rotating drive source 41 and the attitude altering drive source 42 may be provided outside the drive unit housing 4a.

Although in the fifth embodiment described above, the attitude altering member 31 has been shown and described as comprised of the attitude altering wire 31a and the pillar shaped pins 31b at both ends thereof, the attitude altering member 31 may be constituted solely of the attitude altering wire 31a, with no pillar shaped pin 31b employed, so that the housing 11 can be directly pressed by a tip end of the attitude altering wire 31a as shown in FIGS. 12A and 12B in connection with a first modified form 1 of the fifth embodiment. In such case, the tip end of the attitude altering wire 31a is preferred to represent a spherical surface.

Figure 13A:
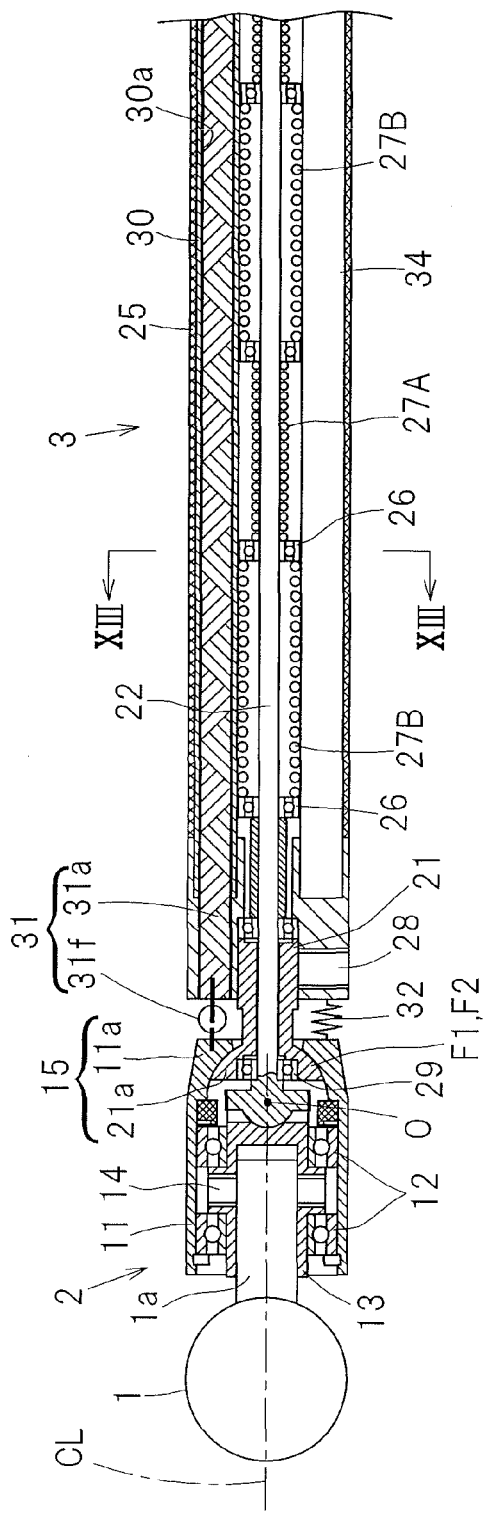
FIG. 13A is a sectional view showing the distal end member and the spindle guide member both employed in the remote controlled actuator according to a second modified form 2.
Figure 13B:
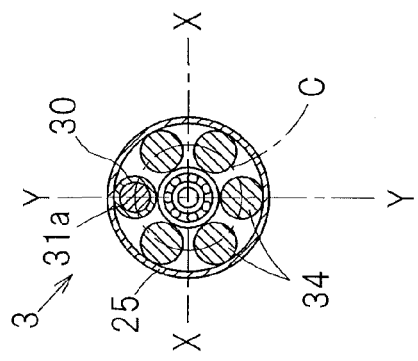
FIG. 13B is a cross sectional view taken along the line XIII-XIII in FIG. 13A.

Also, while in the fifth embodiment and the first modified form 1 the distal end member 2 has been described as altered in attitude when the attitude altering member 31 presses the housing 11, in a second modified form 2 of the fifth embodiment, as shown in FIGS. 13A and 13B, the attitude altering member 31 may be constituted solely of the attitude altering wire 31a, which has a tip end or distal end connected with the housing 11 by means of a connecting member 31f. When the attitude altering wire 31a is retracted towards a base end or proximal end side by means of the attitude altering drive source 42 (FIGS. 14A and 14B) to allow the attitude altering wire 31a to pull the housing 11 so that the distal end member 2 can be altered in attitude. In such case, the restoring elastic member 32 is to be a tension spring.

Figure 14A:
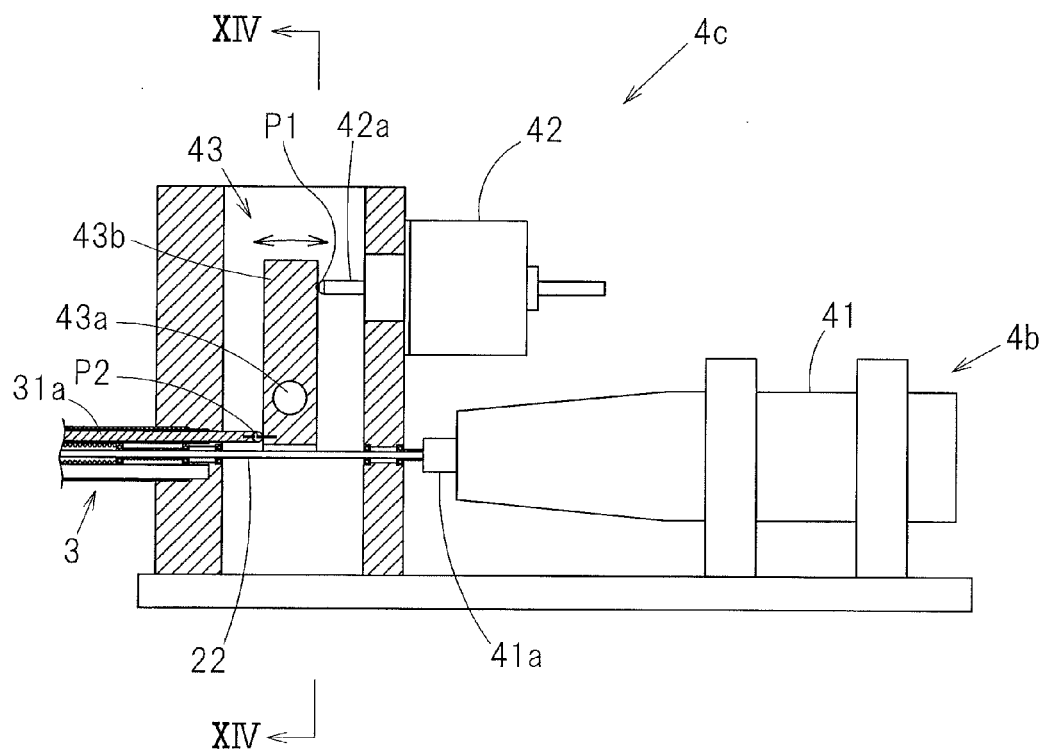
FIG. 14A is a side view showing the tool rotating drive mechanism and the attitude altering drive mechanism both employed in the remote controlled actuator according to the second modified form.
Figure 14B:
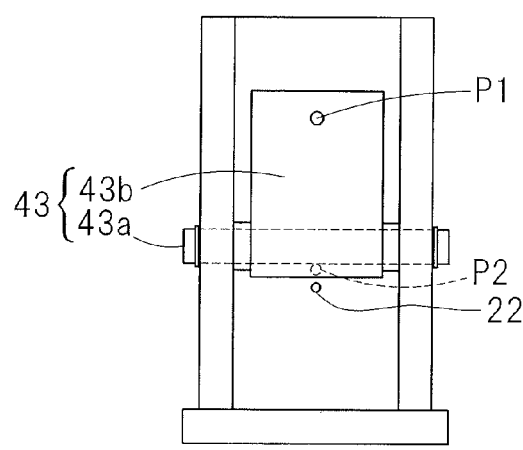
FIG. 14B is a cross sectional view taken along the line XIV-XIV in FIG. 14A.

FIGS. 14A and 14B illustrate the drive mechanism usable when the attitude altering member 31 is constructed as shown in FIGS. 13A and 13B. As is the case with the foregoing, the drive mechanism includes an attitude altering drive source 42, which is a linear actuator, an output of this attitude altering drive source 42 being transmitted to the attitude altering wire 31a through the force increasing and transmitting mechanism 43. The force increasing and transmitting mechanism 43 includes a pivot lever 43b pivotable about a support pin 43a and is so designed and so configured as to apply a force of the output rod 42a of the attitude altering drive source 42 to a working point P1 at one end of the lever 43b and as to apply a pulling force to the attitude altering wire 31a at a force point P2 located at the opposite end of the lever 43b. Since the distance from the support pin 43a to the working point P1 is longer than the distance from the support pin 43a to the force point P2, the output of the attitude altering drive source 42 is increased and then transmitted to the attitude altering wire 31a. The tool rotating drive source 41 is coupled with the base end or distal end of the rotary shaft 22 in a manner similar to that hereinbefore described.

Figure 15A:
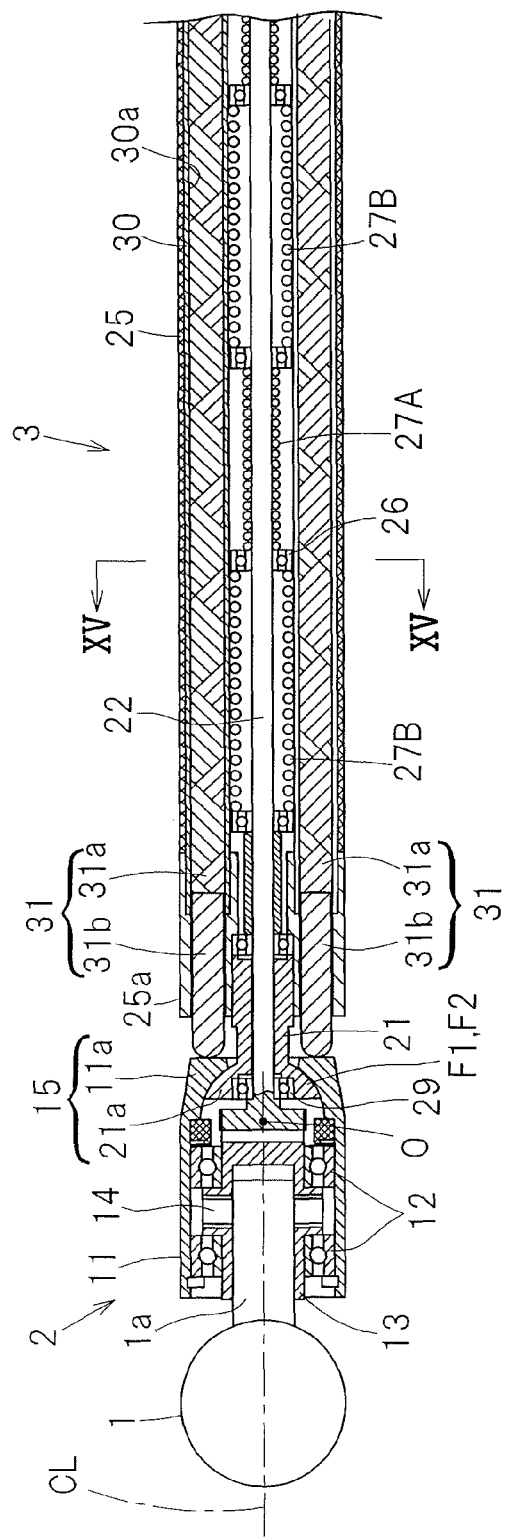
FIG. 15A is a longitudinal sectional view showing the distal end member and the spindle guide section both employed in the remote controlled actuator according to a sixth preferred embodiment of the present invention.
Figure 15B:
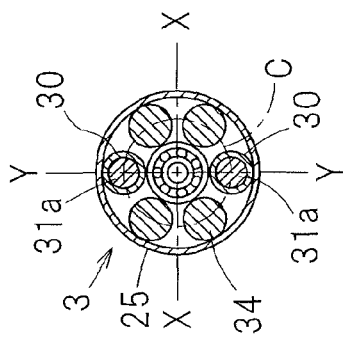
FIG. 15B is a cross sectional view taken along the line XV-XV in FIG. 15A.

FIGS. 15A and 15B illustrate a sixth preferred embodiment of the present invention. The remote controlled actuator according to this sixth embodiment makes use of two guide pipes 30 that are arranged within the outer shell pipe 25 at respective peripheral positions spaced 180° in phase from each other, and the attitude altering member 31, comprised of the attitude altering wire 31a and the pillar shaped pins 31b in a manner similar to that described hereinbefore, is reciprocally movably accommodated within each of the guide holes 30a which are inner diametric holes of the guide pipes 30. Between the two guide pipes 30, a plurality of reinforcement shafts 34 are arranged on the same pitch circle C as that of the guide pipes 30. No restoring elastic member 32 is provided. The guide surfaces F1 and F2 represent spherical surfaces each having the center of curvature lying at the point O or cylindrical surfaces each having a longitudinal axis represented by the X-axis passing through the point O.

Figure 16A:
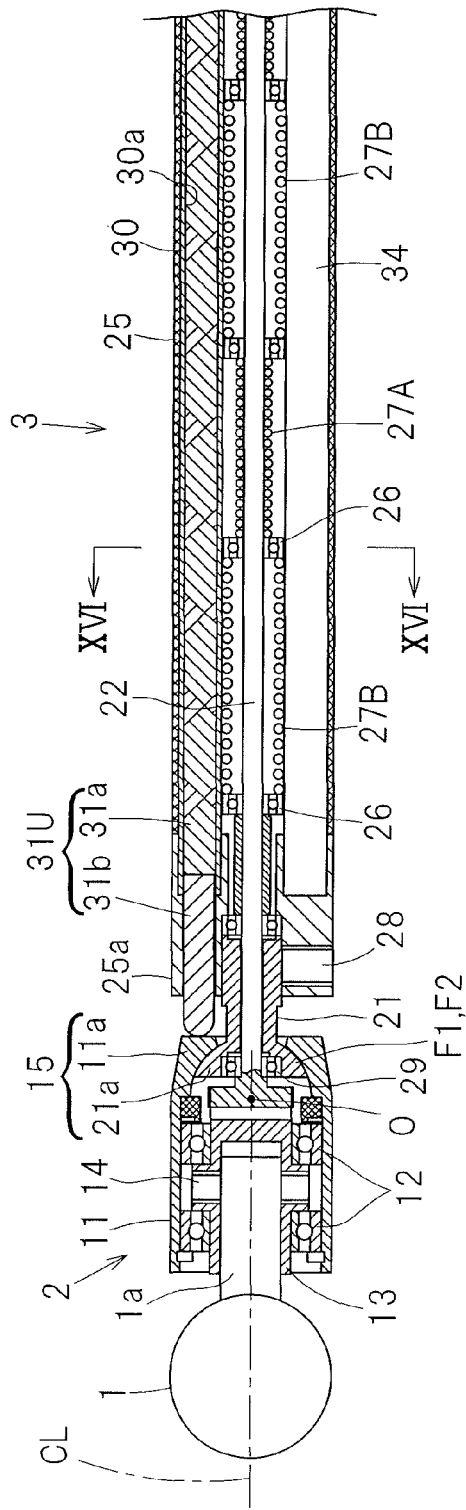
FIG. 16A is a longitudinal sectional view showing the distal end member and the spindle guide section both employed in the remote controlled actuator according to a seventh preferred embodiment of the present invention.
Figure 16B:
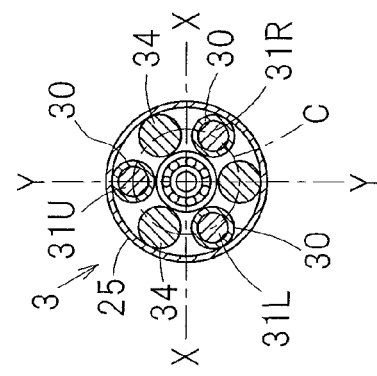
FIG. 16B is a cross sectional view taken along the line XVI-XVI in FIG. 16A.

FIGS. 16A and 16B illustrate a seventh preferred embodiment of the present invention. This seventh embodiment corresponds to the third embodiment shown in and described with reference to FIGS. 6A and 6B, but differs therefrom in that in place of the balls (the force transmitting member) 31a employed in the practice of the third embodiment, an attitude altering wire 31a is employed, but other structural features than those described above, and, also, the operation and the effects brought about thereby, are similar to those employed in and afforded by the previously described third embodiment and, therefore, the details are not reiterated for the sake of brevity.

An eighth preferred embodiment of the present invention will now be described with particular reference to FIGS. 17A to 17C to FIGS. 19A and 19B.

In the case of this eighth embodiment, as best shown in FIG. 17A, a male screw portion 36a is formed in a base end or proximal end of the attitude altering wire 31a, which portion 36a is engaged with a female screw portion 36b formed in the drive unit housing 4a. This male screw portion 36a and the female screw portion 36b altogether form a screw mechanism 36. When the base or proximal end of the attitude altering wire 31a is rotated by the drive of the attitude altering drive source 42 (FIG. 18), the attitude altering wire 31a can be selectively advanced and retracted one at a time by the action of the screw mechanism 36.

Figure 18:
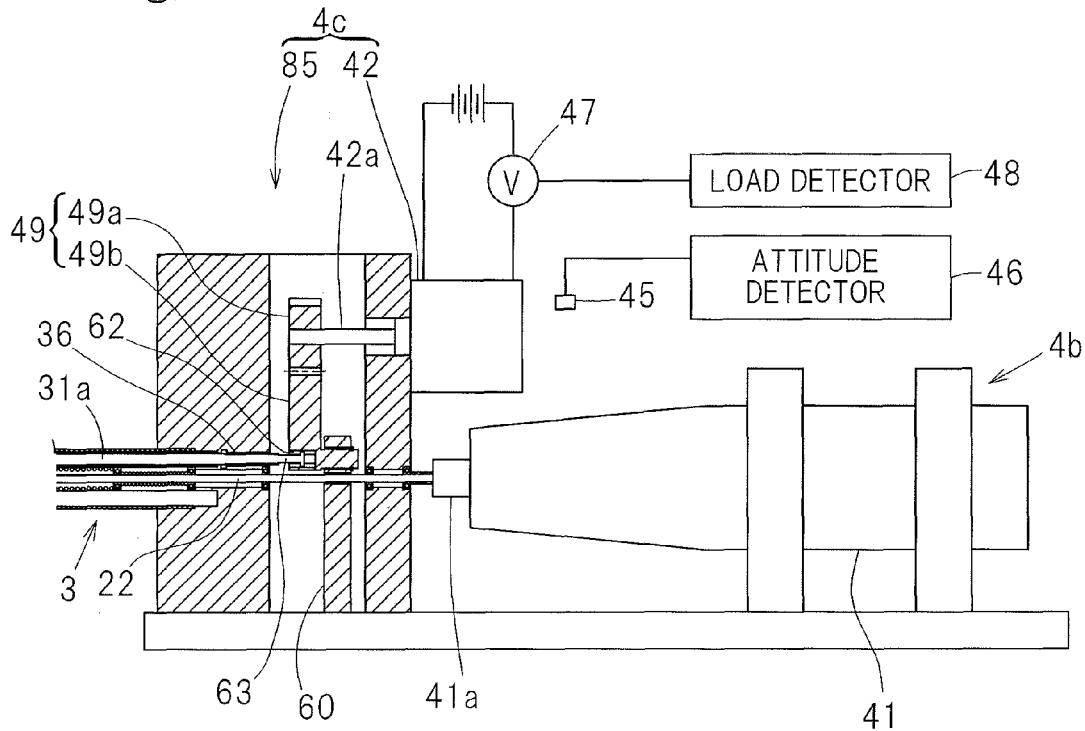
FIG. 18 is a diagram showing a side view of the drive unit, employed in the remote controlled actuator according to the eighth embodiment, together with the control system.

FIG. 18 illustrates the tool rotating drive mechanism 4b and the attitude altering drive mechanism 4c both accommodated within the drive unit housing 4a. The tool rotating drive mechanism 4b includes a tool rotating drive source 41 that is controlled by the controller 5. The tool rotating drive source 41 is employed in the form of, for example, an electric motor having an output shaft 41a connected with the base end of the rotary shaft 22. The attitude altering drive mechanism 4c includes an attitude altering drive source 42 that is controlled by the controller 5. This attitude altering drive source 42 is employed in the form of, for example, an electrically operated rotary actuator having an output shaft 42a connected with the base end of the attitude altering wire 31a through a rotation-reducing and transmitting mechanism or a reduction gear mechanism 49 so that the rotation of the output shaft 42a after having been reduced in speed can be transmitted to the base end of the attitude altering wire 31a. The attitude altering drive mechanism 4c is constituted by the attitude altering drive source 42 and a drive mechanism section 85. The drive mechanism section 85 is comprised of the screw mechanism 36 and the rotation-reducing and transmitting mechanism 49.

Figure 19B:
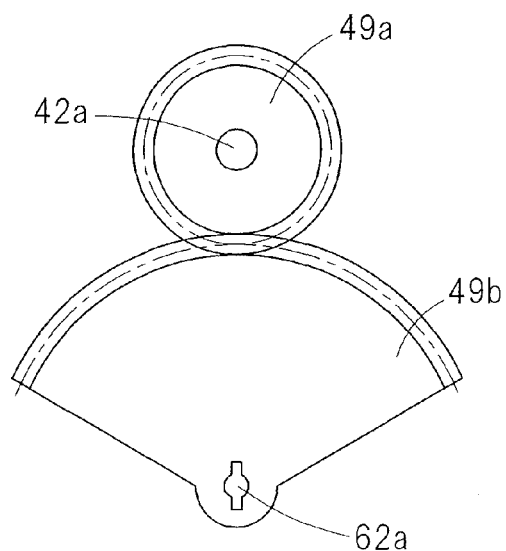
FIG. 19B is a front elevational view of the rotation-reducing and transmitting mechanism shown in FIG. 19A.
Figure 19A:
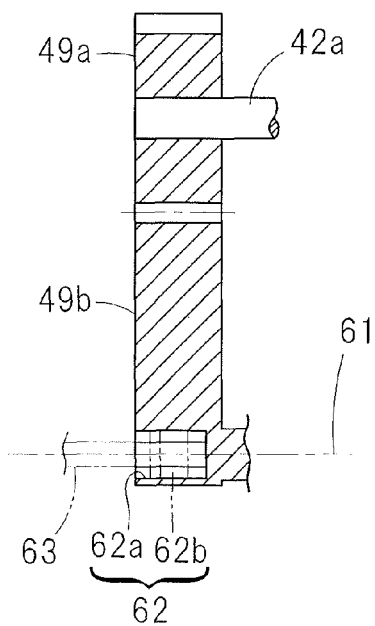
FIG. 19A is a side view showing a rotation-reducing and transmitting mechanism employed in the remote controlled actuator according to the eighth embodiment.

As shown in FIG. 18 and FIGS. 19A and 19B, the rotation-reducing and transmitting mechanism 49 includes a round spur gear 49a, mounted on the output shaft 42a of the attitude altering drive source 42, and a sector shaped spur gear 49b rotatably mounted on a support member 60, which is fixed to the drive unit housing 4a, and meshed with the round spur gear 49a and is so designed and so configured as to transmit rotation from the sector shaped spur gear 49a to a base end side extension 63 of the attitude altering wire 31a at a rotary sliding unit 62 provided on the axis 61 of rotation of the sector shaped gear 49b. The sector shaped spur gear 49b, rather than the round spur gear 49a, has a large pitch circle diameter so that the rotation of the output shaft 42a can be transmitted to the base end of the attitude altering wire 31a after having been reduced in speed. The rotary sliding unit 62 referred to above is made up of a grooved hole 62a, formed in the sector shaped spur gear 49b, and a projected axle 62b integral or rigid with the base end side extension 63, and the projected axle 62b is axially movably, but non-rotatably engaged in the grooved hole 62a. Since the use of the rotation-reducing and transmitting mechanism 49 is effective to rotate the base end of the attitude altering wire 31a at a low speed even in a compact rotary actuator of a type rotatable at a high speed, such compact rotary actuator can be employed as the attitude altering drive source 42. Also, since the rotary actuator is employed for the attitude altering drive source 42, it is sufficient to transmit the rotary output of this rotary actuator to the base end of the attitude altering wire 31a directly and, therefore, the attitude altering drive mechanism 4c can be simplified.

Since the attitude altering member 31 is passed through the guide hole 30a, the attitude altering member 31 can properly work on the distal end member 2 at all time without being displaced in a direction transverse to the longitudinal direction thereof and, therefore, the attitude alteration of the distal end member 2 can be carried out accurately. Also, since the attitude altering member 31 is made up of the attitude altering wire 31a and the pillar shaped pins 31b and is flexible in itself, the attitude alteration of the distal end member 2 can be assuredly performed even though the spindle guide section 3 has a curved portion. In addition, since the center of connection between the spindle 13 and the rotary shaft 22 lies at the same position as the center of curvature O of the guide faces F1 and F2, neither a pressing force nor a pulling force acts on the rotary shaft 22 upon alteration of the attitude of the distal end member 2 and, therefore, the distal end member 2 can be smoothly altered in attitude. The attitude altering drive source 42 is provided at a position spaced from the distal end member 2 and, therefore, the attitude alteration of the distal end member 2 can be performed by remote control.

Although when an external force acts on the tool 1 or the distal end member 2, an axially acting force acts on the attitude altering member 31 from the distal end member 2, the attitude altering member 31 does not move axially unless being rotated in a rotating direction because the attitude altering member 31 is so designed and so configured as to be selectively advanced and retracted one at a time by the screw mechanism 36. For this reason, a good stability in attitude of the distal end member 2 relative to the external force can be obtained.

In the embodiment described above, the tool rotating drive source 41 and the attitude altering drive source 42 are accommodated within the common drive unit housing 4a. Because of this, the structure of the remote controlled actuator as a whole can be simplified. It is, however, to be noted that only one of the tool rotating drive source 41 and the attitude altering drive source 42 may be provided within the drive unit housing 4a. It is also to be noted that as will be described in detail later, the tool rotating drive source and the attitude altering drive source 42 may be provided outside the drive unit housing 4a.

Figure 20:
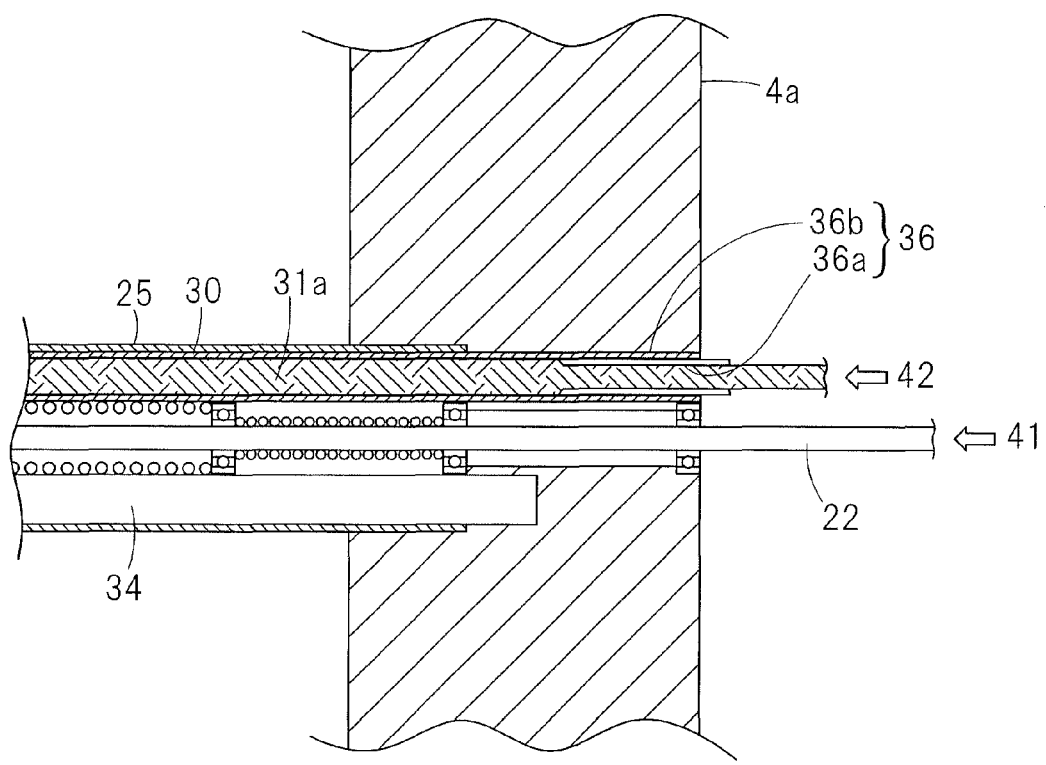
FIG. 20 is a longitudinal sectional view showing a connecting structure between the different spindle guide section and a drive unit housing.

FIG. 20 illustrates the screw mechanism of a structure different from that shown in and described with reference to FIGS. 17A to 17C. The screw mechanism 36 shown in FIG. 20 makes use of the female screw portion 36b formed in a base end inner periphery of the guide pipe 30. The make screw portion 36a is formed in the base end of the attitude altering wire 31a in a manner similar to that shown in and described with reference to FIGS. 17A to 17C. Even in this case, in a manner similar to that described previously, the attitude altering wire 31a can be selectively advanced and retracted one at a time by the action of the screw mechanism 36 when the base end of the attitude altering wire 31a is rotated by the attitude altering drive source 42 (FIG. 18).

Figure 21B:
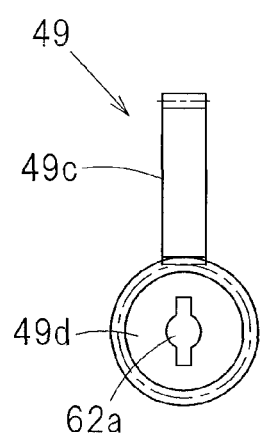
FIG. 21B is a front elevational view of the rotation-reducing and transmitting mechanism shown in FIG. 21A.
Figure 21A:
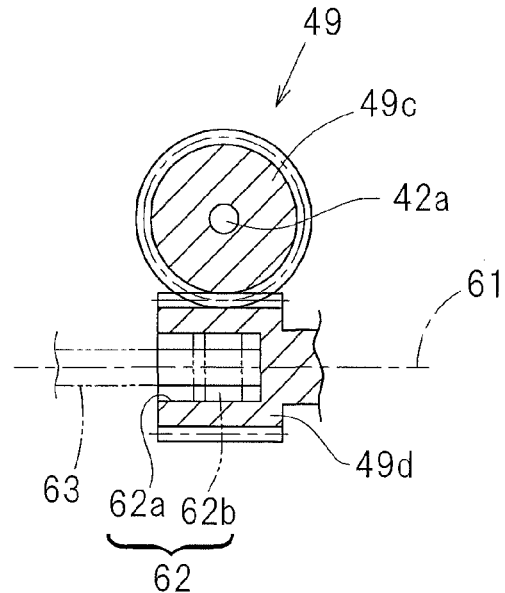
FIG. 21A is a side view showing a different rotation-reducing and transmitting mechanism.
Figure 22B:
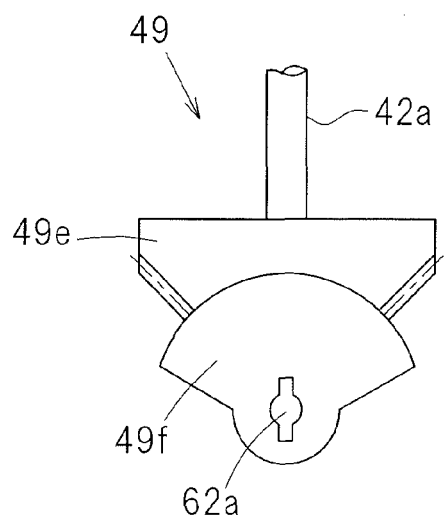
FIG. 22B is a front elevational view of the rotation-reducing and transmitting mechanism shown in FIG. 22A.
Figure 22A:
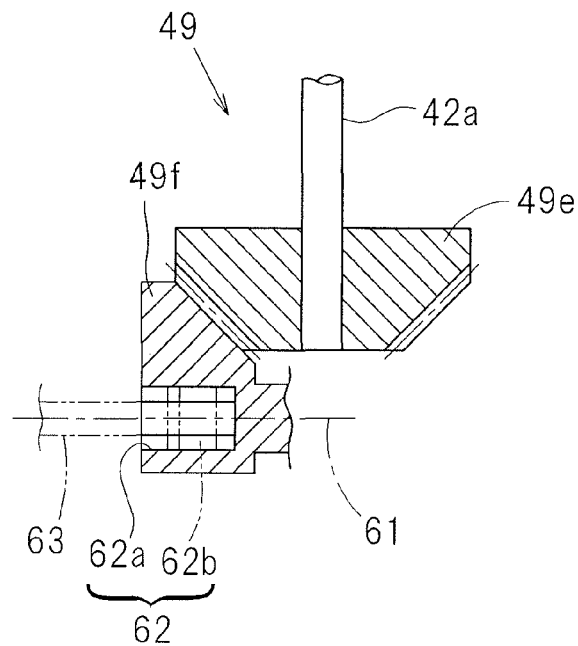
FIG. 22A is a side view showing a further different rotation-reducing and transmitting mechanism.

FIGS. 21A, 21B, 22A and 22B illustrate respective rotation-reducing and transmitting mechanisms of a structure different from that described previously. In particular, the rotation-reducing and transmitting mechanism 49 shown in FIGS. 21A and 21B is employed in the form of a worm gear mechanism including a gear 49c mounted on an output shaft 42a of the attitude altering drive source (not shown) and a worm 49d rotatably supported by a support member (not shown) and meshed with the gear 49c. On the other hand, the rotation-reducing and transmitting mechanism 49 shown in FIGS. 22A and 22B is employed in the form of a bevel gear mechanism including a first bevel gear 49e mounted on the output shaft 42a of the attitude altering drive source (not shown) and a second bevel gear 49f rotatably supported by a support member (not shown) and meshed with the first bevel gear 49e. In both cased, the rotation is transmitted from the worm 49d or the second bevel gear 49f to the base end side extension 63 of the attitude altering wire 31a with the rotary sliding unit 62 provided on the axis 61 of rotation of the worm 49d or the second bevel gear 49f.

As shown in FIGS. 23A, 23B, FIGS. 24A and 24B, the attitude altering member 31 may be constituted by a plurality of force transmitting members 31a, 31c. FIGS. 23A and 23B illustrate an example, in which the force transmitting members 31a are comprised of balls whereas FIGS. 24A and 24B illustrates an example, in which the force transmitting member 31c are comprised of pillar shaped elements such as, for example, cylinders. Those force transmitting members 31a, 31c are arranged in a row in a direction lengthwise of the guide hole 30a with no gap formed between the neighboring members. In those examples, a pillar shaped pin 31b is provided at a tip end side of the row of the force transmitting members 31a, 31c. Also, a male screw member 31e is provided on a base end side of the row of the force transmitting members 31a, 31c. The plural force transmitting members 31a, 31c, the pillar shaped pin 31b and the male screw member 31e altogether constitute the attitude altering members 31.

The male screw member 31e has a male screw portion 36a formed in an outer periphery thereof, and a female screw portion 36b formed in the drive unit housing 4a is engaged with such male screw portion 36a. When the male screw member 31e is rotated by the drive of the attitude altering drive source 42 (FIG. 18), the male screw member 31e is advanced or retracted by the action of the screw mechanism 36 and, as a result, the attitude altering member 31 in its entirety is advanced or retracted. The structure of the attitude altering mechanism 4c other than the screw mechanism 36 is the same as that shown in and described with reference to FIG. 18.

Where the attitude altering member 31 is constituted by the plural force transmitting members 31a, 31c as hereinabove described, the attitude of the distal end member 2 can be altered merely by operating the tip end (distal end) of the attitude altering member 31 towards the side in which the distal end member 2 is pressed. Accordingly, even though the attitude altering member 31 is constituted by the plural force transmitting members 31a, 31c, it is possible to assuredly bring the work on the distal end member 2. Since the force transmitting members 31a, 31c are arranged within the guide hole 30a, the distal end member 2 can be worked on properly at all time without the attitude altering member 31 displacing in a direction transverse to the longitudinal direction thereof, and the attitude alteration of the distal end member 2 can be accurately accomplished. Also, even though the individual force transmitting members 31a, 31c are rigid elements, the attitude alteration of the distal end member 2 can be assuredly accomplished even though the curved spindle guide section 3 is provided, since the attitude altering member 31 as a whole is flexible.

Although FIGS. 23A, 23B, 24A and 24B have been shown and described as illustrating the respective examples, in which the attitude altering member 31 is provided at three circumferential locations spaced 120° in phase from each other, the use of the attitude altering member 31 made up of the plural force transmitting members 31a, 31c can be made even where the attitude altering member 31 is provided at two circumferential locations spaced 180° in phase from each other and also where a combination of the attitude altering member 31, provided at one circumferential location, with the corresponding restoring elastic member 32 is made.

A ninth preferred embodiment of the present invention will now be described in detail with particular reference to FIGS. 25A to 25D and FIG. 1 and FIGS. 3A and 3B, which have been referred to in describing the first embodiment of the present invention which commonly share those figures.

As shown in FIGS. 25A to 25D, in the practice of the ninth embodiment of the present invention, an attitude altering wire is used for the attitude altering member 31. A rotation preventing mechanism 37 is constituted by a radially extending groove portion 11b, formed in a base end (distal end) surface of the housing 11, and the attitude altering member 31 having its tip end held in contact with the bottom of the groove portion 11b. When the tip end (distal end) portion of the attitude altering member 31 inserted into the groove portion 11b is held in abutment with a side face of the groove portion 11b, the distal end member 2 can be prevented from being rotated about a center line CL of the distal end member 2 relative to the spindle guide section 3. Other structural features and functions than those described above are similar to those described in connection with the first embodiment and, therefore, the details thereof are not reiterated for the sake of brevity.

Since as hereinabove described, the ninth embodiment of the present invention makes use of the rotation preventing mechanism 37 for preventing the distal end member 2 from rotating about the center line CL of the distal end member 2 relative to the spindle guide section 3, even when the distal end member 2 then holding the tool 1 becomes uncontrollable as a result of any trouble occurring in the attitude altering drive mechanism 4c for controlling the selective advance and retraction of the attitude altering member 31 and/or the control device therefor, it is possible to avoid the possibility that the site to be processed may be impaired as a result of rotation of the distal end member 2 about the center line CL or the distal end member 2 itself is broken.

Figure 26A:
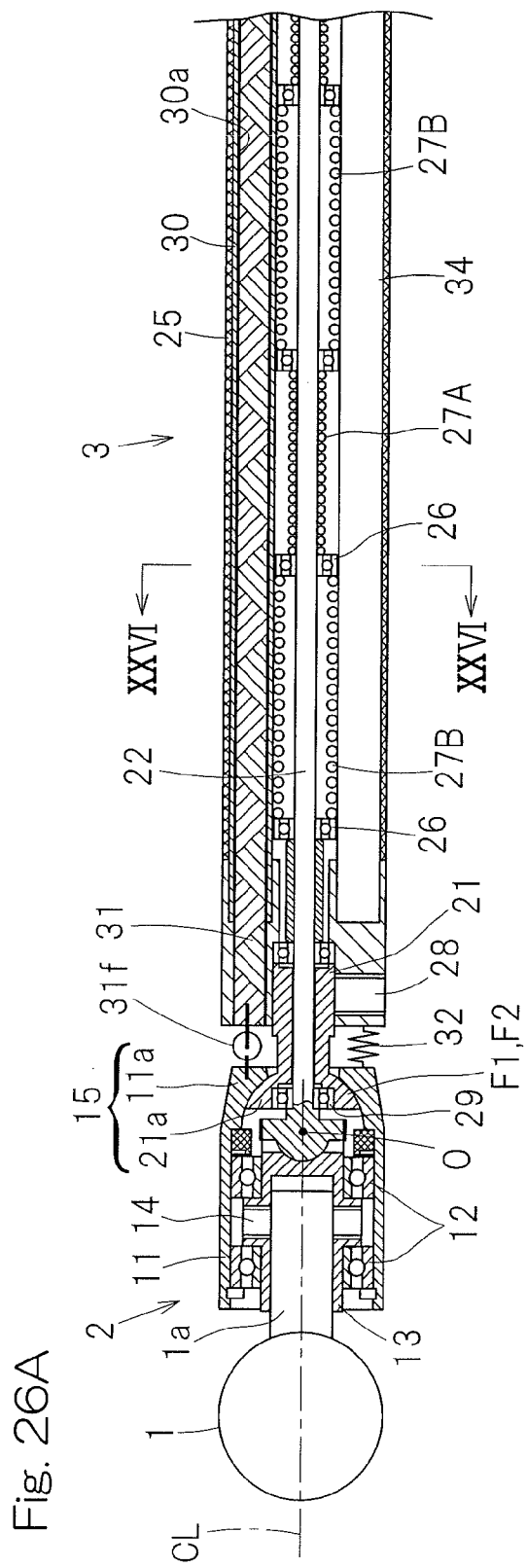
FIG. 26A is a longitudinal sectional view showing the distal end member and the spindle guide section both employed in the remote controlled actuator according to a tenth preferred embodiment of the present invention.
Figure 26C:
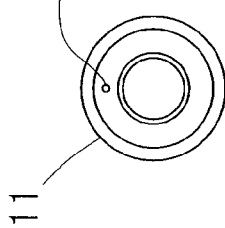
FIG. 26C is a view showing the housing for the distal end member as viewed from the proximal end.
Figure 26B:
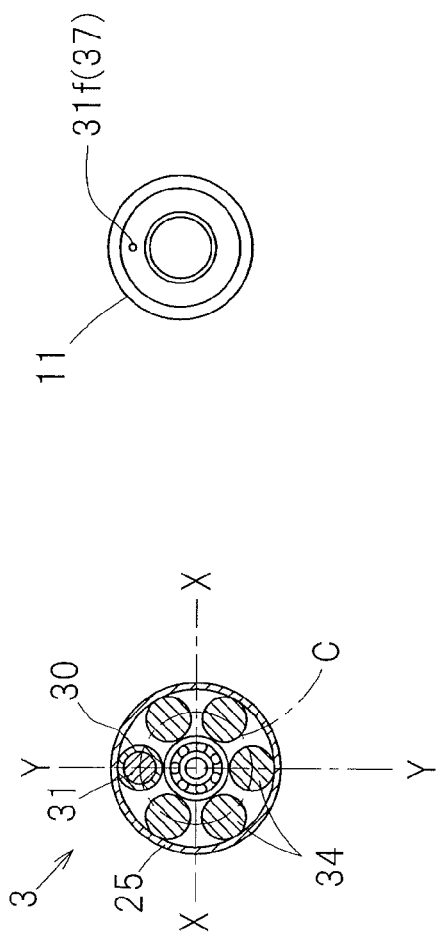
FIG. 26B is a cross sectional view taken along the line XXVI-XXVI in FIG. 26A.

Although in the above described embodiment the attitude alteration of the distal end member 2 is accomplished when the attitude altering member 31 presses the housing 11, arrangement such as in a tenth preferred embodiment of the present invention, shown in FIGS. 26A to 26C, that the tip end of the attitude altering member 31 in the form of a wire and the housing 11 are connected with each other by means of a connecting member 31f so that when the attitude altering member 31 is retracted towards the base end side by the attitude altering drive source (not shown), the attitude altering member 31 can pull the housing 11 to allow the distal end member 2 to be altered in attitude. The restoring elastic member 32 is employed in the form of a tension spring. In such case, the connecting member 31f forms the rotation preventing mechanism 37 for preventing the distal end member 2 from rotating about the center line CL relative to the spindle guide section 3.

Figure 27A:
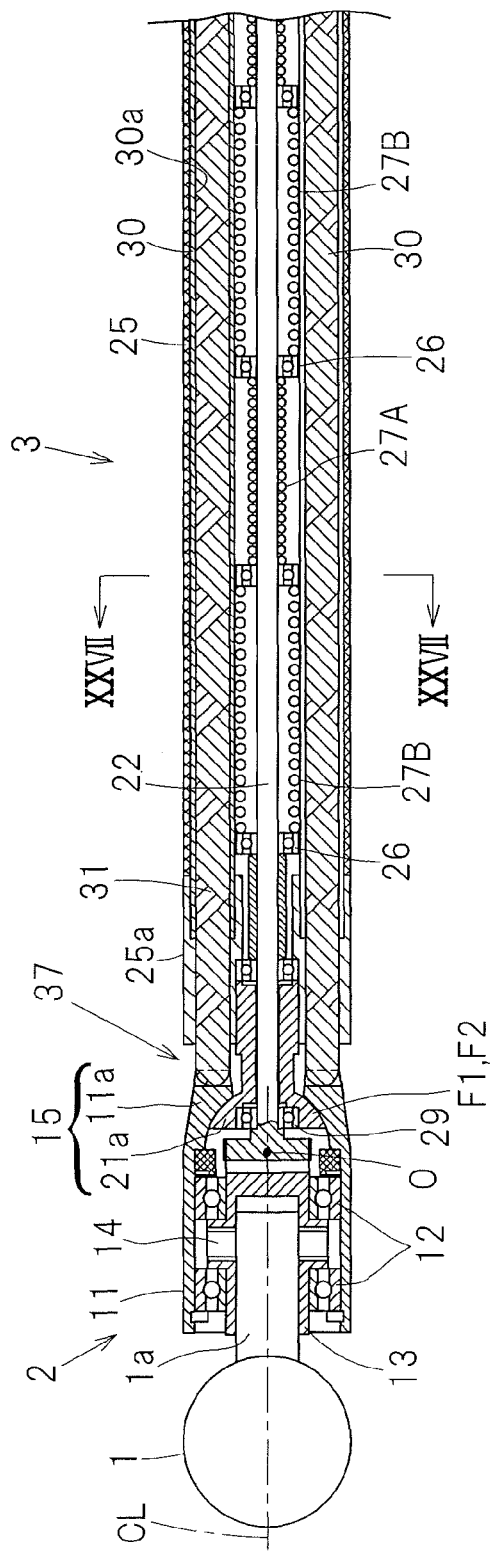
FIG. 27A is a longitudinal sectional view showing the distal end member and the spindle guide section both employed in the remote controlled actuator according to an eleventh preferred embodiment of the present invention.
Figure 27C:
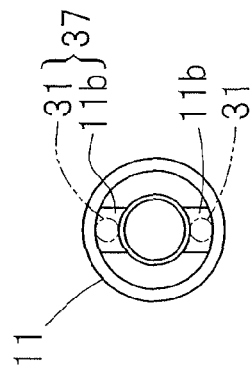
FIG. 27C is a view showing the housing for the distal end member as viewed from the proximal end.
Figure 27B:
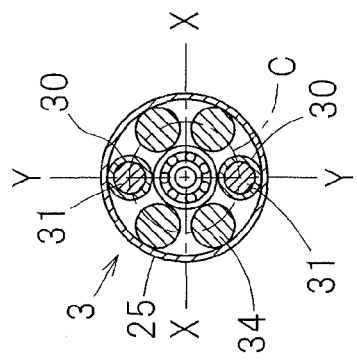
FIG. 27B is a cross sectional view taken along the line XXVII-XXVII in FIG. 27A.

FIGS. 27A to 27C illustrate an eleventh preferred embodiment of the present invention. This eleventh embodiment corresponds to the second embodiment shown in and described with particular reference to FIGS. 5A and 5B and, in place of the attitude altering member 31 employed in the second embodiment, an attitude altering member comprised of a wire is employed, in which a spherical tip end of each attitude altering member 31 is held in contact with the bottom face of a radial groove portion 11b, formed in the base end face of the housing 11. Those groove portions 11b and the attitude altering members 31 altogether form the rotation preventing mechanism 37 for enabling rotation of the distal end member 2 about the center line CL of the distal end member 2 relative to the spindle guide section 3.

Figure 28A:
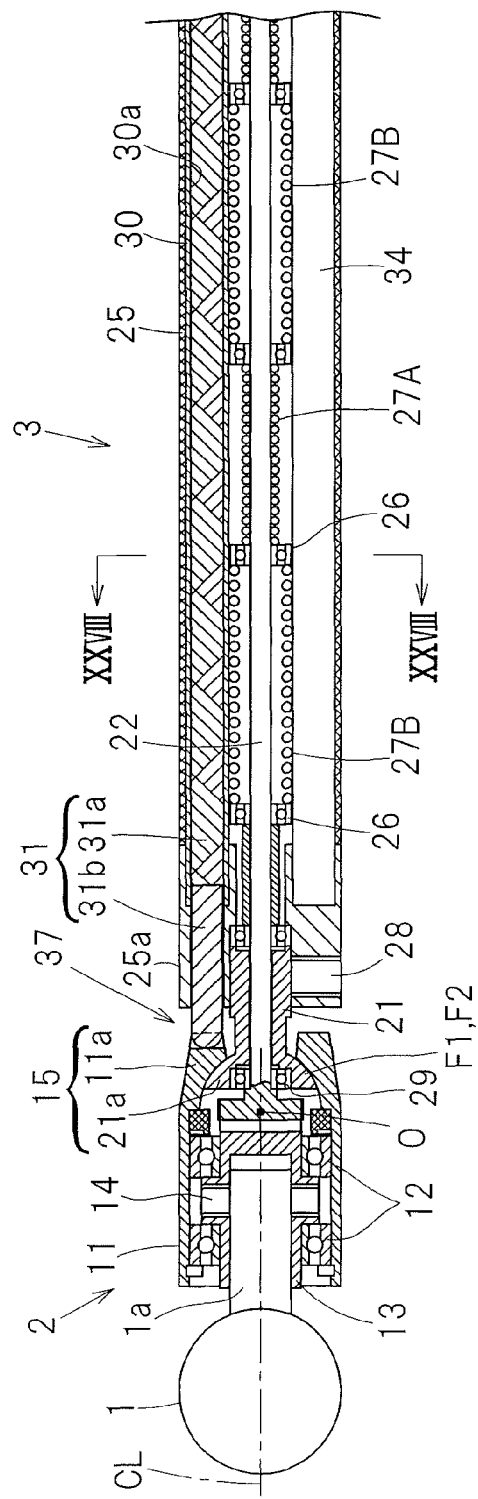
FIG. 28A is a longitudinal sectional view showing the distal end member and the spindle guide section both employed in the remote controlled actuator according to a twelfth preferred embodiment of the present invention.
Figure 28C:
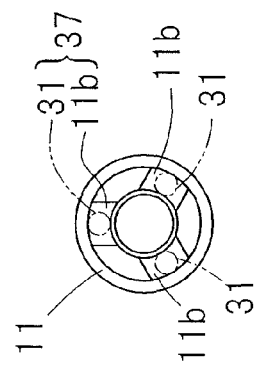
FIG. 28C is a view showing the housing for the distal end member as viewed from the proximal end.
Figure 28B:
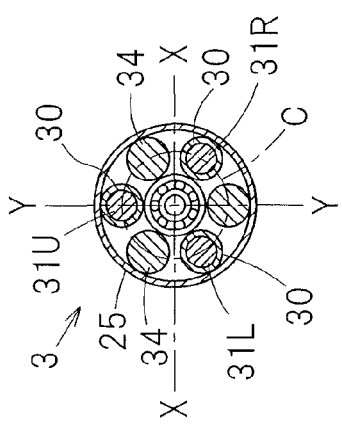
FIG. 28B is a cross sectional view taken along the line XXVIII-XXVIII in FIG. 28A.

A twelfth preferred embodiment of the present invention is shown in FIGS. 28A to 28C. This twelfth embodiment corresponds to the third embodiment shown in and described with particular reference to FIGS. 6A and 6B and, in place of the attitude altering member 31 employed in the third embodiment, the use is made of an attitude altering member comprised of a wire 31a and a pillar shaped pin 31b provided on the tip end (distal end) side of the wire 31a. The groove 11b in the housing 11 and the pillar shaped pin 31b altogether form the rotation preventing mechanism 37 for enabling rotation of the distal end member 2 about the center line CL of the distal end member 2 relative to the spindle guide section 3.

As is the case with a thirteenth preferred embodiment of the present invention shown in FIGS. 29A to 29C and a fourteenth preferred embodiment of the present invention shown in FIGS. 30A to 30C each having the groove 11b, the attitude altering member 31 may be constituted by a plurality of force transmitting members arranged in a row in a direction lengthwise of the guide hole 30a with no gap formed between the neighboring force transmitting members 31. The thirteenth embodiment shown in FIGS. 29A to 29C corresponds to the third embodiment shown in and described with particular reference to FIGS. 6A and 6B and the plural force transmitting members are employed in the form of balls 31a and a pillar shaped pin 31b is provided on the tip end side of the row of the balls 31a. The fourteenth embodiment shown in FIGS. 30A to 30C corresponds to the fourth embodiment shown in and described with particular reference to FIGS. 7A and 7B and the plural force transmitting members are employed in the form of pillar shaped elements 31c such as, for example, cylinders and a pillar shaped pin 31b is provided on the tip end side of the row of the pillar shaped elements 31c. The pillar shaped pin 31b is similar to that described previously. The groove portion 11b of the housing 11 and the pillar shaped pin 31b altogether constitute the rotation preventing mechanism 37 for enabling rotation of the distal end member 2 about the center line CL of the distal end member 2 relative to the spindle guide section 3.

As hereinabove described, where the attitude altering member 31 is constituted by the plural force transmitting members 31a, 31c, the attitude of the distal end member 2 can be altered by operating the tip end (distal end) of the attitude altering member 31 towards the side in which the distal end member 2 is pressed. Even though the attitude altering member 31 is constituted by the plural force transmitting members 31a, 31c, it is possible to assuredly bring the work on the distal end member 2. Since the force transmitting members 31a, 31c are arranged within the guide hole 30a, the distal end member 2 can be worked on properly at all time without the attitude altering member 31 displacing in a direction transverse to the longitudinal direction thereof, and the attitude alteration of the distal end member 2 can be accurately accomplished. Also, even though the individual force transmitting members 31a, 31c are rigid elements, the attitude alteration of the distal end member 2 can be assuredly accomplished even though the curved spindle guide section 3 is provided, since the attitude altering member 31 as a whole is flexible.

Although FIGS. 29A to 29C and FIGS. 30A to 30C have been shown and described as illustrating the respective examples, in which the attitude altering member 31 is provided at three circumferential locations spaced 120° in phase from each other, the use of the attitude altering member 31 made up of the plural force transmitting members 31a, 31c can be made even where the attitude altering member 31 is provided at two circumferential locations spaced 180° in phase from each other and also where a combination of the attitude altering member 31, provided at one circumferential location, with the corresponding restoring elastic member 32 is made.

Figure 31:
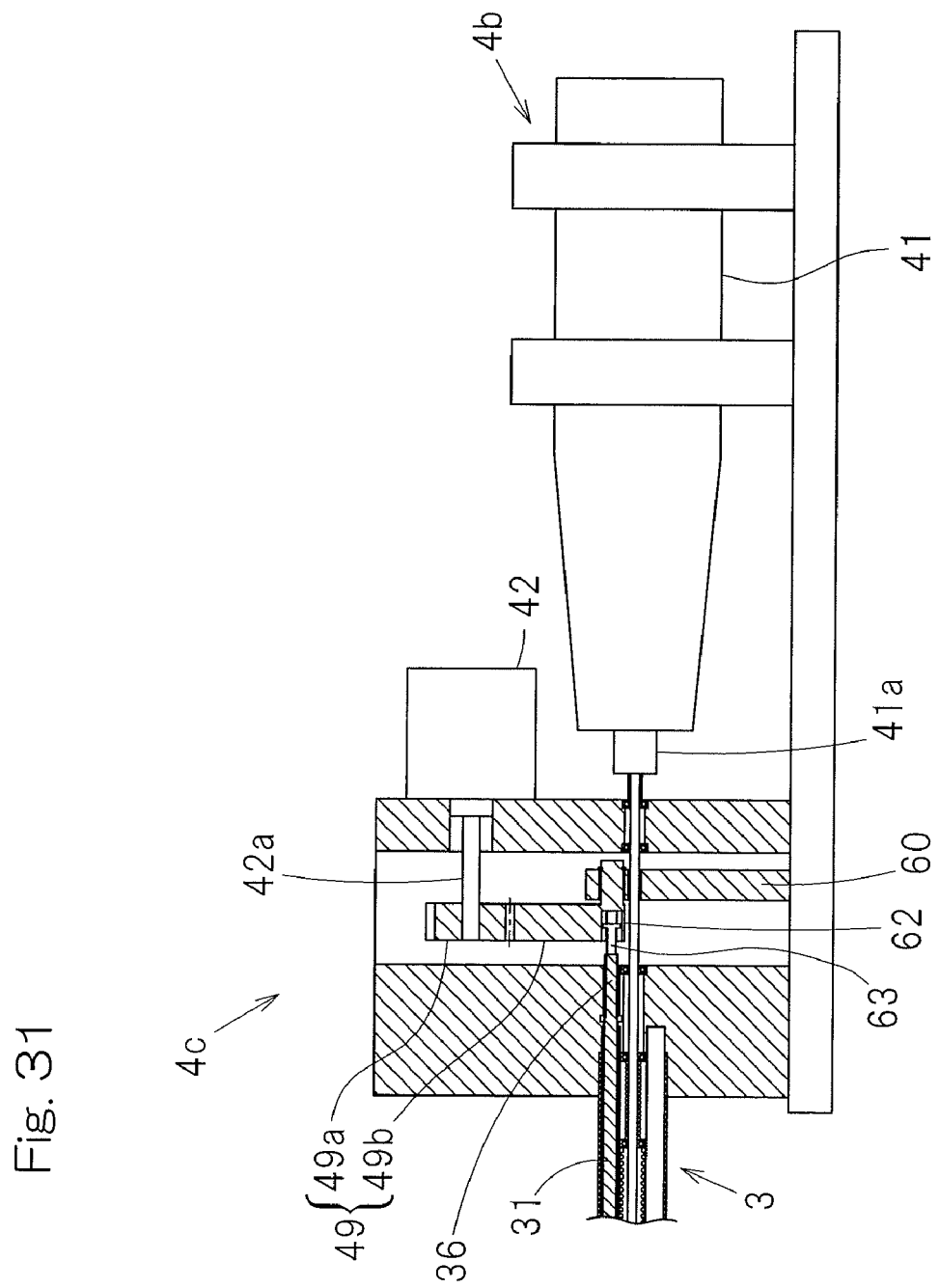
FIG. 31 is a partially cutout side view showing the tool rotating drive mechanism and the attitude altering drive mechanism both employed in the remote controlled actuator of the type employing a different structure of the attitude altering drive mechanism.

FIG. 31 illustrates, in partially cutout sectional representation, the tool rotating drive mechanism and the attitude altering drive mechanism, both employed in the embodiment of the present invention employing a different structure of the attitude altering drive mechanism 4c. In this embodiment, the male screw portion 36a is formed in the base end of the attitude altering member 31 comprised of a wire and is threadingly engaged with the female screw portion formed in the drive unit housing 4a. The male screw portion 36a and the female screw portion 36b altogether constitute the screw mechanism 36. The attitude altering member 31 is selectively advanced and retracted one at a time by the action of the screw mechanism 36 when the base end of the attitude altering member 31 is rotated by the drive of the attitude altering drive source 42.

The attitude altering drive mechanism 4c is similar in structure to that described hereinbefore and, therefore, the details thereof are not reiterated. The tool rotating drive mechanism 4b as well is of a structure similar to that described hereinbefore.

FIGS. 32A to 32D illustrate a fifteenth preferred embodiment of the present invention.

In the case of this fifteenth embodiment, the guide pipe 30 is fixed to the outer shell pipe 25 by means of a pipe fixing segment 70. This pipe fixing segment 70 is of a structure, in which while the outer shell pipe 25 has its peripheral wall formed with at least one opening 71 extending completely across the thickness of such peripheral wall, a portion of a circumferential area of such opening 71 in the outer shell pipe 25 and the guide pipe 30 are fixedly connected with each other by means of soldering or welding at locations 72.

According to the fifteenth embodiment, because the outer shell pipe 25 and the guide pipe 30 are fixedly connected together by means of the pipe fixing segment 70, the spindle guide section 3 comes to have an increased section modulus, accompanied by an increase of the rigidity. For this reason, even when a force acts on the distal end member 2, the spindle guide section 3 will become hard to bend or flex and the positioning accuracy of the distal end member relative to the drive unit housing 4a can be increased. Since the pipe fixing segment 70 is formed by forming the opening 71 in the peripheral wall of the outer shell pipe 25 so as to extend completely across the thickness of the peripheral wall and then soldering or welding the circumferential area of the opening 71 with the guide pipe 30 at the locations 72, the outer shell pipe 25 and the guide pipe 30 can be relatively easily and firmly connected with each other.

The pipe fixing segment 70, through which the outer shell pipe 25 and the guide pipe 30 are fixedly connected together, may be formed by providing no opening 71, which is defined in the peripheral wall of the outer shell pipe 25 so as to extend completely across the thickness of such peripheral wall (FIGS. 32A to 32D), as in a sixteenth preferred embodiment of the present invention shown in FIGS. 33A to 33D. In this embodiment, the outer shell pipe 25 and the guide pipe 30 are fixedly connected together by means of a laser welding at the locations 73 from an outer diametric surface side of the outer shell pipe 25. Even in this case, the outer shell pipe 25 and the guide pipe 30 can be relatively easily and firmly connected with each other. Also, since there is no need to form the opening in the outer shell pipe 25, not only can the rigidity of the spindle guide section 3 be further increased to an extent higher than that afforded by the previously described embodiment, but the assemblability can also be increased.

Figure 34B:
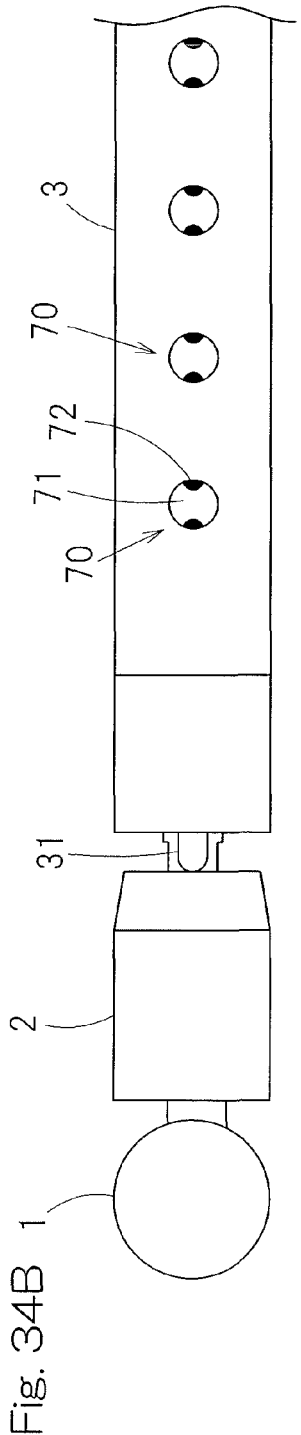
FIG. 34B is a top plan view of the distal end member and the spindle guide section shown in FIG. 34A.
Figure 34A:
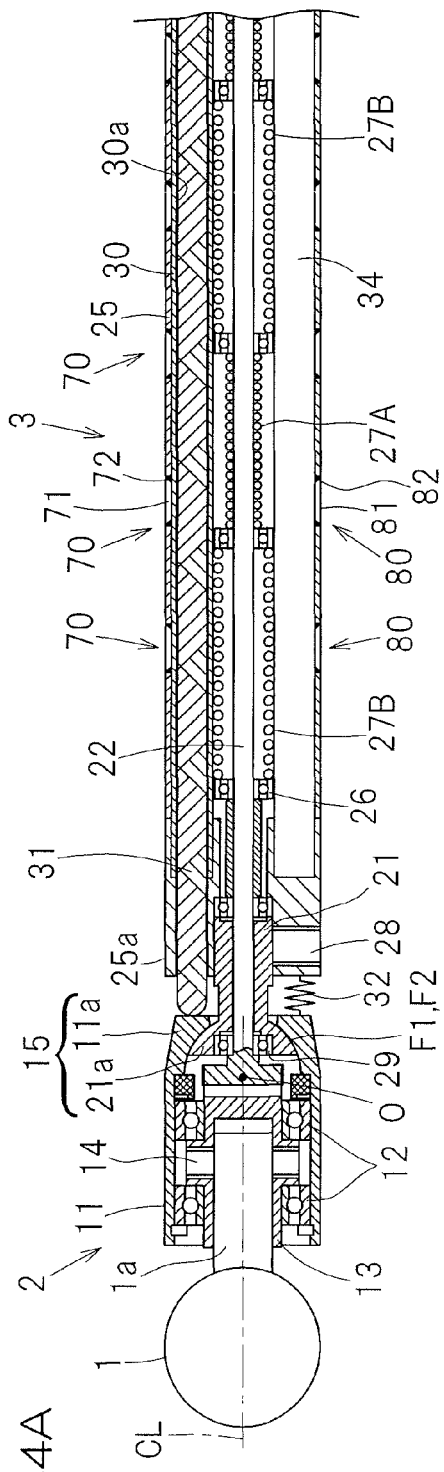
FIG. 34A is a longitudinal sectional view showing the distal end member and the spindle guide section both employed in the remote controlled actuator according to a seventeenth preferred embodiment of the present invention.
Figure 34C:
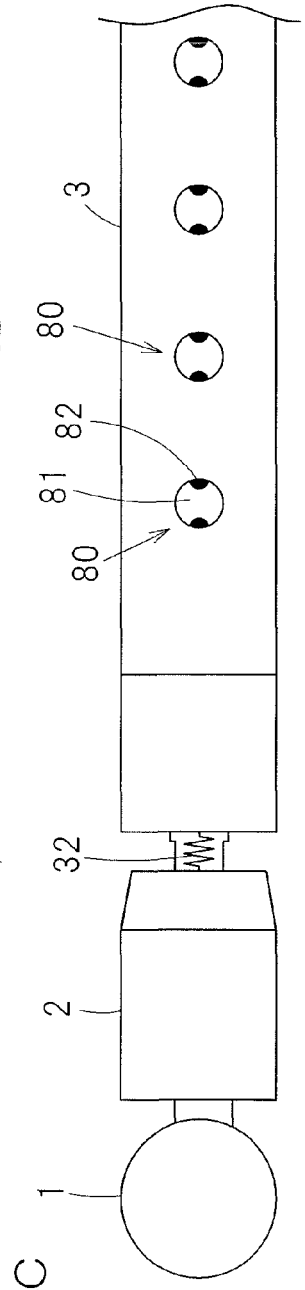
FIG. 34C is a bottom plan view of the distal end member and the spindle guide section shown in FIG. 34A.
Figures 35A, 35B, 35C:
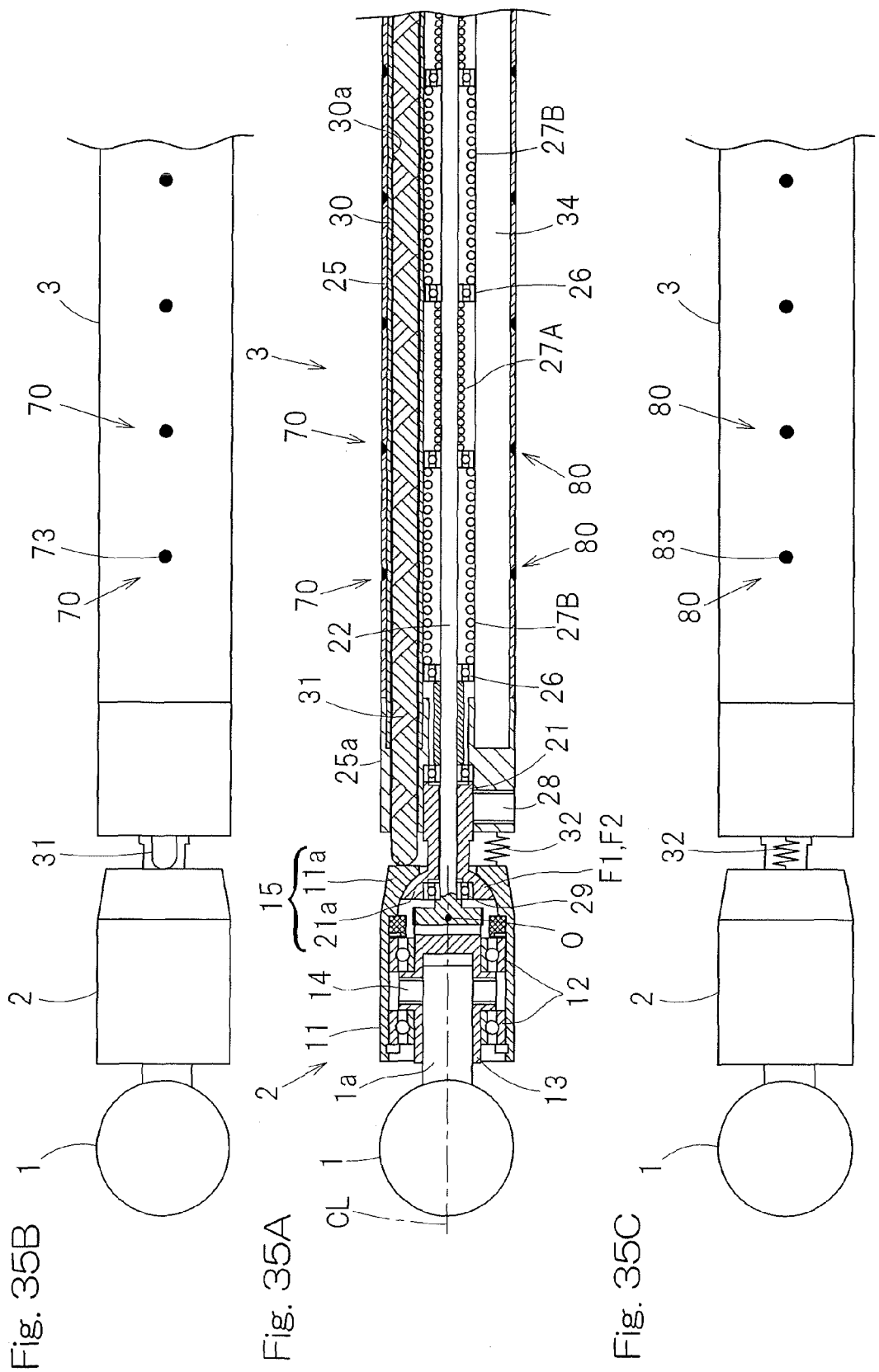
FIG. 35A is a longitudinal sectional view showing the distal end member and the spindle guide section both employed in the remote controlled actuator according to an eighteenth preferred embodiment of the present invention.
FIG. 35B is a top plan view of the distal end member and the spindle guide section shown in FIG. 35A.
FIG. 35C is a bottom plan view of the distal end member and the spindle guide section shown in FIG. 35A.

Also, as is the case with seventeenth and eighteenth preferred embodiments of the present invention shown in FIGS. 34A to 34C and FIGS. 35A to 35C, respectively, the outer shell pipe 25 and each of the reinforcement shafts 34 may be fixed together by means of a shaft fixing segment 80. Specifically, the shaft fixing segment 80 shown in FIGS. 34A to 34C is formed by forming an opening 81 in a peripheral wall of the outer shell pipe 25 extending completely across the thickness of such peripheral wall and soldering or welding a portion of a circumferential area of the opening 81 in the outer shell pipe 25 with the reinforcement shaft 34 at locations 82. On the other hand, the shaft fixing segment 80 shown in FIGS. 35A to 35C is formed by fixedly connecting the outer shell pipe 25 and the reinforcement shaft 34 together by means of a laser welding at the locations 83 from an outer diametric surface side of the outer shell pipe 25 without the opening 81 formed in the outer shell pipe 25.

As hereinabove described, if the guide pipe 30 and each of the reinforcement shafts 34 are fixedly connected with the outer shell pipe 25, the spindle guide section 3 can have a further increased section modulus, accompanied by an increase of the rigidity. For this reason, even when a force acts on the distal end member 2, the spindle guide section 3 will become hard to bend or flex and the positioning accuracy of the distal end member 2 relative to the drive unit housing 4a can be increased. Also, since the bearings 26 can be stably supported by the guide pipe 30 and each of the reinforcement shafts 34, vibration which would occur in the rotary shaft 22 can be reduced. Although in FIGS. 34A to 34C and FIGS. 35A and 35C, the pipe fixing segment 70 and the shaft fixing segment 80 are rendered to occupy the same axial position, the respective axial positions of the both may be displaced.

Figure 36A:
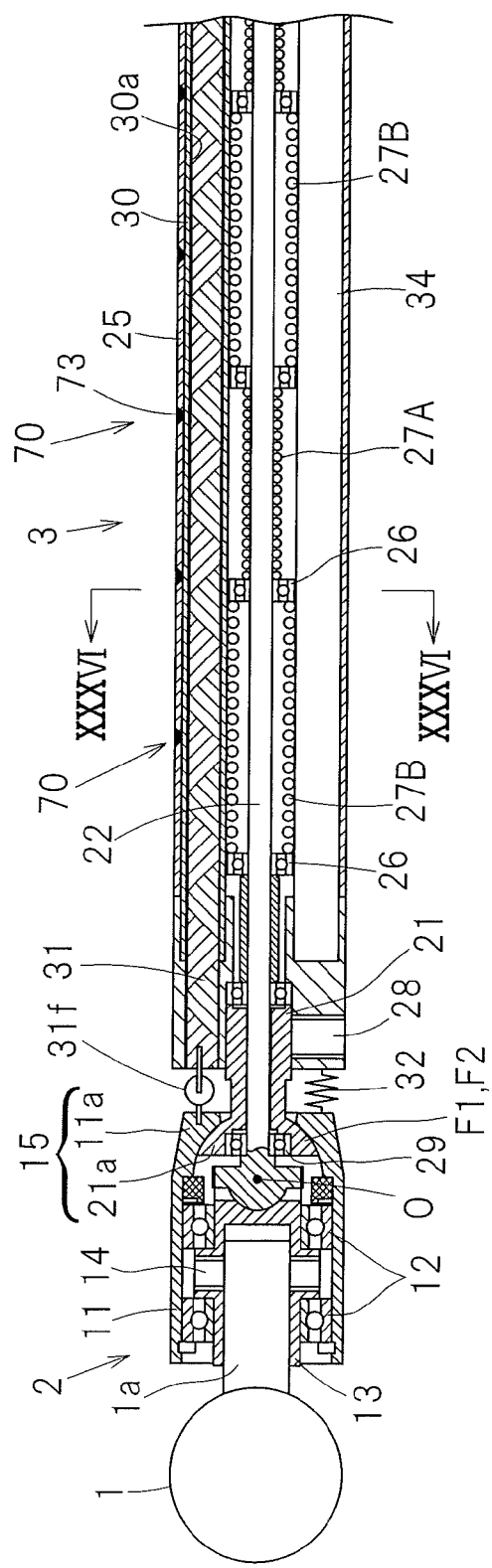
FIG. 36A is a longitudinal sectional view showing the distal end member and the spindle guide section both employed in the remote controlled actuator according to a nineteenth preferred embodiment of the present invention.
Figure 36B:
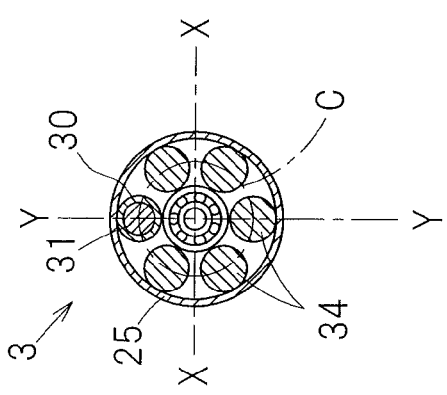
FIG. 36B is a cross sectional view taken along the line XXXVI-XXXVI in FIG. 36A.

While in any one of the foregoing embodiments of the present invention, the attitude alteration of the distal end member 2 has been shown and described as accomplished by causing the attitude altering member 31 to press the housing 11, arrangement such as in the case of a nineteenth preferred embodiment of the present invention shown in FIGS. 36A to 36B may be made that the tip end of the attitude altering member 31, comprised of a wire, and the housing 11 are connected with each other by means of a connecting member 31f so that when the attitude altering member 31 is retracted towards the base end side by means of the attitude altering drive source (not shown), the attitude altering member 31 can pull the housing 11 to alter the attitude of the distal end member 2. In such case, the restoring elastic member 32 is to be employed in the form of a tension spring. In this illustrated example, by the pipe fixing segment 70, the outer shell pipe 25 and the guide pipe 30 are connected with each other through the pipe fixing segment 70 by means of the laser welding at the locations 73.

FIGS. 37A and 37B illustrate a twentieth preferred embodiment of the present invention. This twenty first embodiment corresponds to the sixth embodiment shown in and described with particular reference to FIGS. 15A and 15B and each of the attitude altering members 31 is made up of a wire 31a and a pillar shaped pin 31b provided on the tip end side of the wire 31a. The pillar shaped pin 31b has a tip end representing a spherical shape and the spherical tip end is held in contact with the base end surface of the housing 11. In this embodiment, the outer shell pipe 25 and each of the guide pipes 30 are fixedly connected with each other through the pipe fixing segment 70 by means of a laser welding at the locations 73. The operation of this embodiment is similar to that of the previously described sixth embodiment and, therefore, the details thereof are not reiterated.

Figure 38A:
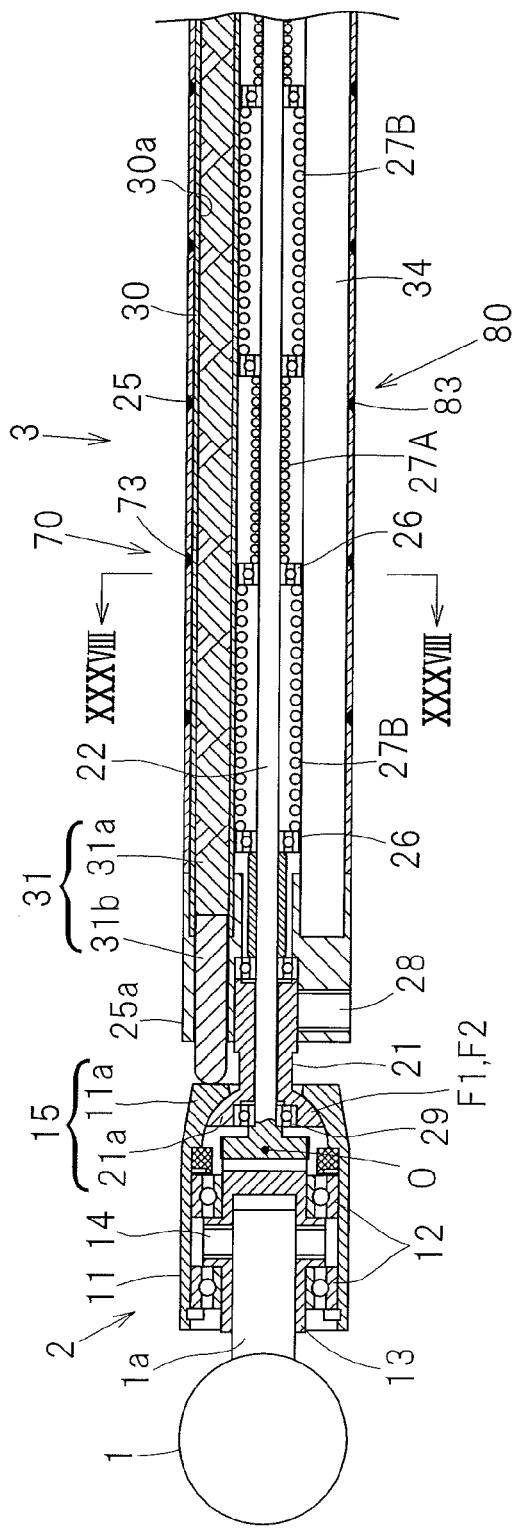
FIG. 38A is a longitudinal sectional view showing the distal end member and the spindle guide section both employed in the remote controlled actuator according to a twenty first preferred embodiment of the present invention.
Figure 38B:
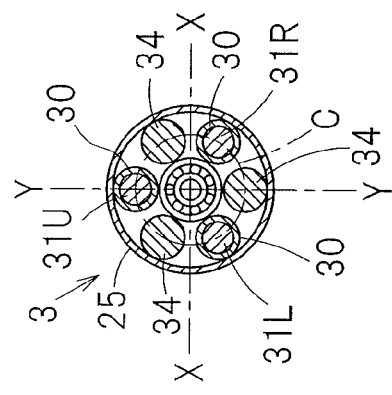
FIG. 38B is a cross sectional view taken along the line XXXVIII-XXXVIII in FIG. 38A.

FIGS. 38A and 38B illustrates a twenty first preferred embodiment of the present invention. This twenty second embodiment corresponds to the seventh embodiment shown in and described with particular reference to FIGS. 16A and 16B and not only are the outer shell pipe 25 and each of the guide pipes 30 be fixedly connected with each other through the pipe fixing segment 70 by means of the laser welding at the locations 73, but the outer shell pipe 25 and each of the reinforcement shafts 34 are also fixedly connected with each other through a shaft fixing segment 80 by means of the laser welding at the locations 83. The operation of this embodiment is similar to that of the previously described seventh embodiment and, therefore, the details thereof are not reiterated.

As is the case with twenty second and twenty third preferred embodiments of the present invention shown in FIGS. 39A and 39B and FIGS. 40A and 40B, respectively, the attitude altering member 31 may be comprised of a plurality of force transmitting members arranged in a row in a direction lengthwise of the guide hole 30a with no gap formed between the neighboring force transmitting members. Specifically, in the twenty second embodiment shown in FIGS. 39A and 39B, the plural force transmitting members are employed in the form of balls 31a and a pillar shaped pin 31b is provided on the tip end side of the row of the balls 31a. On the other hand, in the twenty third embodiment shown in FIGS. 40A and 40B, the plural force transmitting members are employed in the form of pillar shaped elements 31e such as, for example, cylinders and a pillar shaped pin 31b is provided on the tip end side of the row of the pillar shaped elements 31c. The pillar shaped pin 31b is similar to that previously described and has its tip end representing a spherical shape and is held in contact with the base end surface of the housing 11. In any of those illustrated examples, the outer shell pipe 25 and each of the guide pipes 30 are fixedly connected with each other through the pipe fixing segment 70 by means of the laser welding at the locations 73 and, also, the outer shell pipe 25 and each of the reinforcement shafts 34 are fixedly connected with each other through the shaft fixing segment 80 by means of the laser welding at the locations 83.

FIGS. 41 to 44 illustrate a twenty fourth preferred embodiment of the present invention, in which the tool rotating drive mechanism and the attitude altering drive mechanism, both having a structure different from that described hereinbefore, are employed. Whereas in the previous embodiment the tool rotating drive source 41 of the tool rotating drive mechanism 4b and the attitude altering drive source 42 of the attitude altering drive mechanism 4c have been shown and described as provided within the drive unit housing 4a, the twenty fourth embodiment shown in FIGS. 41 to 44 makes use of a drive source housing 100, different from the drive unit housing 4a, for accommodating the tool rotating drive source 41 and the attitude altering drive source 42 therein.

Figure 42:
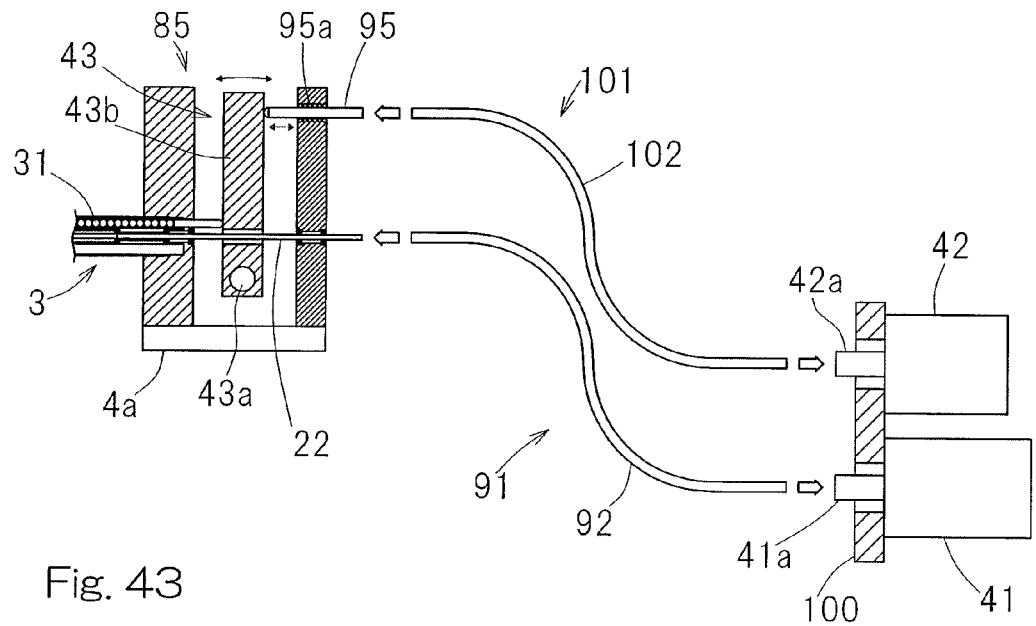
FIG. 42 is a diagram showing a structure of the tool rotating drive mechanism and the attitude altering drive mechanism employed in the remote controlled actuator shown in FIG. 41.
Figure 43:
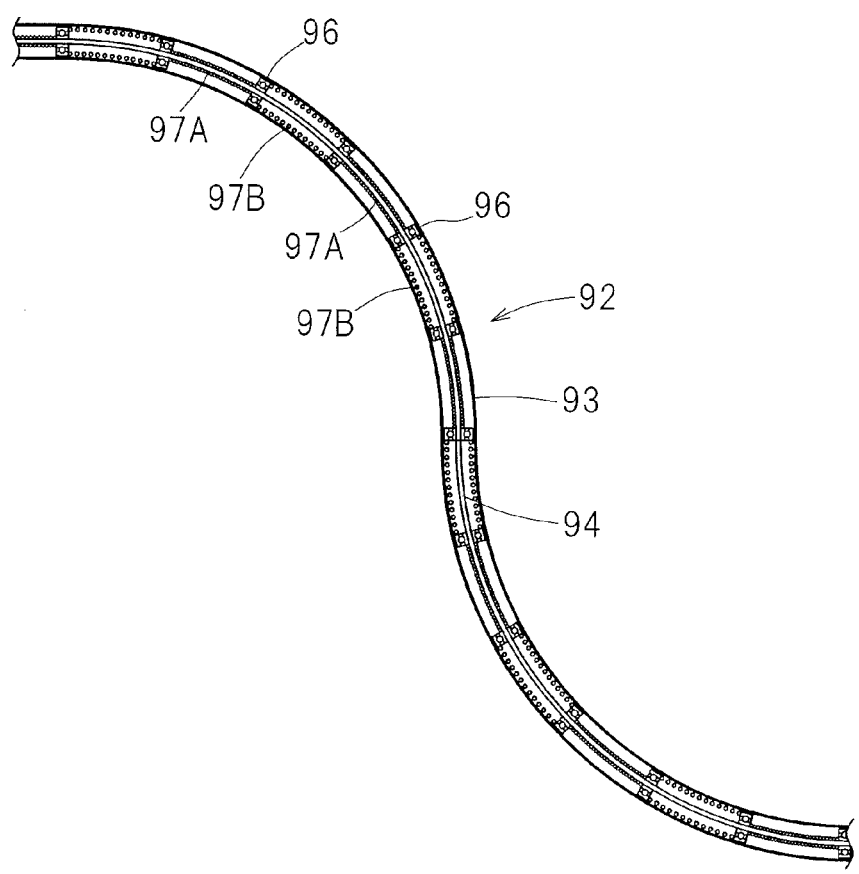
FIG. 43 is a longitudinal sectional view showing a tool rotating cable employed in the tool rotating drive mechanism shown in FIG. 42.

The tool rotating drive mechanism 91 in this embodiment is so designed and so configured that as best shown in FIG. 42, rotation of the output shaft 41a of the tool rotating drive source 41 provided in the drive source housing 100 can be transmitted to the base end of the rotary shaft 22 within the drive unit housing 4a through an inner wire 94 (FIG. 43) of a tool rotating cable 92. For example, the tool rotating cable 92 has such a structure as shown in FIG. 43, in which a flexible inner wire 94 is rotatably supported within a center of a flexible outer tube 93 by means of a plurality of rolling bearings 96. This inner wire 94 has its opposite ends linked to the output shaft 41a of the tool rotating drive source 41 and the base end of the rotary shaft 22. Between the neighboring bearings 96, spring elements 97A and 97B for generating a preload in those rolling bearings 96 are provided. The spring elements 97A and 97B are in the form of, for example, compression coil springs. The spring element 97A for an inner ring generates a preload in the inner ring of the rolling bearing 96 and the spring element 97B for an outer ring generates a preload in an outer ring, and they are arranged alternately. With the preload applied to the rolling bearings 96 through the spring elements 97A and 97B in the manner described above, the inner wire 94 can be rotated at a high speed. It is, however, to be noted that any commercially available flexible shaft may be employed.

Also, the attitude altering drive mechanism 101 employed in this embodiment is operable to transmit the operation of the attitude altering drive source 42, provided within the drive source housing 100, to a drive mechanism unit 85 within the drive unit housing 4a through the attitude altering cable 102. The drive mechanism unit 85 referred to above corresponds to the attitude altering drive mechanism 4c in the previously described embodiment, from which the attitude altering drive source 42 is excluded, and instead of the output rod 42a of the attitude altering drive source 42 in the attitude altering drive mechanism 4c, an advancing and retracting member 95 is employed, which is capable of selectively advancing and retracting relative to the drive unit housing 4a with its tip end held in contact with the lever 43b of the force increasing and transmitting mechanism 43. The advancing and retracting member 95 is selectively advanced and retracted one at a time relative to the drive unit housing 4a by converting a rotary movement into a linear movement by means of a screw mechanism 95a such as, for example, a ball screw. In such case, the attitude altering drive source is employed in the form of a rotary actuator and the rotation of the attitude altering drive source 42 is transmitted to the advancing and retracting member 95 by means of the inner wire 104 (FIG. 43) of the attitude altering cable 102.

Figure 44:
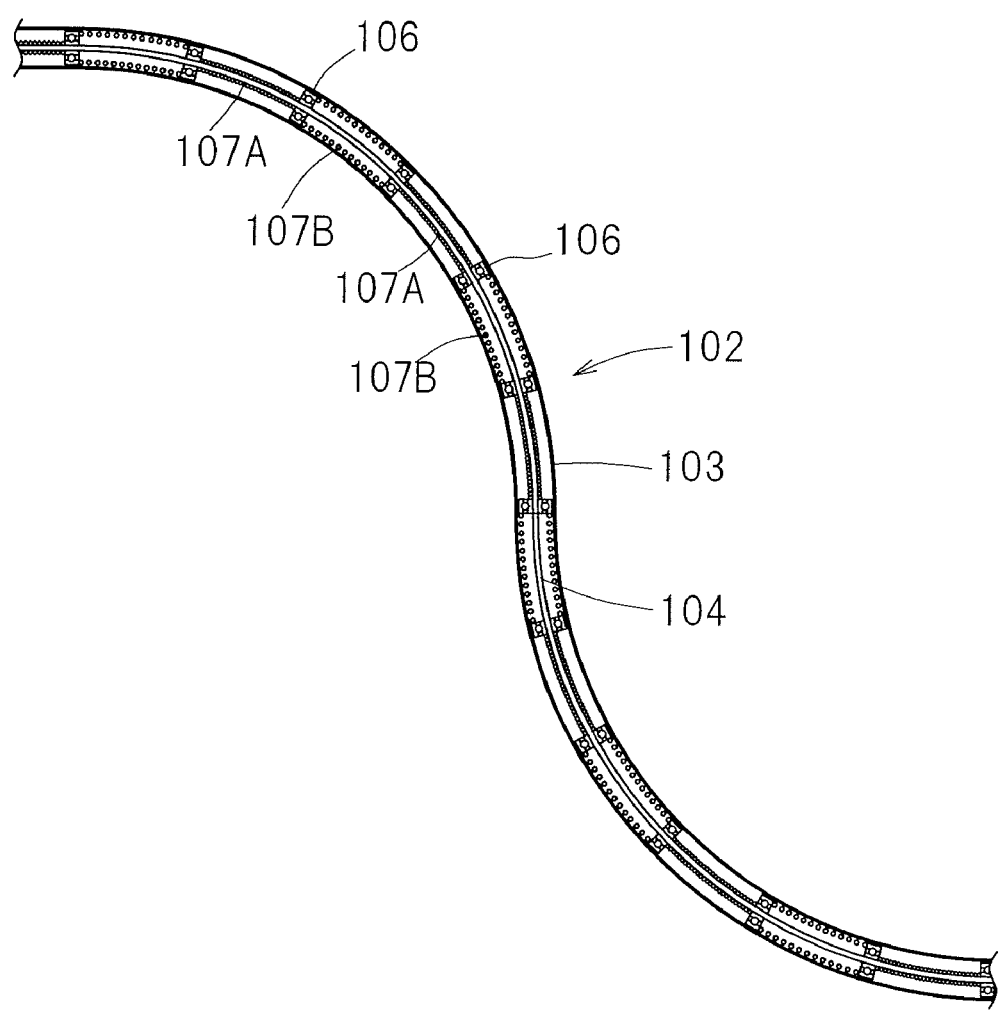
FIG. 44 is a longitudinal sectional view showing an attitude altering cable employed in the attitude altering drive mechanism shown in FIG. 42.

The attitude altering cable 102 is of a structure similar to the previously described tool rotating cable 92 and, for example, as shown in FIG. 44. Specifically, a flexible inner wire 104 is rotatably supported by a plurality of rolling bearings 106 at the center of a flexible outer tube 103. Also, the inner wire 104 has its opposite ends connected respectively with the output shaft 42a of the attitude altering drive source 42 and an advancing and retracting member 95. Spring elements 107A and 107B for generating a preload in the rolling bearings 106 are provided between the neighboring rolling bearings 106. The spring elements 107A and 107B are in the form of, for example, compression coil springs. The spring element 107A for an inner ring generates a preload in the inner ring of the rolling bearing 106 and the spring element 107B for an outer ring generates a preload in an outer ring, and they are arranged alternately. With the preload applied to the rolling bearings 106 through the spring elements 107A and 107B in the manner described above, the inner wire 104 can be rotated at a high speed. It is, however, to be noted that any commercially available flexible shaft may be employed.

Figure 41:
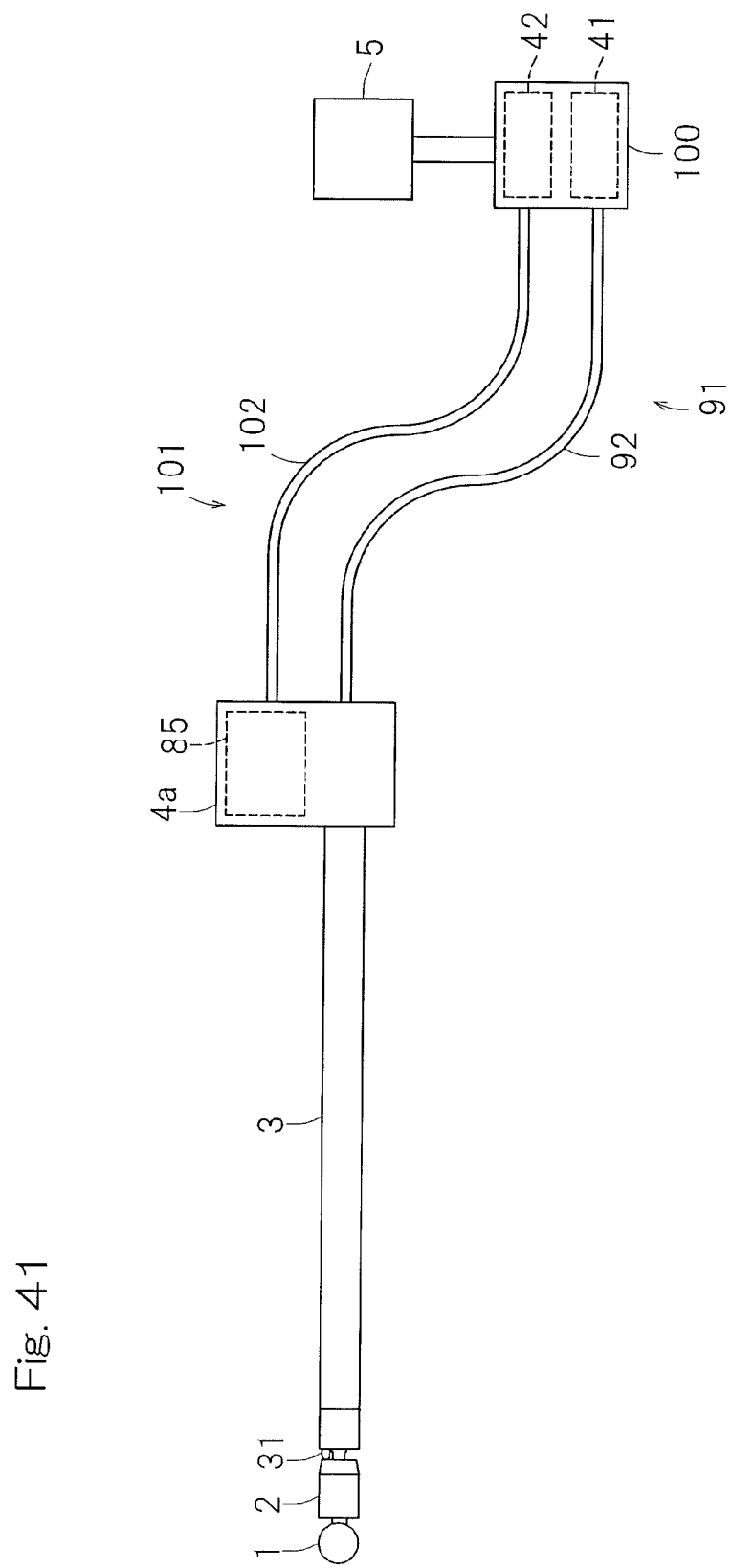
FIG. 41 is a diagram showing a schematic structure of the remote controlled actuator according to a twenty fourth preferred embodiment of the present invention.

As shown in FIG. 41, the controller 5 for controlling the tool rotation drive source 41 and the attitude altering drive source 42 is connected with the drive source housing 100. The distal end member 2 and the spindle guide section 3 are of a structure similar to those employed in any one of the foregoing embodiments.

Figure 45:
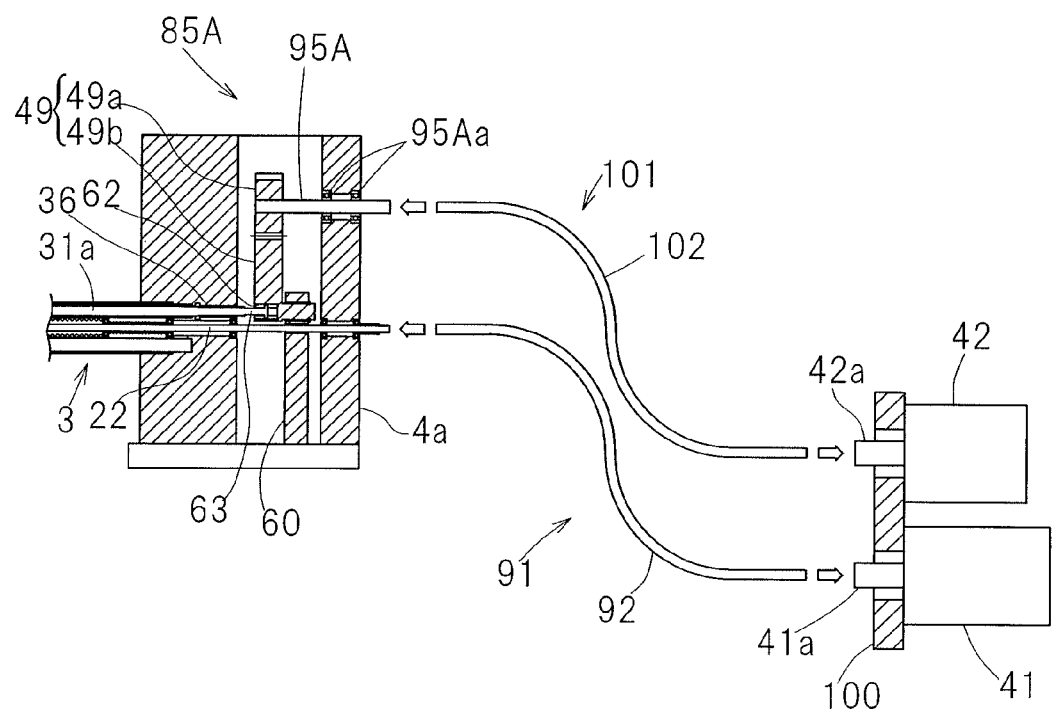
FIG. 45 is a diagram showing the structure of the tool rotating drive mechanism and the attitude altering drive mechanism both employed in the remote controlled actuator.

FIG. 45 illustrates a modification of FIG. 42 and a type in which, in place of the force increasing and transmitting mechanism 43, a rotation-reducing and transmitting mechanism is employed. The attitude altering drive mechanism 101 employed in the practice of this modification is of a structure, in which rotation of the output shaft 42 of the attitude altering drive source 42 provided within the drive source housing 100 can be transmitted to a drive mechanism unit 85A within the drive unit housing 4a through an attitude altering cable 102. The drive mechanism unit 85A referred to above corresponds to the attitude altering drive mechanism 4c in the previously described embodiment, from which the attitude altering drive source 42 is excluded, and instead of the output shaft 42a of the attitude altering drive source 42 in the attitude altering drive mechanism 4c, the use is made of a gear mounting shaft 95A to which a round spur gear 49a is fitted. The gear mounting shaft 95A is rotatably supported by the drive unit housing 4a by means of rolling bearings 95Aa. The attitude altering drive source 42 is employed in the form of a rotary actuator and the rotation of the attitude altering drive source 42 is transmitted to the gear mounting shaft 95A through the inner wire 104 (FIG. 44) of the attitude altering cable 102.

Since, as is the case with this twenty fourth embodiment the tool rotating drive source 41 and the attitude altering drive source 42 are provided outside the drive unit housing 4a, the drive unit housing 4a can be downsized. For this reason, the handleability of the remote controlled actuator of a type that is manipulated with the drive unit housing 4a handheld can be increased.

Although the present invention has been fully described as applied to the remote controlled actuator for medical use, the present invention can be equally applied to the remote controlled actuator for any other use than the medical use. By way of example, if it is designed for use in machine processing, drilling to form a curved hole and cutting at a site deep into the groove can be accomplished.

With the present invention having been fully described hereinabove, the present invention can be embodied in any one of the following modes 1 to 3, all of which exemplify the type in which the attitude altering member according to the present invention does not necessarily require a flexibility.

[Mode 1]

The remote controlled actuator according to the Mode 1 includes a spindle guide section of an elongated shape, a distal end member connected with a distal end of the spindle guide section for alteration in attitude, a tool rotatably provided at the distal end of the spindle guide section, a tool rotating drive source for rotating the tool, and an attitude altering drive source for manipulating the attitude of the distal end member; in which the distal end member rotatably supports a spindle for holding the tool; the spindle guide section includes a rotary shaft for transmitting rotation of the tool rotating drive source to the spindle and having a guide hole defined therein so as to extend to both ends, and an attitude altering member reciprocally movably inserted within the guide hole for altering the attitude of the distal end member; the attitude altering member is, while a tip end thereof is held in contact with the distal end member directly or indirectly, selectively advanced and retracted one at a time; and a drive mechanism unit is provided for transmitting an operation of the attitude alternating drive source to the attitude altering member. The drive mechanism unit includes a screw mechanism made up of a male screw portion, formed in a base end of the attitude altering member, and a female portion fixed in a drive unit housing for accommodating the drive mechanism unit and threadingly engaged with the male screw portion. The drive unit housing is coupled with a base end of the spindle guide section. The attitude altering drive source is in the form of a rotary actuator such that, when the base end of the attitude altering member is rotated by the rotary actuator, the attitude altering member is selectively advanced and retracted one at a time by the screw mechanism.

[Mode 2]

The remote controlled actuator according to the Mode 2 includes a spindle guide section of an elongated shape, a distal end member connected with a distal end of the spindle guide section for alteration in attitude, and a drive unit housing to which a base end of the spindle guide section is coupled; in which the distal end member rotatably supports a spindle for holding a tool; the spindle guide section includes a rotary shaft for transmitting rotation of a tool rotating drive source to the spindle and having a guide hole defined therein so as to extend to both ends, and an attitude altering member reciprocally movably inserted within the guide hole for altering the attitude of the distal end member; the attitude altering member is, while a tip end thereof is held in contact with the distal end member, selectively advanced and retracted one at a time; an attitude altering drive source for selectively advancing and retracting the attitude altering member one at a time is provided within the drive unit housing; and a rotation preventing mechanism is provided for preventing the distal end member from rotating about a center line relative to the spindle guide section.

[Mode 3]

The remote controlled actuator according to the Mode 3 includes a spindle guide section of an elongated shape, a distal end member connected with a distal end of the spindle guide section for alteration in attitude, and a drive unit housing to which a base end of the spindle guide section is coupled; in which the distal end member rotatably supports a spindle for holding the tool; the spindle guide section includes an outer shell pipe defining an outer shell for the spindle guide section, a rotary shaft provided within the outer shell pipe for transmitting rotation of a tool rotating drive source within the drive unit housing to the spindle, and a hollow guide pipe provided within the outer shell pipe and extending to both ends; an attitude altering member reciprocally movably inserted within the guide hole for altering the attitude of the distal end member; the attitude altering member is, while a tip end thereof is held in contact with the distal end member, selectively advanced and retracted one at a time; an attitude altering drive source for selectively advancing and retracting the attitude altering member one at a time is provided within the drive unit housing; and a pipe fixing segment is provided for fixedly connecting the outer shell pipe and the guide pipe with each other.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1: Tool
2: Distal end member
3: Spindle guide section
4a: Drive unit housing
5: Controller
11a: Guided member
13: Spindle
15: Distal end member connecting unit
21a: Guide member
22: Rotary shaft
25: Outer shell pipe
26, 29: Rolling bearing
27A, 27B: Spring element
30: Guide pipe
30a: Guide hole
31: Attitude altering member
31a: Ball (Force transmitting member)
31b: Pillar shaped element (Force transmitting member)
32: Restoring elastic member
34: Reinforcement shaft
37: Rotation preventing mechanism
41: Tool rotating drive source
42: Attitude altering drive source
43: Force increasing and transmitting mechanism
45: Operating amount detector
46: Attitude detector
47: Supply power meter
48: Load detector
49: Rotation-reducing and transmitting mechanism
50: Cooling unit
F1, F2: Guide face
85: Drive mechanism unit

What is claimed is:

1. A remote controlled actuator which comprises a spindle guide section of an elongated configuration, a distal end member fitted to a distal end of the spindle guide section through a distal end member connecting unit for alteration in attitude, a tool rotatably fitted to the distal end member, a tool rotating drive source for rotating the tool, and an attitude altering drive source for manipulating the attitude of the distal end member;

wherein the distal end member rotatably supports a spindle for holding the tool;

wherein the spindle guide section includes a rotary shaft for transmitting rotation of the tool rotating drive source to the spindle, a guide hole defined within the spindle guide section so as to extend to a proximal end and the distal end of the spindle guide section, and an attitude altering member reciprocally movably inserted within the guide hole for altering the attitude of the distal end member about an axis perpendicular to a longitudinal axis of the spindle;

wherein the spindle guide section comprises an outer shell pipe forming an outer shell for the spindle guide section and the guide hole is an inner diametric hole of a guide pipe provided within the outer shell pipe; and wherein the attitude altering member is, while a proximal end of the attitude altering member is held in contact with the distal end member, selectively advanced and retracted by the attitude altering drive source.

2. The remote controlled actuator as claimed in claim 1, in which the attitude altering member is an attitude altering wire.

3. The remote controlled actuator as claimed in claim 1, further comprising a drive mechanism unit for transmitting an operation of the attitude altering drive source to the attitude altering member, the drive mechanism unit including a screw mechanism made up of a male screw portion, formed in a base end of the attitude altering member, and a female screw portion fixed to a drive unit housing for accommodating the drive mechanism unit and engaged with the male screw portion,
   wherein the drive unit housing is coupled with a base end of the spindle guide section, and
   wherein the attitude altering drive source is a rotary actuator and the attitude altering member is selectively advanced and refracted one at a time by the action of the screw mechanism when the base end of the attitude altering member is rotated by the rotary actuator.

4. The remote controlled actuator as claimed in claim 3, further comprising a rotation-reducing and transmitting mechanism for decelerating the rotation of the rotary actuator and transmitting to the base end of the attitude altering member.

5. The remote controlled actuator as claimed in claim 1, in which the tool rotating drive source and the attitude altering drive source are provided outside a drive unit housing to which a base end of the spindle guide section is connected.

6. The remote controlled actuator as claimed in claim 1, in which one or both of the tool rotating drive source and the attitude altering drive source is provided outside a drive unit housing to which a base end of the spindle guide section is connected, and a drive force of one of the tool rotating drive source and the attitude altering drive source, which is provided outside the drive unit housing, is transmitted to the rotary shaft or the attitude altering member through a flexible cable.

7. The remote controlled actuator as claimed in claim 1, in which the guide hole and the attitude altering member inserted within the guide hole are provided at two locations, and the attitude altering drive source is provided for each one of the attitude altering members so that the attitude of the distal end member can be altered and maintained in dependence on the balance of respective working forces of the attitude altering members at the two locations acting on the distal end member.

8. The remote controlled actuator as claimed in claim 1, in which the distal end member connecting unit is of a type supporting the distal end member for tilting motion in any desired direction and in which the guide hole and the attitude altering member inserted within the guide hole are provided at three or more locations about a center of tilt of the distal end member and the attitude altering drive source is provided for each one of the attitude altering members so that the attitude of the distal end member can be altered and maintained in dependence on the balance of respective working forces of the attitude altering members at the three or more locations acting on the distal end member.

9. The remote controlled actuator as claimed in claim 8, in which the distal end member connecting unit is of a structure, in which a guide member on the side of the spindle guide section and a guided member on the side of the distal end member contact each other on a spherical or cylindrical guide surface having a center of curvature lying on a center line of the spindle and a center of connection between the spindle and the rotary shaft lies at the same position as the center of curvature of the guide surface.

10. The remote controlled actuator as claimed in claim 1, in which the attitude altering drive source is a linear actuator.

11. The remote controlled actuator as claimed in claim 10, further comprising a force increasing and transmitting mechanism comprised of a lever mechanism for force increasing an output of the linear actuator and transmitting it to the attitude altering member.

12. The remote controlled actuator as claimed in claim 1, further comprising a rotation preventing mechanism for preventing the distal end member from rotating about a center line of the distal end member relative to the spindle guide section.

13. The remote controlled actuator as claimed in claim 1, in which the rotary shaft is arranged at the center of the outer shell pipe and a plurality of reinforcement shafts and the guide pipe are arranged in a row in a circumferential direction between the rotary shaft and an inner diametric surface of the outer shell pipe.

14. The remote controlled actuator as claimed in claim 13, further comprising a plurality of rolling bearings for rotatably supporting the rotary shaft within the spindle guide section, the plurality of rolling bearings having respective outer diametric surfaces supported by the plurality of reinforcement shafts and the guide pipe.

15. The remote controlled actuator as claimed in claim 14, further comprising a cooling unit for cooling the bearings or the tool with a liquid coolant flowing inside the outer shell pipe.

16. The remote controlled actuator as claimed in claim 1, further comprising a plurality of rolling bearings for rotatably supporting the rotary shaft within the spindle guide section and a spring element for applying a preload to the plurality of rolling bearings, the spring element being provided between neighboring rolling bearings in the plurality of rolling bearings.

17. A remote controlled actuator which comprises a spindle guide section of an elongated configuration, a distal end member fitted to a distal end of the spindle guide section through a distal end member connecting unit for alteration in attitude, a tool rotatably fitted to the distal end member, a tool rotating drive source for rotating the tool, and an attitude altering drive source for manipulating the attitude of the distal end member;
   wherein the distal end member rotatably supports a spindle for holding the tool;
   wherein the spindle guide section includes a rotary shaft for transmitting rotation of the tool rotating drive source to the spindle, a guide hole defined within the spindle guide section so as to extend to a proximal end and the distal end of the spindle guide section, and an attitude altering member reciprocally movably inserted within the guide hole for altering the attitude of the distal end member about an axis perpendicular to a longitudinal axis of the spindle;
   wherein the spindle guide section comprises an outer shell pipe forming an outer shell for the spindle guide section to accommodate the rotary shaft disposed within the outer shell pipe for transmitting rotation of the tool rotating drive source within a drive unit housing to the spindle, and a hollow guide pipe provided within the outer shell pipe and extending to both ends of the outer shell pipe, and further comprising a pipe fixing segment for fixedly connecting the outer shell pipe and the guide pipe with each other; and
   wherein the attitude altering member is, while a proximal end of the attitude altering member is held in contact with the distal end member, selectively advanced and retracted by the attitude altering drive source.

18. A remote controlled actuator which comprises a spindle guide section of an elongated configuration, a distal end member fitted to a distal end of the spindle guide section through a distal end member connecting unit for alteration in attitude, a tool rotatably fitted to the distal end member, a tool rotating drive source for rotating the tool, and an attitude altering drive source for manipulating the attitude of the distal end member;

wherein the distal end member rotatably supports a spindle for holding the tool;

wherein the spindle guide section includes a rotary shaft for transmitting rotation of the tool rotating drive source to the spindle, a guide hole defined within the spindle guide section so as to extend to a proximal end and the distal end of the spindle guide section, and an attitude altering member reciprocally movably inserted within the guide hole for altering the attitude of the distal end member about an axis perpendicular to a longitudinal axis of the spindle;

wherein the guide hole and the attitude altering member inserted within the guide hole are provided at one location, and a restoring elastic member for urging the distal end member towards a predetermined attitude side is provided to enable the attitude altering member to alter the attitude of the distal end member against a biasing force of the restoring elastic member; and wherein the attitude altering member is, while a proximal end of the attitude altering member is held in contact with the distal end member, selectively advanced and retracted by the attitude altering drive source.

19. The remote controlled actuator as claimed in claim 18, in which the distal end member connecting unit is of a structure, in which a guide member on a side of the spindle guide section and a guided member on a side of the distal end member contact each other on a spherical or cylindrical guide surface having a center of curvature lying on a center line of the spindle, and a center of connection between the spindle and the rotary shaft lies at the same position as the center of curvature of the guide surface.

* * * * *

UNITED STATES PATENT AND TRADEMARK OFFICE
CERTIFICATE OF CORRECTION

PATENT NO. : 8,393,242 B2
APPLICATION NO. : 13/024696
DATED : March 12, 2013
INVENTOR(S) : Takayoshi Ozaki et al.

It is certified that error appears in the above-identified patent and that said Letters Patent is hereby corrected as shown below:

In the Claims:

Column 35, Line 11 please delete "refracted" and insert --retracted-- therefor.

Signed and Sealed this
Second Day of July, 2013

Teresa Stanek Rea
*Acting Director of the United States Patent and Trademark Office*